United States Patent
Kim et al.

(10) Patent No.: US 9,644,217 B2
(45) Date of Patent: May 9, 2017

(54) METHOD FOR PRODUCING RETINOID FROM MICROORGANISM

(75) Inventors: Seon Won Kim, Gyeongsangnam-do (KR); Hui Jeong Jang, Gyeongsangnam-do (KR); Sang Hwal Yoon, Chungcheongnam-do (KR); Bo Kyung Ha, Gyeongsangnam-do (KR); Hee Kyung Ryu, Gyeonsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 0 days.

(21) Appl. No.: 14/235,841

(22) PCT Filed: Jul. 30, 2012

(86) PCT No.: PCT/KR2012/006071
§ 371 (c)(1),
(2), (4) Date: Jan. 29, 2014

(87) PCT Pub. No.: WO2013/019051
PCT Pub. Date: Feb. 7, 2013

(65) Prior Publication Data
US 2014/0170720 A1    Jun. 19, 2014

(30) Foreign Application Priority Data

Jul. 29, 2011 (KR) .......... 10-2011-0075715
Jul. 30, 2012 (KR) .......... 10-2012-0083185

(51) Int. Cl.
| | |
|---|---|
| C12P 7/24 | (2006.01) |
| C12P 7/22 | (2006.01) |
| C12N 1/28 | (2006.01) |
| C12N 1/38 | (2006.01) |
| C12N 15/52 | (2006.01) |
| C12P 7/40 | (2006.01) |
| C12N 15/70 | (2006.01) |
| C12P 5/00 | (2006.01) |
| C12P 7/62 | (2006.01) |

(52) U.S. Cl.
CPC .......... *C12P 7/24* (2013.01); *C12N 1/28* (2013.01); *C12N 1/38* (2013.01); *C12N 15/52* (2013.01); *C12N 15/70* (2013.01); *C12P 5/007* (2013.01); *C12P 7/22* (2013.01); *C12P 7/40* (2013.01); *C12P 7/62* (2013.01)

(58) Field of Classification Search
None
See application file for complete search history.

(56) References Cited

FOREIGN PATENT DOCUMENTS

KR    10-2009-0078113 A    7/2009

OTHER PUBLICATIONS

Human Translation of KR 10-2009-0078113. Jul. 17, 2009. Jang et al. Retrieved from K-PION on Aug. 27, 2015. p. 1-17.*
Kizer L et al. Application of Functional Genomics to Pathway Optimization for Increased Isoprenoid Production. 2008. Applied and Environmental Microbiology. vol. 74, No. 10. p. 3229-3241.*
Prather KLJ et al. De novo biosynthetic pathways: rational design of microbial chemical factories. 2008. Current Opinion in Biotechnology. 19:468-474.*
Ajikumar PK et al. Isoprenoid Pathway Optimization for Taxol Precursor Overproduction in *Escherichia coli*. 2010. Science. vol. 330(6000). p. 70-74.*
International Search Report for PCT/KR2012/006071.
Jang, H.-J., et al., "Retinoid production using metabolically engineered *Escherichia coli* with a two-phase culture system." Microbial Cell Factories, 10:59, (Jul. 29, 2011).
Ha, B.-K., et al., "Improved Retinoids Production from Metabolically Engineered *Escherichia coli* with a Two-phase Culture System." Journal of KSBB conference, pp. 185 (Apr. 2012).
Yoon, K. W., et al., "In situ recovery oflycopene during biosynthesis with recombinant *Escherichia coli*." J. Biotechnol. vol. 135(3):291-294 (2008).
Kim, Y. S., et al. "Effective production of retina 1 from beta-carotene using recombinant mouse beta-carotene 15,15'—monooxygenase." Appl. Microbiol. Biotechnol., vol. 76(6): 1339-1345 (Oct. 2007).

* cited by examiner

*Primary Examiner* — Paul Holland
(74) *Attorney, Agent, or Firm* — The PL Law Group, PLLC

(57) ABSTRACT

The present invention relates to a method for producing retinoid from a microorganism, and more specifically, to a method for effectively obtaining retinoid, which lacks stability, from a microorganism by cultivating the microorganism capable of producing retinoid in a medium containing a lipophilic substance, and separating retinoid from the lipophilic substance.

19 Claims, 27 Drawing Sheets

SEQUENCE LISTING

<160> NUMBER OF SEQ ID NOS: 65

<210> SEQ ID NO 1
<211> LENGTH: 803
<212> TYPE: PRT
<213> ORGANISM: Enterococcus faecalis

<400> SEQUENCE: 1

```
Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
        115                 120                 125

Tyr Glu Thr Glu Ser Tyr Asp Ala Pro Phe Ser Ser Met Met Tyr Asp
    130                 135                 140

Gly Leu Thr Asp Ala Phe Ser Gly Gln Ala Met Gly Leu Thr Ala Glu
145                 150                 155                 160

Asn Val Ala Glu Lys Tyr His Val Thr Arg Glu Glu Gln Asp Gln Phe
                165                 170                 175

Ser Val His Ser Gln Leu Lys Ala Ala Gln Ala Gln Ala Glu Gly Ile
            180                 185                 190

Phe Ala Asp Glu Ile Ala Pro Leu Glu Val Ser Gly Thr Leu Val Glu
        195                 200                 205

Lys Asp Glu Gly Ile Arg Pro Asn Ser Ser Val Glu Lys Leu Gly Thr
    210                 215                 220

Leu Lys Thr Val Phe Lys Glu Asp Gly Thr Val Thr Ala Gly Asn Ala
```

-continued

```
            225                 230                 235                 240
Ser Thr Ile Asn Asp Gly Ala Ser Ala Leu Ile Ile Ala Ser Gln Glu
                    245                 250                 255
Tyr Ala Glu Ala His Gly Leu Pro Tyr Leu Ala Ile Ile Arg Asp Ser
                260                 265                 270
Val Glu Val Gly Ile Asp Pro Ala Tyr Met Gly Ile Ser Pro Ile Lys
            275                 280                 285
Ala Ile Gln Lys Leu Leu Ala Arg Asn Gln Leu Thr Thr Glu Glu Ile
        290                 295                 300
Asp Leu Tyr Glu Ile Asn Glu Ala Phe Ala Ala Thr Ser Ile Val Val
305                 310                 315                 320
Gln Arg Glu Leu Ala Leu Pro Glu Glu Lys Val Asn Ile Tyr Gly Gly
                325                 330                 335
Gly Ile Ser Leu Gly His Ala Ile Gly Ala Thr Gly Ala Arg Leu Leu
                340                 345                 350
Thr Ser Leu Ser Tyr Gln Leu Asn Gln Lys Glu Lys Lys Tyr Gly Val
                355                 360                 365
Ala Ser Leu Cys Ile Gly Gly Leu Gly Leu Ala Met Leu Leu Glu
                370                 375                 380
Arg Pro Gln Gln Lys Lys Asn Ser Arg Phe Tyr Gln Met Ser Pro Glu
385                 390                 395                 400
Glu Arg Leu Ala Ser Leu Leu Asn Glu Gly Gln Ile Ser Ala Asp Thr
                405                 410                 415
Lys Lys Glu Phe Glu Asn Thr Ala Leu Ser Ser Gln Ile Ala Asn His
                420                 425                 430
Met Ile Glu Asn Gln Ile Ser Glu Thr Glu Val Pro Met Gly Val Gly
                435                 440                 445
Leu His Leu Thr Val Asp Glu Thr Asp Tyr Leu Val Pro Met Ala Thr
                450                 455                 460
Glu Glu Pro Ser Val Ile Ala Ala Leu Ser Asn Gly Ala Lys Ile Ala
465                 470                 475                 480
Gln Gly Phe Lys Thr Val Asn Gln Gln Arg Leu Met Arg Gly Gln Ile
                485                 490                 495
Val Phe Tyr Asp Val Ala Asp Ala Glu Ser Leu Ile Asp Glu Leu Gln
                500                 505                 510
Val Arg Glu Thr Glu Ile Phe Gln Gln Ala Glu Leu Ser Tyr Pro Ser
                515                 520                 525
Ile Val Lys Arg Gly Gly Leu Arg Asp Leu Gln Tyr Arg Ala Phe
                530                 535                 540
Asp Glu Ser Phe Val Ser Val Asp Phe Leu Val Asp Val Lys Asp Ala
545                 550                 555                 560
Met Gly Ala Asn Ile Val Asn Ala Met Leu Glu Gly Val Ala Glu Leu
                565                 570                 575
Phe Arg Glu Trp Phe Ala Glu Gln Lys Ile Leu Phe Ser Ile Leu Ser
                580                 585                 590
Asn Tyr Ala Thr Glu Ser Val Val Thr Met Lys Thr Ala Ile Pro Val
                595                 600                 605
Ser Arg Leu Ser Lys Gly Ser Asn Gly Arg Glu Ile Ala Glu Lys Ile
                610                 615                 620
Val Leu Ala Ser Arg Tyr Ala Ser Leu Asp Pro Tyr Arg Ala Val Thr
625                 630                 635                 640
His Asn Lys Gly Ile Met Asn Gly Ile Glu Ala Val Val Leu Ala Thr
                645                 650                 655
```

```
Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
            675                 680                 685

Gln Leu Ile Gly Glu Ile Ser Val Pro Leu Ala Leu Ala Thr Val Gly
            690                 695                 700

Gly Ala Thr Lys Val Leu Pro Lys Ser Gln Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
            755                 760                 765

Gly Ala Thr Gly Lys Glu Val Glu Ala Val Ala Gln Gln Leu Lys Arg
            770                 775                 780

Gln Lys Thr Met Asn Gln Asp Arg Ala Leu Ala Ile Leu Asn Asp Leu
785                 790                 795                 800

Arg Lys Gln

<210> SEQ ID NO 2
<211> LENGTH: 383
<212> TYPE: PRT
<213> ORGANISM: Enterococcus faecalis

<400> SEQUENCE: 2

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220
```

```
Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
            245                 250                 255

Glu Arg Ile Leu Ala Arg Tyr Glu Glu Ser Ile Ile Tyr Ser Arg Arg
        260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
            325                 330                 335

Asp Asn Arg Thr Glu Leu Ser Ile Ala Glu Tyr Glu Ala Met Phe Ala
        340                 345                 350

Glu Thr Leu Asp Thr Asp Ile Asp Gln Thr Leu Glu Asp Glu Leu Lys
    355                 360                 365

Tyr Ser Ile Ser Ala Ile Asn Asn Thr Val Arg Ser Tyr Arg Asn
370                 375                 380

<210> SEQ ID NO 3
<211> LENGTH: 292
<212> TYPE: PRT
<213> ORGANISM: Streptococcus pneumoniae

<400> SEQUENCE: 3

Met Thr Lys Lys Val Gly Val Gly Gln Ala His Ser Lys Ile Ile Leu
1               5                   10                  15

Ile Gly Glu His Ala Val Val Tyr Gly Tyr Pro Ala Ile Ser Leu Pro
            20                  25                  30

Leu Leu Glu Val Glu Val Thr Cys Lys Val Val Ser Ala Glu Ser Pro
        35                  40                  45

Trp Arg Leu Tyr Glu Glu Asp Thr Leu Ser Met Ala Val Tyr Ala Ser
    50                  55                  60

Leu Glu Tyr Leu Asp Ile Thr Glu Ala Cys Val Arg Cys Glu Ile Asp
65                  70                  75                  80

Ser Ala Ile Pro Glu Lys Arg Gly Met Gly Ser Ser Ala Ala Ile Ser
                85                  90                  95

Ile Ala Ala Ile Arg Ala Val Phe Asp Tyr Tyr Gln Ala Asp Leu Pro
            100                 105                 110

His Asp Val Leu Glu Ile Leu Val Asn Arg Ala Glu Met Ile Ala His
        115                 120                 125

Met Asn Pro Ser Gly Leu Asp Ala Lys Thr Cys Leu Ser Asp Gln Pro
    130                 135                 140

Ile Arg Phe Ile Lys Asn Val Gly Phe Thr Glu Leu Glu Met Asp Leu
145                 150                 155                 160

Ser Ala Tyr Leu Val Ile Ala Asp Thr Gly Val Tyr Gly His Thr Arg
                165                 170                 175

Glu Ala Ile Gln Val Val Gln Asn Lys Gly Lys Asp Ala Leu Pro Phe
            180                 185                 190

Leu His Ala Leu Gly Glu Leu Thr Gln Gln Ala Glu Val Ala Ile Ser
        195                 200                 205

Gln Lys Tyr Ala Glu Gly Leu Gly Leu Ile Phe Ser Gln Ala His Leu
```

```
                210                 215                 220
His Leu Lys Glu Ile Gly Val Ser Ser Pro Glu Ala Asp Phe Leu Val
225                 230                 235                 240

Glu Thr Ala Leu Ser Tyr Gly Ala Leu Gly Ala Lys Met Ser Gly Gly
                245                 250                 255

Gly Leu Gly Gly Cys Ile Ile Ala Leu Val Thr Asn Leu Thr His Ala
                260                 265                 270

Gln Glu Leu Ala Glu Arg Leu Glu Lys Gly Ala Val Gln Thr Trp
                275                 280                 285

Ile Glu Ser Leu
    290

<210> SEQ ID NO 4
<211> LENGTH: 336
<212> TYPE: PRT
<213> ORGANISM: Streptococcus pneumoniae

<400> SEQUENCE: 4

Met Ile Ala Val Lys Thr Cys Gly Lys Leu Tyr Trp Ala Gly Glu Tyr
1               5                   10                  15

Ala Ile Leu Glu Pro Gly Gln Leu Ala Leu Ile Lys Asp Ile Pro Ile
                20                  25                  30

Tyr Met Arg Ala Glu Ile Ala Phe Ser Asp Ser Tyr Arg Ile Tyr Ser
                35                  40                  45

Asp Met Phe Asp Phe Ala Val Asp Leu Arg Pro Asn Pro Asp Tyr Ser
            50                  55                  60

Leu Ile Gln Glu Thr Ile Ala Leu Met Gly Asp Phe Leu Ala Val Arg
65                  70                  75                  80

Gly Gln Asn Leu Arg Pro Phe Ser Leu Lys Ile Cys Gly Lys Met Glu
                85                  90                  95

Arg Glu Gly Lys Lys Phe Gly Leu Gly Ser Ser Gly Ser Val Val Val
                100                 105                 110

Leu Val Val Lys Ala Leu Leu Ala Leu Tyr Asn Leu Ser Val Asp Gln
            115                 120                 125

Asn Leu Leu Phe Lys Leu Thr Ser Ala Val Leu Leu Lys Arg Gly Asp
            130                 135                 140

Asn Gly Ser Met Gly Asp Leu Ala Cys Ile Val Ala Glu Asp Leu Val
145                 150                 155                 160

Leu Tyr Gln Ser Phe Asp Arg Gln Lys Ala Ala Ala Trp Leu Glu Glu
                165                 170                 175

Glu Asn Leu Ala Thr Val Leu Glu Arg Asp Trp Gly Phe Phe Ile Ser
            180                 185                 190

Gln Val Lys Pro Thr Leu Glu Cys Asp Phe Leu Val Gly Trp Thr Lys
            195                 200                 205

Glu Val Ala Val Ser Ser His Met Val Gln Gln Ile Lys Gln Asn Ile
            210                 215                 220

Asn Gln Asn Phe Leu Ser Ser Lys Glu Thr Val Val Ser Leu Val
225                 230                 235                 240

Glu Ala Leu Glu Gln Gly Lys Ala Glu Lys Val Ile Glu Gln Val Glu
                245                 250                 255

Val Ala Ser Lys Leu Leu Glu Gly Leu Ser Thr Asp Ile Tyr Thr Pro
            260                 265                 270

Leu Leu Arg Gln Leu Lys Glu Ala Ser Gln Asp Leu Gln Ala Val Ala
            275                 280                 285
```

Lys Ser Ser Gly Ala Gly Gly Gly Asp Cys Gly Ile Ala Leu Ser Phe
290                 295                 300

Asp Ala Gln Ser Ser Arg Asn Thr Leu Lys Asn Arg Trp Ala Asp Leu
305                 310                 315                 320

Gly Ile Glu Leu Leu Tyr Gln Glu Arg Ile Gly His Asp Asp Lys Ser
                325                 330                 335

<210> SEQ ID NO 5
<211> LENGTH: 317
<212> TYPE: PRT
<213> ORGANISM: Streptococcus pneumoniae

<400> SEQUENCE: 5

Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
            35                  40                  45

Ser Pro Leu Pro Ala Asn Val Thr Ala Asp Glu Phe Tyr Ile Asn Gly
50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asp Arg
            115                 120                 125

Ser Gln Leu Ala Gln Glu Ala Lys Phe Ala Ser Gly Ser Ser Ser Arg
            130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
            195                 200                 205

Asp Tyr Gln Asp Met Leu Ile Tyr Leu Lys Glu Asn Asp Phe Ala Lys
            210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
            275                 280                 285

Asp Leu Glu His Leu Ser Glu Ile Phe Gly Arg Tyr Arg Leu Ile
            290                 295                 300

Val Ser Lys Thr Lys Asp Leu Ser Gln Asp Asp Cys Cys
305                 310                 315

<210> SEQ ID NO 6

```
<211> LENGTH: 182
<212> TYPE: PRT
<213> ORGANISM: E. coli K12 MG1655

<400> SEQUENCE: 6

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

Thr Arg Arg Ala Leu Ser Lys Lys Ala Trp Pro Gly Val Trp Thr Asn
50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 7
<211> LENGTH: 307
<212> TYPE: PRT
<213> ORGANISM: Pantoea agglomerans

<400> SEQUENCE: 7

Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
        35                  40                  45

Ala Pro Gly Lys Arg Ile Arg Pro Leu Leu Met Leu Leu Ala Ala Arg
    50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Ala Thr Gly Asp Leu Pro Gly Glu Arg
    130                 135                 140

Arg Ala Gln Ala Val Asn Glu Leu Ser Thr Ala Val Gly Val Gln Gly
145                 150                 155                 160
```

```
Leu Val Leu Gly Gln Phe Arg Asp Leu Asn Asp Ala Ala Leu Asp Arg
            165                 170                 175

Thr Pro Asp Ala Ile Leu Ser Thr Asn His Leu Lys Thr Gly Ile Leu
        180                 185                 190

Phe Ser Ala Met Leu Gln Ile Val Ala Ile Ala Ser Ala Ser Ser Pro
    195                 200                 205

Ser Thr Arg Glu Thr Leu His Ala Phe Ala Leu Asp Phe Gly Gln Ala
210                 215                 220

Phe Gln Leu Leu Asp Asp Leu Arg Asp Asp His Pro Glu Thr Gly Lys
225                 230                 235                 240

Asp Arg Asn Lys Asp Ala Gly Lys Ser Thr Leu Val Asn Arg Leu Gly
            245                 250                 255

Ala Asp Ala Ala Arg Gln Lys Leu Arg Glu His Ile Asp Ser Ala Asp
        260                 265                 270

Lys His Leu Thr Phe Ala Cys Pro Gln Gly Gly Ala Ile Arg Gln Phe
    275                 280                 285

Met His Leu Trp Phe Gly His His Leu Ala Asp Trp Ser Pro Val Met
290                 295                 300

Lys Ile Ala
305

<210> SEQ ID NO 8
<211> LENGTH: 309
<212> TYPE: PRT
<213> ORGANISM: Pantoea agglomerans

<400> SEQUENCE: 8

Met Ser Gln Pro Pro Leu Leu Asp His Ala Thr Gln Thr Met Ala Asn
1               5                   10                  15

Gly Ser Lys Ser Phe Ala Thr Ala Lys Leu Phe Asp Pro Ala Thr
            20                  25                  30

Arg Arg Ser Val Leu Met Leu Tyr Thr Trp Cys Arg His Cys Asp Asp
        35                  40                  45

Val Ile Asp Asp Gln Thr His Gly Phe Ala Ser Glu Ala Ala Ala Glu
    50                  55                  60

Glu Glu Ala Thr Gln Arg Leu Ala Arg Leu Arg Thr Leu Thr Leu Ala
65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
            100                 105                 110

Leu Asp Gly Phe Ala Met Asp Val Ala Gln Thr Arg Tyr Val Thr Phe
        115                 120                 125

Glu Asp Thr Leu Arg Tyr Cys Tyr His Val Ala Gly Val Val Gly Leu
    130                 135                 140

Met Met Ala Arg Val Met Gly Val Arg Asp Glu Arg Val Leu Asp Arg
145                 150                 155                 160

Ala Cys Asp Leu Gly Leu Ala Phe Gln Leu Thr Asn Ile Ala Arg Asp
                165                 170                 175

Ile Ile Asp Asp Ala Ala Ile Asp Arg Cys Tyr Leu Pro Ala Glu Trp
            180                 185                 190

Leu Gln Asp Ala Gly Leu Thr Pro Glu Asn Tyr Ala Ala Arg Glu Asn
        195                 200                 205

Arg Ala Ala Leu Ala Arg Val Ala Glu Arg Leu Ile Asp Ala Ala Glu
```

```
            210                 215                 220
Pro Tyr Tyr Ile Ser Ser Gln Ala Gly Leu His Asp Leu Pro Pro Arg
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
                260                 265                 270

Thr Ser Lys Gly Glu Lys Ile Ala Met Leu Met Ala Ala Pro Gly Gln
            275                 280                 285

Val Ile Arg Ala Lys Thr Thr Arg Val Thr Pro Arg Pro Ala Gly Leu
        290                 295                 300

Trp Gln Arg Pro Val
305

<210> SEQ ID NO 9
<211> LENGTH: 486
<212> TYPE: PRT
<213> ORGANISM: Pantoea agglomerans

<400> SEQUENCE: 9

Met Lys Lys Thr Val Val Ile Gly Ala Gly Phe Gly Gly Leu Ala Leu
1               5                   10                  15

Ala Ile Arg Leu Gln Ala Ala Gly Ile Pro Thr Val Leu Leu Glu Gln
                20                  25                  30

Arg Asp Lys Pro Gly Gly Arg Ala Tyr Val Trp His Asp Gln Gly Phe
            35                  40                  45

Thr Phe Asp Ala Gly Pro Thr Val Ile Thr Asp Pro Thr Ala Leu Glu
        50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Ala Glu Leu Glu Ala Gln Ile Thr Gln
                100                 105                 110

Phe Asn Pro Arg Asp Val Glu Gly Tyr Arg Arg Phe Leu Ala Tyr Ser
            115                 120                 125

Gln Ala Val Phe Gln Glu Gly Tyr Leu Arg Leu Gly Ser Val Pro Phe
        130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
                165                 170                 175

Glu His Leu Arg Gln Ala Phe Ser Phe His Ser Leu Leu Val Gly Gly
                180                 185                 190

Asn Pro Phe Thr Thr Ser Ser Ile Tyr Thr Leu Ile His Ala Leu Glu
            195                 200                 205

Arg Glu Trp Gly Val Trp Phe Pro Glu Gly Gly Thr Gly Ala Leu Val
        210                 215                 220

Asn Gly Met Val Lys Leu Phe Thr Asp Leu Gly Gly Glu Ile Glu Leu
225                 230                 235                 240

Asn Ala Arg Val Glu Glu Leu Val Val Ala Asp Asn Arg Val Ser Gln
                245                 250                 255

Val Arg Leu Ala Asp Gly Arg Ile Phe Asp Thr Asp Ala Val Ala Ser
                260                 265                 270
```

```
Asn Ala Asp Val Val Asn Thr Tyr Lys Lys Leu Leu Gly His His Pro
            275                 280                 285

Val Gly Gln Lys Arg Ala Ala Leu Glu Arg Lys Ser Met Ser Asn
290                 295                 300

Ser Leu Phe Val Leu Tyr Phe Gly Leu Asn Gln Pro His Ser Gln Leu
305                 310                 315                 320

Ala His His Thr Ile Cys Phe Gly Pro Arg Tyr Arg Glu Leu Ile Asp
            325                 330                 335

Glu Ile Phe Thr Gly Ser Ala Leu Ala Asp Asp Phe Ser Leu Tyr Leu
            340                 345                 350

His Ser Pro Cys Val Thr Asp Pro Ser Leu Ala Pro Pro Gly Cys Ala
            355                 360                 365

Ser Phe Tyr Val Leu Ala Pro Val Pro His Leu Gly Asn Ala Pro Leu
370                 375                 380

Asp Trp Ala Gln Glu Gly Pro Lys Leu Arg Asp Arg Ile Phe Asp Tyr
385                 390                 395                 400

Leu Glu Glu Arg Tyr Met Pro Gly Leu Arg Ser Gln Leu Val Thr Gln
                405                 410                 415

Arg Ile Phe Thr Pro Ala Asp Phe His Asp Thr Leu Asp Ala His Leu
            420                 425                 430

Gly Ser Ala Phe Ser Ile Glu Pro Leu Leu Thr Gln Ser Ala Trp Phe
            435                 440                 445

Arg Pro His Asn Arg Asp Ser Asp Ile Ala Asn Leu Tyr Leu Val Gly
            450                 455                 460

Ala Gly Thr His Pro Gly Ala Gly Ile Pro Gly Val Val Ala Ser Ala
465                 470                 475                 480

Lys Ala Thr Ala Ser Leu
                485

<210> SEQ ID NO 10
<211> LENGTH: 382
<212> TYPE: PRT
<213> ORGANISM: Pantoea ananatis

<400> SEQUENCE: 10

Met Gln Pro His Tyr Asp Leu Ile Leu Val Gly Ala Gly Leu Ala Asn
1               5                   10                  15

Gly Leu Ile Ala Leu Arg Leu Gln Gln Gln Pro Asp Met Arg Ile
            20                  25                  30

Leu Leu Ile Asp Ala Ala Pro Gln Ala Gly Gly Asn His Thr Trp Ser
            35                  40                  45

Phe His His Asp Asp Leu Thr Glu Ser Gln His Arg Trp Ile Ala Pro
    50                  55                  60

Leu Val Val His His Trp Pro Asp Tyr Gln Val Arg Phe Pro Thr Arg
65                  70                  75                  80

Arg Arg Lys Leu Asn Ser Gly Tyr Phe Cys Ile Thr Ser Gln Arg Phe
                85                  90                  95

Ala Glu Val Leu Gln Arg Gln Phe Gly Pro His Leu Trp Met Asp Thr
            100                 105                 110

Ala Val Ala Glu Val Asn Ala Glu Ser Val Arg Leu Lys Lys Gly Gln
            115                 120                 125

Val Ile Gly Ala Arg Ala Val Ile Asp Gly Arg Gly Tyr Ala Ala Asn
            130                 135                 140

Ser Ala Leu Ser Val Gly Phe Gln Ala Phe Ile Gly Gln Glu Trp Arg
145                 150                 155                 160
```

```
Leu Ser His Pro His Gly Leu Ser Ser Pro Ile Ile Met Asp Ala Thr
            165                 170                 175

Val Asp Gln Gln Asn Gly Tyr Arg Phe Val Tyr Ser Leu Pro Leu Ser
        180                 185                 190

Pro Thr Arg Leu Leu Ile Glu Asp Thr His Tyr Ile Asp Asn Ala Thr
    195                 200                 205

Leu Asp Pro Glu Cys Ala Arg Gln Asn Ile Cys Asp Tyr Ala Ala Gln
210                 215                 220

Gln Gly Trp Gln Leu Gln Thr Leu Leu Arg Glu Gln Gly Ala Leu
225                 230                 235                 240

Pro Ile Thr Leu Ser Gly Asn Ala Asp Ala Phe Trp Gln Gln Arg Pro
                245                 250                 255

Leu Ala Cys Ser Gly Leu Arg Ala Gly Leu Phe His Pro Thr Thr Gly
            260                 265                 270

Tyr Ser Leu Pro Leu Ala Val Ala Val Ala Asp Arg Leu Ser Ala Leu
        275                 280                 285

Asp Val Phe Thr Ser Ala Ser Ile His His Ala Ile Thr His Phe Ala
    290                 295                 300

Arg Glu Arg Trp Gln Gln Gln Gly Phe Phe Arg Met Leu Asn Arg Met
305                 310                 315                 320

Leu Phe Leu Ala Gly Pro Ala Asp Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Leu Thr Asp Arg Leu Arg Ile Leu Ser Gly Lys Pro Pro Val
        355                 360                 365

Pro Val Leu Ala Ala Leu Gln Ala Ile Met Thr Thr His Arg
    370                 375                 380

<210> SEQ ID NO 11
<211> LENGTH: 620
<212> TYPE: PRT
<213> ORGANISM: E. coli K12 MG1655

<400> SEQUENCE: 11

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
```

```
            145                 150                 155                 160
        Phe Glu Ala Met Asn His Ala Gly Asp Ile Arg Pro Asp Met Leu Val
                        165                 170                 175

Ile Leu Asn Asp Asn Glu Met Ser Ile Ser Glu Asn Val Gly Ala Leu
                        180                 185                 190

Asn Asn His Leu Ala Gln Leu Leu Ser Gly Lys Leu Tyr Ser Ser Leu
                        195                 200                 205

Arg Glu Gly Gly Lys Lys Val Phe Ser Gly Val Pro Pro Ile Lys Glu
                        210                 215                 220

Leu Leu Lys Arg Thr Glu Glu His Ile Lys Gly Met Val Val Pro Gly
        225                 230                 235                 240

Thr Leu Phe Glu Glu Leu Gly Phe Asn Tyr Ile Gly Pro Val Asp Gly
                        245                 250                 255

His Asp Val Leu Gly Leu Ile Thr Thr Leu Lys Asn Met Arg Asp Leu
                        260                 265                 270

Lys Gly Pro Gln Phe Leu His Ile Met Thr Lys Lys Gly Arg Gly Tyr
                        275                 280                 285

Glu Pro Ala Glu Lys Asp Pro Ile Thr Phe His Ala Val Pro Lys Phe
                        290                 295                 300

Asp Pro Ser Ser Gly Cys Leu Pro Lys Ser Ser Gly Gly Leu Pro Ser
        305                 310                 315                 320

Tyr Ser Lys Ile Phe Gly Asp Trp Leu Cys Glu Thr Ala Ala Lys Asp
                        325                 330                 335

Asn Lys Leu Met Ala Ile Thr Pro Ala Met Arg Glu Gly Ser Gly Met
                        340                 345                 350

Val Glu Phe Ser Arg Lys Phe Pro Asp Arg Tyr Phe Asp Val Ala Ile
                        355                 360                 365

Ala Glu Gln His Ala Val Thr Phe Ala Ala Gly Leu Ala Ile Gly Gly
                        370                 375                 380

Tyr Lys Pro Ile Val Ala Ile Tyr Ser Thr Phe Leu Gln Arg Ala Tyr
        385                 390                 395                 400

Asp Gln Val Leu His Asp Val Ala Ile Gln Lys Leu Pro Val Leu Phe
                        405                 410                 415

Ala Ile Asp Arg Ala Gly Ile Val Gly Ala Asp Gly Gln Thr His Gln
                        420                 425                 430

Gly Ala Phe Asp Leu Ser Tyr Leu Arg Cys Ile Pro Glu Met Val Ile
                        435                 440                 445

Met Thr Pro Ser Asp Glu Asn Glu Cys Arg Gln Met Leu Tyr Thr Gly
        450                 455                 460

Tyr His Tyr Asn Asp Gly Pro Ser Ala Val Arg Tyr Pro Arg Gly Asn
        465                 470                 475                 480

Ala Val Gly Val Glu Leu Thr Pro Leu Glu Lys Leu Pro Ile Gly Lys
                        485                 490                 495

Gly Ile Val Lys Arg Arg Gly Glu Lys Leu Ala Ile Leu Asn Phe Gly
                        500                 505                 510

Thr Leu Met Pro Glu Ala Ala Lys Val Ala Glu Ser Leu Asn Ala Thr
                        515                 520                 525

Leu Val Asp Met Arg Phe Val Lys Pro Leu Asp Glu Ala Leu Ile Leu
                        530                 535                 540

Glu Met Ala Ala Ser His Glu Ala Leu Val Thr Val Glu Glu Asn Ala
        545                 550                 555                 560

Ile Met Gly Gly Ala Gly Ser Gly Val Asn Glu Val Leu Met Ala His
                        565                 570                 575
```

```
Arg Lys Pro Val Pro Val Leu Asn Ile Gly Leu Pro Asp Phe Phe Ile
        580                 585                 590

Pro Gln Gly Thr Gln Glu Glu Met Arg Ala Glu Leu Gly Leu Asp Ala
        595                 600                 605

Ala Gly Met Glu Ala Lys Ile Lys Ala Trp Leu Ala
        610                 615                 620

<210> SEQ ID NO 12
<211> LENGTH: 305
<212> TYPE: PRT
<213> ORGANISM: Haematococcus pluvialis

<400> SEQUENCE: 12

Met Leu Arg Ser Leu Leu Arg Gly Leu Thr His Ile Pro Arg Val Asn
1               5                   10                  15

Ser Ala Gln Gln Pro Ser Cys Ala His Ala Arg Leu Gln Phe Lys Leu
            20                  25                  30

Arg Ser Met Gln Met Thr Leu Met Gln Pro Ser Ile Ser Ala Asn Leu
        35                  40                  45

Ser Arg Ala Glu Asp Arg Thr Asp His Met Arg Gly Ala Ser Thr Trp
    50                  55                  60

Ala Gly Gly Gln Ser Gln Asp Glu Leu Met Leu Lys Asp Glu Cys Ile
65                  70                  75                  80

Leu Val Asp Val Glu Asp Asn Ile Thr Gly His Ala Ser Lys Leu Glu
                85                  90                  95

Cys His Lys Phe Leu Pro His Gln Pro Ala Gly Leu Leu His Arg Ala
            100                 105                 110

Phe Ser Val Phe Leu Phe Asp Asp Gln Gly Arg Leu Leu Leu Gln Gln
        115                 120                 125

Arg Ala Arg Ser Lys Ile Thr Phe Pro Ser Val Trp Thr Asn Thr Cys
    130                 135                 140

Cys Ser His Pro Leu His Gly Gln Thr Pro Asp Glu Val Asp Gln Leu
145                 150                 155                 160

Ser Gln Val Ala Asp Gly Thr Val Pro Gly Ala Lys Ala Ala Ala Ile
                165                 170                 175

Arg Lys Leu Glu His Glu Leu Gly Ile Pro Ala His Gln Leu Pro Ala
            180                 185                 190

Ser Ala Phe Arg Phe Leu Thr Arg Leu His Tyr Cys Ala Ala Asp Val
        195                 200                 205

Gln Pro Ala Ala Thr Gln Ser Ala Leu Trp Gly Glu His Glu Met Asp
    210                 215                 220

Tyr Ile Leu Phe Ile Arg Ala Asn Val Thr Leu Ala Pro Asn Pro Asp
225                 230                 235                 240

Glu Val Asp Glu Val Arg Tyr Val Thr Gln Glu Leu Arg Gln Met
                245                 250                 255

Met Gln Pro Asp Asn Gly Leu Gln Trp Ser Pro Trp Phe Arg Ile Ile
            260                 265                 270

Ala Ala Arg Phe Leu Glu Arg Trp Ala Asp Leu Asp Ala Ala Leu
        275                 280                 285

Asn Thr Asp Lys His Glu Asp Trp Gly Thr Val His His Ile Asn Glu
    290                 295                 300

Ala
305
```

<210> SEQ ID NO 13
<211> LENGTH: 275
<212> TYPE: PRT
<213> ORGANISM: Uncultured marine bacterium 66A03

<400> SEQUENCE: 13

Met Gly Leu Met Leu Ile Asp Trp Cys Ala Leu Ala Leu Val Val Phe
1               5                   10                  15

Ile Gly Leu Pro His Gly Ala Leu Asp Ala Ala Ile Ser Phe Ser Met
            20                  25                  30

Ile Ser Ser Ala Lys Arg Ile Ala Arg Leu Ala Gly Ile Leu Leu Ile
        35                  40                  45

Tyr Leu Leu Leu Ala Thr Ala Phe Phe Leu Ile Trp Tyr Gln Leu Pro
    50                  55                  60

Ala Phe Ser Leu Leu Ile Phe Leu Leu Ile Ser Ile Ile His Phe Gly
65                  70                  75                  80

Met Ala Asp Phe Asn Ala Ser Pro Ser Lys Leu Lys Trp Pro His Ile
                85                  90                  95

Ile Ala His Gly Gly Val Val Thr Val Trp Leu Pro Leu Ile Gln Lys
            100                 105                 110

Asn Glu Val Thr Lys Leu Phe Ser Ile Leu Thr Asn Gly Pro Thr Pro
        115                 120                 125

Ile Leu Trp Asp Ile Leu Leu Ile Phe Phe Leu Cys Trp Ser Ile Gly
    130                 135                 140

Val Cys Leu His Thr Tyr Glu Thr Leu Arg Ser Lys His Tyr Asn Ile
145                 150                 155                 160

Ala Phe Glu Leu Ile Gly Leu Ile Phe Leu Ala Trp Tyr Ala Pro Pro
                165                 170                 175

Leu Val Thr Phe Ala Thr Tyr Phe Cys Phe Ile His Ser Arg Arg His
            180                 185                 190

Phe Ser Phe Val Trp Lys Gln Leu Gln His Met Ser Ser Lys Lys Met
        195                 200                 205

Met Ile Gly Ser Ala Ile Ile Leu Ser Cys Thr Ser Trp Leu Ile Gly
    210                 215                 220

Gly Gly Ile Tyr Phe Phe Leu Asn Ser Lys Met Ile Ala Ser Glu Ala
225                 230                 235                 240

Ala Leu Gln Thr Val Phe Ile Gly Leu Ala Ala Leu Thr Val Pro His
                245                 250                 255

Met Ile Leu Ile Asp Phe Ile Phe Arg Pro His Ser Ser Arg Ile Lys
            260                 265                 270

Ile Lys Asn
        275

<210> SEQ ID NO 14
<211> LENGTH: 566
<212> TYPE: PRT
<213> ORGANISM: Mus musculus

<400> SEQUENCE: 14

Met Glu Ile Ile Phe Gly Gln Asn Lys Lys Glu Gln Leu Glu Pro Val
1               5                   10                  15

Gln Ala Lys Val Thr Gly Ser Ile Pro Ala Trp Leu Gln Gly Thr Leu
            20                  25                  30

Leu Arg Asn Gly Pro Gly Met His Thr Val Gly Glu Ser Lys Tyr Asn
        35                  40                  45

His Trp Phe Asp Gly Leu Ala Leu Leu His Ser Phe Ser Ile Arg Asp

```
             50                  55                  60
Gly Glu Val Phe Tyr Arg Ser Lys Tyr Leu Gln Ser Asp Thr Tyr Ile
 65                  70                  75                  80

Ala Asn Ile Glu Ala Asn Arg Ile Val Val Ser Glu Phe Gly Thr Met
                 85                  90                  95

Ala Tyr Pro Asp Pro Cys Lys Asn Ile Phe Ser Lys Ala Phe Ser Tyr
                100                 105                 110

Leu Ser His Thr Ile Pro Asp Phe Thr Asp Asn Cys Leu Ile Asn Ile
                115                 120                 125

Met Lys Cys Gly Glu Asp Phe Tyr Ala Thr Thr Glu Thr Asn Tyr Ile
130                 135                 140

Arg Lys Ile Asp Pro Gln Thr Leu Glu Thr Leu Glu Lys Val Asp Tyr
145                 150                 155                 160

Arg Lys Tyr Val Ala Val Asn Leu Ala Thr Ser His Pro His Tyr Asp
                165                 170                 175

Glu Ala Gly Asn Val Leu Asn Met Gly Thr Ser Val Val Asp Lys Gly
                180                 185                 190

Arg Thr Lys Tyr Val Ile Phe Lys Ile Pro Ala Thr Val Pro Asp Ser
                195                 200                 205

Lys Lys Gly Lys Ser Pro Val Lys His Ala Glu Val Phe Cys Ser
210                 215                 220

Ile Ser Ser Arg Ser Leu Leu Ser Pro Ser Tyr Tyr His Ser Phe Gly
225                 230                 235                 240

Val Thr Glu Asn Tyr Val Val Phe Leu Glu Gln Pro Phe Lys Leu Asp
                245                 250                 255

Ile Leu Lys Met Ala Thr Ala Tyr Met Arg Gly Val Ser Trp Ala Ser
                260                 265                 270

Cys Met Ser Phe Asp Arg Glu Asp Lys Thr Tyr Ile His Ile Ile Asp
                275                 280                 285

Gln Arg Thr Arg Lys Pro Val Pro Thr Lys Phe Tyr Thr Asp Pro Met
290                 295                 300

Val Val Phe His His Val Asn Ala Tyr Glu Glu Asp Gly Cys Val Leu
305                 310                 315                 320

Phe Asp Val Ile Ala Tyr Glu Asp Ser Ser Leu Tyr Gln Leu Phe Tyr
                325                 330                 335

Leu Ala Asn Leu Asn Lys Asp Phe Glu Glu Lys Ser Arg Leu Thr Ser
                340                 345                 350

Val Pro Thr Leu Arg Arg Phe Ala Val Pro Leu His Val Asp Lys Asp
                355                 360                 365

Ala Glu Val Gly Ser Asn Leu Val Lys Val Ser Ser Thr Thr Ala Thr
                370                 375                 380

Ala Leu Lys Glu Lys Asp Gly His Val Tyr Cys Gln Pro Glu Val Leu
385                 390                 395                 400

Tyr Glu Gly Leu Glu Leu Pro Arg Ile Asn Tyr Ala Tyr Asn Gly Lys
                405                 410                 415

Pro Tyr Arg Tyr Ile Phe Ala Ala Glu Val Gln Trp Ser Pro Val Pro
                420                 425                 430

Thr Lys Ile Leu Lys Tyr Asp Ile Leu Thr Lys Ser Ser Leu Lys Trp
                435                 440                 445

Ser Glu Glu Ser Cys Trp Pro Ala Glu Pro Leu Phe Val Pro Thr Pro
450                 455                 460

Gly Ala Lys Asp Glu Asp Asp Gly Val Ile Leu Ser Ala Ile Val Ser
465                 470                 475                 480
```

```
Thr Asp Pro Gln Lys Leu Pro Phe Leu Leu Ile Leu Asp Ala Lys Ser
            485                 490                 495

Phe Thr Glu Leu Ala Arg Ala Ser Val Asp Ala Asp Met His Leu Asp
            500                 505                 510

Leu His Gly Leu Phe Ile Pro Asp Ala Asp Trp Asn Ala Val Lys Gln
            515                 520                 525

Thr Pro Ala Glu Thr Gln Glu Val Glu Asn Ser Asp His Pro Thr Asp
            530                 535                 540

Pro Thr Ala Pro Glu Leu Ser His Ser Glu Asn Asp Phe Thr Ala Gly
545                 550                 555                 560

His Gly Gly Ser Ser Leu
                565

<210> SEQ ID NO 15
<211> LENGTH: 350
<212> TYPE: PRT
<213> ORGANISM: Natronomonas pharaonis ATCC35678

<400> SEQUENCE: 15

Met Ser Asn Ala Ser Leu Arg Pro Ser Gly Thr Ala Ser Ala Thr Leu
1               5                   10                  15

Phe Arg Leu Ala Phe Leu Pro Gly Trp Ala Val Ile Ala Ala Thr Thr
            20                  25                  30

Gly Ala Phe Leu Val Gly Ala Ser Leu Pro Leu Thr Tyr Gln Leu Ile
            35                  40                  45

Pro Leu Ala Ala Ser Val Val Leu Leu Gly Leu Pro His Gly Ala Val
        50                  55                  60

Asp His Leu Ala Leu Pro Arg Thr Arg Asn Glu Arg Val Thr Val Arg
65                  70                  75                  80

Trp Leu Ala Ala Ile Gly Val Leu Tyr Ala Val Val Gly Gly Leu Tyr
                85                  90                  95

Ala Ala Val Trp Phe Leu Ala Pro Val Gly Ala Val Ala Ala Phe Ile
            100                 105                 110

Phe Met Thr Trp Val His Trp Gly Gln Gly Glu Ile Tyr Pro Leu Val
            115                 120                 125

Ala Leu Ala Asp Ala Asp His Leu Asp Gly Arg Leu Glu Arg Gly Leu
        130                 135                 140

Thr Ala Ala Ile Arg Gly Ala Leu Pro Met Leu Val Pro Phe Val Ala
145                 150                 155                 160

Phe Pro Asp Gln Tyr Glu Leu Val Val Thr Thr Leu Val Gly Leu Phe
                165                 170                 175

Asp Ala Asp Ala Ala Thr Ala Ala Ala Phe Thr Pro Thr Ala
            180                 185                 190

Arg Leu Ala Val Ala Val Thr Val Gly Gly Leu Val Ala Val Thr Leu
            195                 200                 205

Gly Ile Gly Ala Val Ala Ser Glu Thr Gly Trp Gly Pro Trp Leu
        210                 215                 220

Leu Asp Ala Gly Glu Thr Gly Leu Leu Ile Leu Phe Ala Ala Val
225                 230                 235                 240

Pro Pro Ile Phe Ala Ile Gly Leu Tyr Phe Cys Phe Trp His Ser Leu
                245                 250                 255

Arg His Ile Val Arg Leu Leu Ala Val Asp Asn Arg Ala Ala Pro Ala
            260                 265                 270

Leu Asp Gly Arg Arg Tyr Gly Ala Ala Leu Ala Arg Phe Ala Arg Asp
```

```
            275                 280                 285
Ala Ala Pro Leu Ser Ala Ser Leu Val Leu Gly Leu Leu Tyr
    290                 295                 300

Leu Ala Val Pro Gly Ser Val Asp Ser Pro Leu Ser Leu Val Gly Thr
305                 310                 315                 320

Tyr Leu Val Leu Ile Ala Val Leu Thr Leu Pro His Val Val Val
                325                 330                 335

Ala Trp Met Asp His Glu Gln Arg Leu Trp Arg Pro Gly Ala
        340                 345                 350

<210> SEQ ID NO 16
<211> LENGTH: 284
<212> TYPE: PRT
<213> ORGANISM: Halobacterium salinarum ATCC700922

<400> SEQUENCE: 16

Met Pro His Gly Ala Ile Asp Tyr Leu Ala Leu Pro Arg Ala Val Thr
1               5                   10                  15

Gly Thr Val Thr Val Arg Trp Leu Ala Val Val Gly Val Leu Tyr Leu
                20                  25                  30

Val Leu Gly Gly Gly Tyr Ala Ala Ala Trp Phe Phe Ala Pro Val Pro
            35                  40                  45

Ala Ala Phe Ala Phe Val Ala Ile Thr Trp Leu His Trp Gly Gln Gly
        50                  55                  60

Asp Leu Tyr Pro Leu Leu Asp Phe Leu Asp Val Asp Tyr Leu Asp Thr
65                  70                  75                  80

Arg Pro Arg Arg Ala Ala Thr Val Leu Ile Arg Gly Gly Leu Pro Met
                85                  90                  95

Leu Val Pro Leu Leu Gly Phe Pro Glu Arg Tyr Arg Ser Val Val Asp
            100                 105                 110

Ala Phe Ala Ala Pro Phe Gly Gly Ser Val Gly Asp Leu Ala Val Phe
        115                 120                 125

Asp Pro Arg Val Arg Leu Trp Leu Gly Val Ala Phe Ala Ala Ala Thr
130                 135                 140

Val Ala Val Leu Ala Ala Gly Arg Arg Arg Thr His Ser Pro Gly Ala
145                 150                 155                 160

Trp Arg Val Asp Ala Ala Glu Thr Leu Leu Leu Trp Val Phe Phe Phe
                165                 170                 175

Val Val Pro Pro Val Phe Ala Val Gly Val Tyr Phe Cys Val Trp His
            180                 185                 190

Ser Val Arg His Val Ala Arg Ala Ile Ala Val Asp Gly Ser Val His
        195                 200                 205

Pro Ser Leu Arg Ala Gly Asp Ile Leu Gly Pro Leu Ala Arg Phe Gly
210                 215                 220

Val Glu Ala Ala Pro Met Thr Ala Ala Leu Ala Leu Gly Gly Val
225                 230                 235                 240

Leu Trp Trp Ala Val Pro Asn Pro Pro Thr Thr Leu Glu Ser Gly Ala
                245                 250                 255

Ala Leu Tyr Leu Val Leu Ile Ala Val Leu Thr Leu Pro His Val Ala
            260                 265                 270

Val Val Thr Trp Met Asp Arg Val Gln Gly Val Leu
        275                 280

<210> SEQ ID NO 17
<211> LENGTH: 284
```

```
<212> TYPE: PRT
<213> ORGANISM: Halobacterium salinarum ATCC700922

<400> SEQUENCE: 17

Met Pro His Gly Ala Ile Asp Tyr Leu Ala Leu Pro Arg Ala Val Thr
1               5                   10                  15

Gly Thr Val Thr Val Arg Trp Leu Ala Val Val Gly Val Leu Tyr Leu
                20                  25                  30

Val Leu Gly Gly Gly Tyr Ala Ala Ala Trp Phe Phe Ala Pro Val Pro
            35                  40                  45

Ala Ala Phe Ala Phe Val Ala Ile Thr Trp Leu His Trp Gly Gln Gly
        50                  55                  60

Asp Leu Tyr Pro Leu Leu Asp Phe Leu Asp Val Asp Tyr Leu Asp Thr
65                  70                  75                  80

Arg Pro Arg Arg Ala Ala Thr Val Leu Ile Arg Gly Gly Leu Pro Met
                85                  90                  95

Leu Val Pro Leu Leu Gly Phe Pro Glu Arg Tyr Arg Ser Val Val Asp
            100                 105                 110

Ala Phe Ala Ala Pro Phe Gly Gly Ser Val Gly Asp Leu Ala Val Phe
        115                 120                 125

Asp Pro Arg Val Arg Leu Trp Leu Gly Val Ala Phe Ala Ala Ala Thr
130                 135                 140

Val Ala Val Leu Ala Ala Gly Arg Arg Arg Thr His Ser Pro Gly Ala
145                 150                 155                 160

Trp Arg Val Asp Ala Ala Glu Thr Leu Leu Leu Trp Val Phe Phe Phe
                165                 170                 175

Val Val Pro Pro Val Phe Ala Val Gly Val Tyr Phe Cys Val Trp His
            180                 185                 190

Ser Val Arg His Val Ala Arg Ala Ile Ala Val Asp Gly Ser Val His
        195                 200                 205

Pro Ser Leu Arg Ala Gly Asp Ile Leu Gly Pro Leu Ala Arg Phe Gly
210                 215                 220

Val Glu Ala Ala Pro Met Thr Ala Ala Ala Leu Ala Leu Gly Gly Val
225                 230                 235                 240

Leu Trp Trp Ala Val Pro Asn Pro Pro Thr Thr Leu Glu Ser Gly Ala
                245                 250                 255

Ala Leu Tyr Leu Val Leu Ile Ala Val Leu Thr Leu Pro His Val Ala
            260                 265                 270

Val Val Thr Trp Met Asp Arg Val Gln Gly Val Leu
        275                 280

<210> SEQ ID NO 18
<211> LENGTH: 2412
<212> TYPE: DNA
<213> ORGANISM: Enterococcus faecalis

<400> SEQUENCE: 18
ttgaaaacag tagttattat tgatgcatta cgaacaccaa ttggaaaata taaaggcagc    60
ttaagtcaag taagtgccgt agacttagga acacatgtta caacacaact ttttaaaaga   120
cattccacta tttctgaaga aattgatcaa gtaatctttg gaaatgtttt acaagctgga   180
aatggccaaa atcccgcacg acaaatagca ataaacagcg gttatctctc tgaaattccc   240
gcaatgacag ttaatgaggt ctgcggatca ggaatgaagg ccgttatttt ggcgaaacaa   300
ttgattcaat taggagaagc ggaagtttta attgctggcg ggattgagaa tatgtcccaa   360
```

```
gcacctaaat tacaacgatt taattacgaa acagaaagct atgatgcgcc ttttctagt      420 atgatgtacg atgggttaac ggatgccttt agtggtcaag caatgggctt aactgctgaa      480
aatgtggccg aaaagtatca tgtaactaga gaagagcaag atcaattttc tgtacattca      540
caattaaaag cagctcaagc acaagcgaaa gggatattcg ctgacgaaat agccccatta      600
gaagtatcag gaacgcttgt ggagaaagat gaagggattc gccctaattc gagcgttgag      660
aagctaggaa cgcttaaaac agttttttaaa gaagacggta ctgtaacagc agggaatgca      720
tcaaccatta tgatggggc ttctgctttg attattgctt cacaagaata tgccgaagca      780
cacggtcttc cttatttagc tattattcga gacagtgtgg aagtcggtat tgatccagcc      840
tatatgggaa tttcgccgat taaagccatt caaaaactgt tagcgcgcaa tcaacttact      900
acggaagaaa ttgatctgta tgaaatcaac gaagcatttg cagcaacttc aatcgtggtc      960
caaagagaac tggctttacc agaggaaaag gtcaacattt atggtggcgg tatttcatta    1020
ggtcatgcga ttggtgccac aggtgctcgt ttattaacga gtttaagtta tcaattaaat    1080
caaaaagaaa agaaatatgg agtggcttct ttatgtatcg gcggtggctt aggactcgct    1140
atgctactag agagacctca gcaaaaaaaa aacagccgat tttatcaaat gagtcctgag    1200
gaacgcctgg cttctcttct taatgaaggc cagatttctg ctgatacaaa aaagaatttt    1260
gaaaatacgg ctttatcttc gcagattgcc aatcatatga ttgaaaatca aatcagtgaa    1320
acagaagtgc cgatgggcgt tggcttacat ttaacagtgg acgaaactga ttatttggta    1380
ccaatggcga cagaagagcc ctcagtgatt gcggctttga gtaatggtgc aaaaatagca    1440 caaggatta aaacagtgaa tcaacaacgt ttaatgcgtg acaaatcgt tttttacgat    1500 gttgcagacg ccgagtcatt gattgatgaa ctacaagtaa gagaaacgga aattttttcaa    1560 caagcagagt taagttatcc atctatcgtt aaacgcggcg gcggcttaag agatttgcaa    1620
tatcgtgctt ttgatgaatc atttgtatct gtcgactttt tagtagatgt taaggatgca    1680
atgggggcaa atatcgttaa cgctatgttg aaggtgtgg ccgagttgtt ccgtgaatgg    1740
tttgcggagc aaaagatttt attcagtatt ttaagtaatt atgccacgga gtcggttgtt    1800
acgatgaaaa cggctattcc agtttcacgt ttaagtaagg ggagcaatgg ccgggaaatt    1860
gctgaaaaaa ttgttttagc ttcacgctat gcttcattag atccttatcg ggcagtcacg    1920
cataacaaag ggatcatgaa tggcattgaa gctgtcgttt tagctacagg aaatgataca    1980
cgcgctgtta gcgcttcttg tcatgctttt gcggtgaagg aaggtcgcta ccaaggtttg    2040
actagtggga cgctggatgg cgaacaacta attggtgaaa tttcagttcc gcttgcgtta    2100
gccacggttg gcggtgccac aaaagtctta cctaaatctc aagcagctgc tgatttgtta    2160
gcagtgacgg atgcaaaaga actaagtcga gtagtagcgg ctgttggttt ggcacaaaat    2220
ttagcggcgt tacgggcctt agtctctgaa ggaattcaaa aaggacacat ggctctacaa    2280
gcacgttctt tagcgatgac ggtcggagct actggtaaag aagttgaggc agtcgctcaa    2340
caattaaaac gtcaaaaac gatgaaccaa gaccgagcct tggctatttt aaatgattta    2400
agaaaacaat aa                                                          2412

<210> SEQ ID NO 19
<211> LENGTH: 1152
<212> TYPE: DNA
<213> ORGANISM: Enterococcus faecalis

<400> SEQUENCE: 19
atgacaattg ggattgataa aattagtttt tttgtgcccc cttattatat tgatatgacg       60
```

```
gcactggctg aagccagaaa tgtagaccct ggaaaatttc atattggtat tgggcaagac    120
caaatggcgg tgaacccaat cagccaagat attgtgacat ttgcagccaa tgccgcagaa    180
gcgatcttga ccaaagaaga taaagaggcc attgatatgg tgattgtcgg gactgagtcc    240
agtatcgatg agtcaaaagc ggccgcagtt gtcttacatc gtttaatggg gattcaacct    300
ttcgctcgct ctttcgaaat caaggaagct tgttacggag caacagcagg cttacagtta    360
gctaagaatc acgtagcctt acatccagat aaaaaagtct tggttgtagc agcagatatt    420
gcaaaatatg gattaaattc tggcggtgag cctacacaag gagctggggc ggttgcaatg    480
ttagttgcta gtgaaccgcg catcttggct ttaaaagagg ataatgtgat gctgacgcaa    540
gatatctatg acttttggcg tccaacaggc catccgtatc ctatggtcga tggtcctttg    600
tcaaacgaaa cctacatcca atcttttgcc caagtctggg atgaacataa aaaagaacc     660 ggtcttgatt ttgcagatta tgatgcttta gcgttccata ttccttacac aaaaatgggc    720 aaaaagcct tattagcaaa aatctccgac caaactgaag cagaacagga acgaatttta     780
gcccgttatg aagaaagcat catctatagt cgtcgcgtag gaaacttgta tacgggttca    840
ctttatctgg gactcatttc ccttttagaa aatgcaacga ctttaaccgc aggcaatcaa    900
attgggttat tcagttatgg ttctggtgct gtcgctgaat ttttcactgg tgaattagta    960
gctggttatc aaaatcattt acaaaaagaa actcatttag cactgctaga taatcggaca   1020
gaactttcta tcgctgaata tgaagccatg tttgcagaaa ctttagacac agatattgat   1080
caaacgttag aagatgaatt aaaatatagt atttctgcta ttaataatac cgttcgctct   1140
tatcgaaact aa                                                      1152

<210> SEQ ID NO 20
<211> LENGTH: 879
<212> TYPE: DNA
<213> ORGANISM: Streptococcus pneumoniae

<400> SEQUENCE: 20
atgacaaaaa aagttggtgt cggtcaggca catagtaaga taattttaat agggaacat      60 gcggtcgttt acggttatcc tgccattttc ctgcctcttt tggaggtgga ggtgacctgt    120
aaggtagttt ctgcagagag tccttggcgc ctttatgagg aggataccgt gtccatggcg    180
gtttatgcct cactggagta tttggatatc acagaagcct gcgttcgttg tgagattgac    240
tcggctatcc ctgagaaacg ggggatgggt tcgtcagcgg ctatcagcat agcggccatt    300
cgtgcggtat ttgactacta tcaggctgat ctgcctcatg atgtactaga aatcttggtc    360
aatcgagctg agatgattgc ccatatgaat cctagtggtt tggatgctaa gacctgtctc    420
agtgaccaac ctattcgctt tatcaagaac gtaggattta cagaacttga gatggattta    480
tccgcctatt tggtgattgc cgatacgggt gtttatggtc atactcgtga agccatccaa    540
gtggttcaaa ataagggcaa ggatgcccta ccgttttttgc atgccttggg agaattaacc    600
cagcaagcag aagttgcgat ttcacaaaaa tatgctgaag gactgggact aatcttcagt    660
caagctcatt tacatctaaa agaaattgga gtcagtagcc ctgaggcaga cttttttggtt    720 gaaacggctc ttagctatgg tgctctgggt gccaagatga gcggtggtgg gctaggaggt    780
tgtatcatag ccttggtaac caatttgacg cacgcacaag aactagcaga aagattagaa    840
gagaaaggag ctgttcagac atggatagag agcctgtaa                          879

<210> SEQ ID NO 21
```

```
<211> LENGTH: 1011
<212> TYPE: DNA
<213> ORGANISM: Streptococcus pneumoniae

<400> SEQUENCE: 21
atgattgctg ttaaaacttg cggaaaactc tattgggcag gtgaatatgc tattttagag      60
ccagggcagt tagctttgat aaaggatatt cccatctata tgagggctga gattgctttt     120
tctgacagct accgtatcta ttcagatatg tttgatttcg cagtggactt aaggcccaat     180
cctgactaca gcttgattca agaaacgatt gctttgatgg gagacttcct cgctgttcgc     240
ggtcagaatt taagaccttt ttccctaaaa atctgtggca aaatggaacg agaagggaaa     300
aagtttggtc taggttctag tggcagcgtc gttgtcttgg ttgtcaaggc tttactggct     360
ctctataatc tttcggttga tcagaatctc ttgttcaagc tgactagcgc tgtcttgctc     420
aagcgaggag acaatggttc catgggcgac cttgcctgta ttgtggcaga ggatttggtt     480
ctttaccagt catttgatcg ccagaaggcg gctgctggt tagaagaaga aaacttggcg      540
acagttctgg agcgtgattg gggattttt atctcacaag tgaaaccaac tttagaatgt      600
gatttcttag tgggatggac caaggaagtg gctgtatcga gtcacatggt ccagcaaatc     660
aagcaaaata tcaatcaaaa ttttttaagt tcctcaaaag aaacggtggt ttctttggtc     720
gaagccttgg agcaggggaa agccgaaaaa gttatcgagc aagtagaagt agccagcaag     780
cttttagaag gcttgagtac agatatttac acgcctttgc ttagacagtt gaaagaagcc     840
agtcaagatt tgcaggccgt tgccaagagt agtggtgctg gtggtggtga ctgtggcatc     900
gccctgagtt ttgatgcgca atcttctcga aacactttaa aaaatcgttg ggccgatctg     960
gggattgagc tcttatatca agaaaggata ggacatgacg acaaatcgta a              1011

<210> SEQ ID NO 22
<211> LENGTH: 954
<212> TYPE: DNA
<213> ORGANISM: Streptococcus pneumoniae

<400> SEQUENCE: 22
atggatagag agcctgtaac agtacgttcc tacgcaaata ttgctattat caaatattgg      60
ggaaagaaaa aagaaaaaga gatggtgcct gctactagca gtatttctct aactttggaa     120
aatatgtata cagagacgac cttgtcgcct ttaccagcca atgtaacagc tgacgaattt     180
tacatcaatg gtcagctaca aaatgaggtc gagcatgcca agatgagtaa gattattgac     240
cgttatcgtc cagctggtga gggctttgtc cgtatcgata ctcaaaacaa tatgcctacg     300
gcagcgggcc tgtcctcaag ttctagtggt ttgtccgccc tggtcaaggc ttgtaatgct     360
tatttcaagc ttggattgga tagaagtcag ttggcacagg aagccaaatt tgcctcaggc     420
tcttcttctc ggagttttta tggaccacta ggagcctggg ataaggatag tggagaaatt     480
taccctgtag agacagactt gaaactagct atgattatgt tggtgctaga ggacaagaaa     540
aaaccaatct ctagccgtga cgggatgaaa ctttgtgtgg aaacctcgac gacttttgac     600
gactgggttc gtcagtctga gaaggactat caggatatgc tgatttatct caaggaaaat     660
gattttgcca agattggaga attaacggag aaaaatgctc tggctatgca tgctacgaca     720
aagactgcta gtccagcctt tcttatctg acggatgcct cttatgaggc tatggccttt      780
gttcgccagc ttcgtgagaa aggagaggcc tgctacttta ccatggatgc tggtcccaat     840
gttaaggtct tctgtcagga gaagacttg gagcatttgt cagaaatttt cggtcagcgt      900
tatcgcttga ttgtgtcaaa aacaaaggat ttgagtcaag atgattgctg ttaa           954
```

<210> SEQ ID NO 23
<211> LENGTH: 546
<212> TYPE: DNA
<213> ORGANISM: E. coli K12 MG1655

<400> SEQUENCE: 23

| | | |
|---|---|---|
| atgcaaacgg aacacgtcat tttattgaat gcacagggag ttcccacggg tacgctggaa | 60 |
| aagtatgccg cacacacggc agacacccgc ttacatctcg cgttctccag ttggctgttt | 120 |
| aatgccaaag acaattatt agttacccgc cgcgcactga gcaaaaaagc atggcctggc | 180 |
| gtgtggacta actcggtttg tgggcaccca caactgggag aaagcaacga agacgcagtg | 240 |
| atccgccgtt gccgttatga gcttggcgtg gaaattacgc tcctgaatc tatctatcct | 300 |
| gactttcgct accgcgccac cgatccgagt ggcattgtgg aaaatgaagt gtgtccggta | 360 |
| tttgccgcac gcaccactag tgcgttacag atcaatgatg atgaagtgat ggattatcaa | 420 |
| tggtgtgatt tagcagatgt attacacggt attgatgcca cgccgtgggc gttcagtccg | 480 |
| tggatggtga tgcaggcgac aaatcgcgaa gccagaaaac gattatctgc atttacccag | 540 |
| cttaaa | 546 |

<210> SEQ ID NO 24
<211> LENGTH: 918
<212> TYPE: DNA
<213> ORGANISM: Haematococcus pluvialis

<400> SEQUENCE: 24

| | | |
|---|---|---|
| atgcttcgtt cgttgctcag aggcctcacg catatccccc gcgtgaactc cgcccagcag | 60 |
| cccagctgtg cacacgcgcg actccagttt aagctcagga gcatgcagat gacgctcatg | 120 |
| cagcccagca tctcagccaa tctgtcgcgc gccgaggacc gcacagacca catgaggggt | 180 |
| gcaagcacct gggcaggcgg gcagtcgcag gatgagctga tgctgaagga cgagtgcatc | 240 |
| ttggtggatg ttgaggacaa catcacaggc catgccagca agctggagtg tcacaagttc | 300 |
| ctaccacatc agcctgcagg cctgctgcac cgggccttct ctgtgttcct gtttgacgat | 360 |
| caggggcgac tgctgctgca acagcgtgca cgctcaaaaa tcaccttccc aagtgtgtgg | 420 |
| acgaacacct gctgcagcca ccctttacat gggcagaccc cagatgaggt ggaccaacta | 480 |
| agccaggtgg ccgacggaac agtacctggc gcaaaggctg ctgccatccg caagttggag | 540 |
| cacgagctgg ggataccagc gcaccagctg ccggcaagcg cgtttcgctt cctcacgcgt | 600 |
| ttgcactact gtgccgcgga cgtgcagcca gctgcgacac aatcagcgct ctggggcgag | 660 |
| cacgaaatgg actacatctt gttcatccgg gccaacgtca ccttggcgcc caaccctgac | 720 |
| gaggtggacg aagtcaggta cgtgacgcaa gaggagctgc ggcagatgat gcagccggac | 780 |
| aacgggctgc aatggtcgcc gtggtttcgc atcatcgccg cgcgcttcct tgagcgttgg | 840 |
| tgggctgacc tggacgcggc cctaaacact gacaaacacg aggattgggg aacggtgcat | 900 |
| cacatcaacg aagcgtga | 918 |

<210> SEQ ID NO 25
<211> LENGTH: 1884
<212> TYPE: DNA
<213> ORGANISM: E. coli K12 MG1655

<400> SEQUENCE: 25

| | | |
|---|---|---|
| atggaattca ggaggcccct gatgagtttt gatattgcca ataccccgac cctggcactg | 60 |

```
gtcgactcca cccaggagtt acgactgttg ccgaaagaga gtttaccgaa actctgcgac    120
gaactgcgcc gctatttact cgacagcgtg agccgttcca gcgggcactt cgcctccggg    180
ctgggcacgg tcgaactgac cgtggcgctg cactatgtct acaacacccc gtttgaccaa    240
ttgatttggg atgtggggca tcaggcttat ccgcataaaa ttttgaccgg acgccgcgac    300
aaaatcggca ccatccgtca gaaaggcggt ctgcacccgt tcccgtggcg cggcgaaagc    360
gaatatgacg tattaagcgt cgggcattca tcaacctcca tcagtgccgg aattggtatt    420
gcggttgctg ccgaaaaaga aggcaaaaat cgccgcaccg tctgtgtcat tggcgatggc    480
gcgattaccg caggcatggc gtttgaagcg atgaatcacg cgggcgatat ccgtcctgat    540
atgctggtga ttctcaacga caatgaaatg tcgatttccg aaaatgtcgg cgcgctcaac    600
aaccatctgg cacagctgct ttccggtaag ctttactctt cactgcgcga aggcgggaaa    660
aaagttttct ctggcgtgcc gccaattaaa gagctgctca aacgcaccga gaacatatt    720
aaaggcatgg tagtgcctgg cacgttgttt gaagagctgg gctttaacta catcggcccg    780
gtggacggtc acgatgtgct ggggcttatc accacgctaa agaacatgcg cgacctgaaa    840
ggcccgcagt tcctgcatat catgaccaaa aaaggtcgtg gttatgaacc ggcagaaaaa    900
gacccgatca ctttccacgc cgtgcctaaa tttgatccct ccagcggttg tttgccgaaa    960
agtagcggcg gtttgccgag ctattcaaaa atctttggcg actggttgtg cgaaacggca   1020
gcgaaagaca caagctgat ggcgattact ccggcgatgc gtgaaggttc cggcatggtc   1080
gagttttcac gtaaattccc ggatcgctac ttcgacgtgg caattgccga gcaacacgcg   1140
gtgacctttg ctgcgggtct ggcgattggt gggtacaaac ccattgtcgc gatttactcc   1200
actttcctgc aacgcgccta tgatcaggtg ctgcatgacg tggcgattca aaagcttccg   1260
gtcctgttcg ccatcgaccg cgcgggcatt gttggtgctg acggtcaaac ccatcagggt   1320
gcttttgatc tctcttacct gcgctgcata ccggaaatgg tcattatgac cccgagcgat   1380
gaaaacgaat gtcgccagat gctctatacc ggctatcact ataacgatgg cccgtcagcg   1440
gtgcgctacc gcgtggcaa cgcggtcggc gtggaactga cgccgctgga aaaactacca   1500
attggcaaag gcattgtgaa gcgtcgtggc gagaaactgg cgatccttaa ctttggtacg   1560
ctgatgccag aagcggcgaa agtcgccgaa tcgctgaacg ccacgctggt cgatatgcgt   1620
tttgtgaaac cgcttgatga agcgttaatt ctggaaatgg ccgccagcca tgaagcgctg   1680
gtcaccgtag aagaaaacgc cattatgggc ggcgcaggca gcggcgtgaa cgaagtgctg   1740
atggcccatc gtaaaccagt acccgtgctg aacattggcc tgccggactt ctttattccg   1800
caaggaactc aggaagaaat gcgcgccgaa ctcggcctcg atgccgctgg tatggaagcc   1860
aaaatcaagg cctggctggc ataa                                         1884
```

<210> SEQ ID NO 26
<211> LENGTH: 924
<212> TYPE: DNA
<213> ORGANISM: Pantoea agglomerans

<400> SEQUENCE: 26

```
atggtgagtg gcagtaaagc gggcgtttcg cctcatcgcg aaatagaagt aatgagacaa    60
tccattgacg atcacctggc tggcctgtta cctgaaaccg acagccagga tatcgtcagc   120
cttgcgatgc gtgaaggcgt catggcaccc ggtaaacgga tccgtccgct gctgatgctg   180
ctggccgccc gcgacctccg ctaccagggc agtatgccta cgctgctcga tctcgcctgc   240
gccgttgaac tgacccatac cgcgtcgctg atgctcgacg acatgccctg catggacaac   300
```

```
gccgagctgc gccgcggtca gcccactacc cacaaaaaat ttggtgagag cgtggcgatc      360
cttgcctccg ttgggctgct ctctaaagcc tttggtctga tcgccgccac cggcgatctg      420
ccgggggaga ggcgtgccca ggcggtcaac gagctctcta ccgccgtggg cgtgcagggc      480
ctggtactgg ggcagtttcg cgatcttaac gatgccgccc tcgaccgtac ccctgacgct      540
atcctcagca ccaaccacct caagaccggc attctgttca gcgcgatgct gcagatcgtc      600
gccattgctt ccgcctcgtc gccgagcacg cgagagacgc tgcacgcctt cgccctcgac      660
ttcggccagg cgtttcaact gctggacgat ctgcgtgacg atcacccgga accggtaaa       720 gatcgcaata aggacgcggg aaaatcgacg ctggtcaacc ggctgggcgc agacgcggcc      780
cggcaaaagc tgcgcgagca tattgattcc gccgacaaac acctcacttt tgcctgtccg      840
cagggcggcg ccatccgaca gtttatgcat ctgtggtttg ccatcaccct tgccgactgg      900
tcaccggtca tgaaaatcgc ctga                                            924

<210> SEQ ID NO 27
<211> LENGTH: 930
<212> TYPE: DNA
<213> ORGANISM: Pantoea agglomerans

<400> SEQUENCE: 27
atgagccaac cgccgctgct tgaccacgcc acgcagacca tggccaacgg ctcgaaaagt       60
tttgccaccg ctgcgaagct gttcgacccg gccacccgcc gtagcgtgct gatgctctac      120
acctggtgcc gccactgcga tgacgtcatt gacgaccaga cccacggctt cgccagcgag      180
gccgcggcgg aggaggaggc cacccagcgc ctggcccggc tgcgcacgct gaccctggcg      240
gcgtttgaag gggccgagat gcaggatccg gccttcgctg cctttcagga ggtggcgctg      300
acccacggta ttacgccccg catggcgctc gatcacctcg acggctttgc gatggacgtg      360
gctcagaccc gctatgtcac ctttgaggat acgctgcgct actgctatca cgtggcgggc      420
gtggtgggtc tgatgatggc cagggtgatg ggcgtgcggg atgagcgggt gctggatcgc      480
gcctgcgatc tggggctggc cttccagctg acgaatatcg cccgggatat tattgacgat      540
gcggctattg accgctgcta tctgcccgcc gagtggctgc aggatgccgg gctgaccccg      600
gagaactatg ccgcgcggga gaatcgggcc gcgctggcgc gggtggcgga gcggcttatt      660
gatgccgcag agccgtacta catctcctcc caggcccggc tacacgatct gccgccgcgc      720
tgcgcctggg cgatcgccac cgcccgcagc gtctaccggg agatcggtat taaggtaaaa      780
gcggcgggag gcagcgcctg ggatcgccgc cagcacacca gcaaaggtga aaaaattgcc      840
atgctgatgg cggcaccggg gcaggttatt cgggcgaaga cgacgagggt gacgccgcgt      900
ccggccggtc tttggcagcg tcccgtttag                                      930

<210> SEQ ID NO 28
<211> LENGTH: 1459
<212> TYPE: DNA
<213> ORGANISM: Pantoea agglomerans

<400> SEQUENCE: 28
atgaaaaaaa ccgttgtgat tggcgcaggc tttggtggcc tggcgctggc gattcgcctg       60
caggcggcag ggatcccaac cgtactgctg gagcagcggg acaagcccgg cggtcgggcc      120
tacgtctggc atgaccaggg cttttacctt tgacgccggg cgacggtgat caccgatcct      180
accgcgcttg aggcgctgtt caccctggcc ggcaggcgca tggaggatta cgtcaggctg      240
```

```
ctgccggtaa aacccttcta ccgactctgc tgggagtccg ggaagaccct cgactatgct      300
aacgacagcg ccgagcttga ggcgcagatt acccagttca accccgcga cgtcgagggc      360 taccggcgct ttctggctta ctcccaggcg gtattccagg agggatattt gcgcctcggc      420
agcgtgccgt tcctctcttt tcgcgacatg ctgcgcgccg ggccgcagct gcttaagctc      480
caggcgtggc agagcgtcta ccagtcggtt tcgcgcttta ttgaggatga gcatctgcgg      540
caggccttct cgttccactc cctgctggta ggcggcaacc ccttcaccac ctcgtccatc      600
tacaccctga tccacgccct tgagcgggag tggggggtct ggttccctga gggcggcacc      660
ggggcgctgg tgaacggcat ggtgaagctg tttaccgatc tgggcgggga gatcgaactc      720
aacgcccggg tcgaagagct ggtggtggcc gataaccgcg taagccaggt ccggctggcg      780
gatggtcgga tctttgacac cgacgccgta gcctcgaacg ctgacgtggt gaacaccctat    840 aaaaagctgc tcggccacca tccggtgggg cagaagcggg cggcagcgct ggagcgcaag    900
agcatgagca actcgctgtt tgtgctctac ttcggcctga accagcctca ttcccagctg      960
gcgcaccata ccatctgttt tggtccccgc taccggagc tgatcgacga gatctttacc      1020
ggcagcgcgc tggcggatga cttctcgctc tacctgcact cgccctgcgt gaccgatccc    1080
tcgctcgcgc ctcccggctg cgccagcttc tacgtgctgg ccccggtgcc gcatcttggc    1140
aacgcgccgc tggactgggc gcaggagggg ccgaagctgc gcgaccgcat ctttgactac    1200
cttgaagagc gctatatgcc cggcctgcgt agccagctgg tgacccagcg gatctttacc    1260
ccggcagact tccacgacac gctggatgcg catctgggat cggccttctc catcgagccg    1320
ctgctgaccc aaagcgcctg gttccgcccg cacaaccgcg acagcgacat tgccaacctc    1380
tacctggtgg gcgcaggtac tcaccctggg gcgggcattc ctggcgtagt ggcctcggcg    1440
aaagccaccg ccagcctga                                                  1459

<210> SEQ ID NO 29
<211> LENGTH: 1149
<212> TYPE: DNA
<213> ORGANISM: Pantoea ananatis

<400> SEQUENCE: 29
atgcaaccgc attatgatct gattctcgtg ggggctggac tcgcgaatgg ccttatcgcc       60
ctgcgtcttc agcagcagca acctgatatg cgtattttgc ttatcgacgc cgcaccccag     120
gcgggcggga atcatacgtg gtcatttcac cacgatgatt tgactgagag ccaacatcgt    180
tggatagctc cgctggtggt tcatcactgg cccgactatc aggtacgctt cccacacgc     240 cgtcgtaagc tgaacagcgg ctacttttgt attacttctc agcgtttcgc tgaggtttta    300
cagcgacagt ttggcccgca cttgtggatg gataccgcgg tcgcagaggt taatgcggaa    360
tctgttcggt tgaaaaaggg tcaggttatc ggtgcccgcg cggtgattga cgggcggggt    420
tatgcggcaa attcagcact gagcgtgggc ttccaggcgt ttattggcca ggaatggcga    480
ttgagccacc cgcatggttt atcgtctccc attatcatga tgccacggt cgatcagcaa    540 aatggttatc gcttcgtgta cagcctgccg ctctcgccga ccagattgtt aattgaagac    600
acgcactata ttgataatgc gacattagat cctgaatgcg cgcggcaaaa tatttgcgac    660
tatgccgcgc aacagggttg gcagcttcag acactgctgc gagaagaaca gggcgcctta    720
cccattactc tgtcgggcaa tgccgacgca ttctggcagc agcgcccct ggcctgtagt    780 ggattacgtg ccggtctgtt ccatcctacc accggctatt cactgccgct ggcggttgcc    840
gtggccgacc gcctgagtgc acttgatgtc tttacgtcgg cctcaattca ccatgccatt    900
```

```
acgcattttg cccgcgagcg ctggcagcag cagggctttt tccgcatgct gaatcgcatg    960
ctgtttttag ccggacccgc cgattcacgc tggcgggtta tgcagcgttt ttatggttta   1020
cctgaagatt taattgcccg tttttatgcg ggaaaactca cgctgaccga tcggctacgt   1080
attctgagcg gcaagccgcc tgttccggta ttagcagcat tgcaagccat tatgacgact   1140
catcgttaa                                                           1149
```

<210> SEQ ID NO 30
<211> LENGTH: 4176
<212> TYPE: DNA
<213> ORGANISM: Artificial Sequence
<220> FEATURE:
<223> OTHER INFORMATION: pTrc99A vector

<400> SEQUENCE: 30

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagaccatgg aattcgagct cggtacccgg ggatcctcta    300
gagtcgacct gcaggcatgc aagcttggct gttttggcgg atgagagaag attttcagcc    360
tgatacagat taaatcagaa cgcagaagcg gtctgataaa acagaatttg cctggcggca    420
gtagcgcggt ggtcccacct gacccccatgc cgaactcaga agtgaaacgc cgtagcgccg    480
atggtagtgt ggggtctccc catgcgagag tagggaactg ccaggcatca aataaaacga    540
aaggctcagt cgaaagactg ggcctttcgt tttatctgtt gtttgtcggt gaacgctctc    600
ctgagtagga caaatccgcc gggagcggat ttgaacgttg cgaagcaacg gcccggaggg    660
tggcgggcag gacgcccgcc ataaactgcc aggcatcaaa ttaagcagaa ggccatcctg    720
acggatggcc ttttttgcgtt tctacaaact cttttttgttt attttttctaa atacattcaa    780 atatgtatcc gctcatgaga caataaccct gataaatgct tcaataatat tgaaaaagga    840
agagtatgag tattcaacat ttccgtgtcg cccttattcc cttttttgcg gcattttgcc    900
ttcctgtttt tgctcaccca gaaacgctgg tgaaagtaaa agatgctgaa gatcagttgg    960
gtgcacgagt gggttacatc gaactggatc tcaacagcgg taagatcctt gagagttttc   1020
gccccgaaga acgttttcca atgatgagca cttttaaagt tctgctatgt ggcgcggtat   1080
tatcccgtgt tgacgccggg caagagcaac tcggtcgccg catacactat tctcagaatg   1140
acttggttga gtactcacca gtcacagaaa agcatcttac ggatggcatg acagtaagag   1200
aattatgcag tgctgccata accatgagtg ataacactgc ggccaactta cttctgacaa   1260
cgatcggagg accgaaggag ctaaccgctt ttttgcacaa catgggggat catgtaactc   1320
gccttgatcg ttgggaaccg gagctgaatg aagccatacc aaacgacgag cgtgacacca   1380
cgatgcctac agcaatggca acaacgttgc gcaaactatt aactggcgaa ctacttactc   1440
tagcttcccg gcaacaatta atagactgga tggaggcgga taaagttgca ggaccacttc   1500
tgcgctcggc ccttccggct ggctggttta ttgctgataa atctggagcc ggtgagcgtg   1560
ggtctcgcgg tatcattgca gcactggggc cagatggtaa gccctcccgt atcgtagtta   1620
tctacacgac ggggagtcag gcaactatgg atgaacgaaa tagacagatc gctgagatag   1680
gtgcctcact gattaagcat tggtaactgt cagaccaagt ttactcatat atactttaga   1740
```

```
ttgatttaaa acttcatttt taatttaaaa ggatctaggt gaagatcctt tttgataatc    1800
tcatgaccaa aatcccttaa cgtgagtttt cgttccactg agcgtcagac cccgtagaaa    1860
agatcaaagg atcttcttga gatccttttt ttctgcgcgt aatctgctgc ttgcaaacaa    1920
aaaaaccacc gctaccagcg gtggtttgtt tgccggatca agagctacca actcttttcc    1980
cgaaggtaac tggcttcagc agagcgcaga taccaaatac tgtccttcta gtgtagccgt    2040
agttaggcca ccacttcaag aactctgtag caccgcctac atacctcgct ctgctaatcc    2100
tgttaccagt ggctgctgcc agtggcgata agtcgtgtct taccgggttg gactcaagac    2160
gatagttacc ggataaggcg cagcggtcgg gctgaacggg gggttcgtgc acacagccca    2220
gcttggagcg aacgacctac accgaactga gatacctaca gcgtgagcta tgagaaagcg    2280
ccacgcttcc cgaagggaga aaggcggaca ggtatccggt aagcggcagg gtcggaacag    2340
gagagcgcac gagggagctt ccagggggaa acgcctggta tctttatagt cctgtcgggt    2400
ttcgccacct ctgacttgag cgtcgatttt tgtgatgctc gtcaggggg cggagcctat    2460 ggaaaaacgc cagcaacgcg gcctttttac ggttcctggc cttttgctgg ccttttgctc    2520
acatgttctt cctgcgtta tcccctgatt ctgtggataa ccgtattacc gcctttgagt    2580
gagctgatac cgctcgccgc agccgaacga ccgagcgcag cgagtcagtg agcgaggaag    2640
cggaagagcg cctgatgcgg tattttctcc ttacgcatct gtgcggtatt tcacaccgca    2700
tatggtgcac tctcagtaca atctgctctg atgccgcata gttaagccag tatacactcc    2760
gctatcgcta cgtgactggg tcatggctgc gccccgacac ccgccaacac ccgctgacgc    2820
gccctgacgg gcttgtctgc tcccggcatc cgcttacaga caagctgtga ccgtctccgg    2880
gagctgcatg tgtcagaggt tttcaccgtc atcaccgaaa cgcgcgaggc agcagatcaa    2940
ttcgcgcgcg aaggcgaagc ggcatgcatt tacgttgaca ccatcgaatg gtgcaaaacc    3000
tttcgcggta tggcatgata gcgcccggaa gagagtcaat tcagggtggt gaatgtgaaa    3060
ccagtaacgt tatacgatgt cgcagagtat gccggtgtct cttatcagac cgtttcccgc    3120
gtggtgaacc aggccagcca cgtttctgcg aaaacgcggg aaaaagtgga agcggcgatg    3180
gcggagctga attacattcc caaccgcgtg gcacaacaac tggcgggcaa acagtcgttg    3240
ctgattggcg ttgccacctc cagtctggcc ctgcacgcgc cgtcgcaaat tgtcgcggcg    3300
attaaatctc gcgccgatca actgggtgcc agcgtggtgg tgtcgatggt agaacgaagc    3360
ggcgtcgaag cctgtaaagc ggcggtgcac aatcttctcg cgcaacgcgt cagtgggctg    3420
atcattaact atccgctgga tgaccaggat gccattgctg tggaagctgc ctgcactaat    3480
gttccggcgt tatttcttga tgtctctgac cagacaccca tcaacagtat tattttctcc    3540
catgaagacg gtacgcgact gggcgtggag catctggtcg cattgggtca ccagcaaatc    3600
gcgctgttag cgggcccatt aagttctgtc tcggcgcgtc tgcgtctggc tggctggcat    3660
aaatatctca ctcgcaatca aattcagccg atagcggaac gggaaggcga ctggagtgcc    3720
atgtccggtt ttcaacaaac catgcaaatg ctgaatgagg gcatcgttcc cactgcgatg    3780
ctggttgcca acgatcagat ggcgctgggc gcaatgcgcg ccattaccga gtccgggctg    3840
cgcgttggtg cggatatctc ggtagtggga tacgacgata ccgaagacag ctcatgttat    3900
atcccgccgt caaccaccat caaacaggat tttcgcctgc tggggcaaac cagcgtggac    3960
cgcttgctgc aactctctca gggccaggcg gtgaagggca atcagctgtt gcccgtctca    4020
ctggtgaaaa gaaaaccacc cctggcgccc aatacgcaaa ccgcctctcc ccgcgcgttg    4080
gccgattcat taatgcagct ggcacgacag gtttcccgac tggaaagcgg gcagtgagcg    4140
```
caacgcaatt aatgtgagtt agcgcgaatt gatctg    4176

<210> SEQ ID NO 31
<211> LENGTH: 828
<212> TYPE: DNA
<213> ORGANISM: Uncultured marine bacterium 66A03
<220> FEATURE:
<221> NAME/KEY: misc_feature
<222> LOCATION: (1)..(828)
<223> OTHER INFORMATION: blh gene : DQ065755

<400> SEQUENCE: 31

| | |
|---|---|
| atgggcttga tgttaattga ttggtgtgct ttagcattgg ttgtgtttat tggttttgcca | 60 |
| catggtgcct tagatgctgc tatttctttt tcaatgattt cttcagcaaa gagaattgct | 120 |
| agattagcag gaatactatt aatttacctg ttgttagcaa ccgcattttt tttaatttgg | 180 |
| tatcaattac cagcattttc tcttctattt tttcttttga taagcataat ccattttgga | 240 |
| atggctgatt tcaatgcatc cccaagtaaa cttaagtggc ctcatattat tgcacatggc | 300 |
| ggcgttgtta ctgtttggtt gccgcttatc caaaaaaatg aagttacgaa gctattttca | 360 |
| atattaacaa atggtccaac tcccatttta tgggacatac tattgatatt tttttttatgt | 420 |
| tggagcatag gagtatgtct tcatacctat gaaactttac gttctaaaca ttataatatc | 480 |
| gcctttgaac ttattggatt aattttttcta gcctggtatg cacccccact cgttactttt | 540 |
| gccacatact tctgctttat ccacagcaga cgtcacttta gttttgtttg gaaacagtta | 600 |
| cagcatatga gttcaaaaaa aatgatgata ggtagtgcca ttattttatc ttgtacgagc | 660 |
| tggttgatag gcggaggaat atattttttc ctcaattcga aaatgattgc cagtgaagct | 720 |
| gctttacaaa ctgtctttat tggtcttgca gctttaacag ttcctcacat gatacttatc | 780 |
| gactttatat ttagaccaca ctcttccaga attaaaatca aaaattga | 828 |

<210> SEQ ID NO 32
<211> LENGTH: 828
<212> TYPE: DNA
<213> ORGANISM: Artificial Sequence
<220> FEATURE:
<223> OTHER INFORMATION: E. coli codon optimized blh gene of uncultured
      marine bacterium 66A03

<400> SEQUENCE: 32

| | |
|---|---|
| atgggtctga tgctgattga ttggtgtgca ctggctctgg ttgttttcat tggcctgccg | 60 |
| cacggcgcgc tggatgctgc catttctttt tctatgatct cttctgcaaa acgcattgct | 120 |
| cgtctggctg gtattctgct gatctatctg ctgctggcga ccgcgttctt cctgatctgg | 180 |
| tatcagctgc cagcgtttag cctgctgatc ttcctgctga tctccattat ccactttggt | 240 |
| atggcagact caacgcgtc cccaagcaaa ctgaaatggc cgcatatcat cgcccacggc | 300 |
| ggtgttgtta ctgtttggct gccgctgatc cagaaaaacg aagtaactaa actgtttagc | 360 |
| atcctgacta acggtccgac tccgatcctg tgggacatcc tgctgatttt cttcctgtgt | 420 |
| tggtctattg gcgtgtgtct gcacacgtac gaaaccctgc gctctaaaca ttacaacatc | 480 |
| gcctttgaac tgatcggtct gatttttcctg gcgtggtatg cgccgcctct ggttacgttt | 540 |
| gccacttact tctgcttcat tcattcccgt cgccacttct cctttgtgtg gaagcagctg | 600 |
| caacacatgt cttccaaaaa gatgatgatt ggcagcgcga ttatcctgtc ctgtacctct | 660 |
| tggctgatcg gcgtggtat ctatttcttc ctgaactcca aaatgatcgc ctctgaggct | 720 |
| gcgctgcaga ctgtgttcat cggtctggcg gcactgaccg tgccgcacat gattctgatc | 780 |

```
gacttcatct tccgtccgca ctcttcccgt atcaaaatca aaaactaa              828
```

<210> SEQ ID NO 33
<211> LENGTH: 1701
<212> TYPE: DNA
<213> ORGANISM: Mus musculus

<400> SEQUENCE: 33

```
atggagataa tatttggcca gaataagaaa gaacagctgg agccagttca ggccaaagtg    60
acaggcagca ttccagcatg gctgcagggg accctgctcc gaaacgggcc cgggatgcac   120
acagtgggag agagcaagta caaccattgg tttgatggcc tggcccttct ccacagtttc   180
tccatcagag atggggaggt cttctacagg agcaaatacc tgcagagtga cacctacatc   240
gccaacattg aggccaacag aatcgtggtg tctgagttcg gaaccatggc ctacccggac   300
ccctgcaaaa acatcttttc caaagctttc tcctacttgt ctcacaccat ccccgacttc   360
acagacaact gtctgatcaa catcatgaaa tgtggagaag acttctatgc aaccacggag   420
accaactaca tcaggaaaat cgaccccag accctagaga ccttggagaa ggttgattac   480
cggaagtatg tggcggtaaa cctggctacc tcgcaccctc attatgacga ggctgggaat   540
gtccttaaca tgggcacatc cgtcgtggac aaagggagga caaaatacgt gatatttaag   600
atccctgcca cagtgccaga cagcaagaag aaagggaaga gtcccgtgaa gcacgcggaa   660
gttttctgct ccatttcctc ccgctcgctg ctctctccca gctactacca gctttggt    720
gtcacggaga actatgtggt gtttctggag cagcctttta agttggatat cctcaagatg   780
gccaccgcat acatgagggg agtgagctgg gcttcctgta tgtcattcga cagggaggac   840
aagcataca ttcatatcat cgaccagagg accaggaagc ctgtgcctac caagttctac   900
acagatccca tggtggtctt ccatcatgtc aatgcctacg aggaggacgg ctgtgtgctg   960
tttgatgtga tcgcctatga ggacagcagc ctctatcagc tcttctacct ggccaacctg  1020
aacaaggact tcgaggagaa gtccaggctg acctcagtgc ctaccctcag gaggtttgct  1080
gtgcccctcc atgtggacaa ggatgcagaa gtgggctcaa atttagtcaa ggtgtcatct  1140
acaactgcaa cagccctgaa ggagaaagac ggccatgtct attgccagcc cgaggtcctc  1200
tacgaaggcc tagagctccc tcggataaat tatgcttaca cgggaagcc atatcgctac  1260
atctttgcag ctgaagtaca gtggagtcca gtcccaacca agatactgaa atatgacatt  1320
ctcacaaagt cctccttaaa gtggtctgag gagagctgct ggccagcaga gcctctgttt  1380
gttcccacgc caggtgcgaa ggatgaagat gatggagtca ttttatcagc catcgtctct  1440
acggatcccc aaaagctgcc ttttttactc attctggatg ccaaaagttt tacggaactg  1500
gctcgcgcct ctgttgatgc ggacatgcac ctggaccttc atggtttatt tatcccagat  1560
gcagactgga atgcagtgaa gcagactcca gctgaaacgc aagaggttga aaactcagat  1620
catcccacag atccgacagc accagaactg agccacagtg aaaatgactt cacagcgggt  1680
catggtggct caagtctttta a                                           1701
```

<210> SEQ ID NO 34
<211> LENGTH: 1053
<212> TYPE: DNA
<213> ORGANISM: Natronomonas pharaonis ATCC35678

<400> SEQUENCE: 34

```
atgagtaacg cgtcgctccg gccctccggg acggccagtg cgacactgtt ccggctggcg    60
```

```
ttcctcccgg gctgggctgt catcgcggcg acgacgggtg cgttcctcgt gggagcctca    120
ctacccctta cctaccaact catcccgctc gccgctagcg tggtcctgct cgggctccca    180
cacggcgctg tcgaccattt ggcgctcccg cggacccgaa acgagcgggt cacggttcga    240
tggcttgcgg ccatcggtgt cctctatgcc gttgtcggcg ggctctatgc ggcagtctgg    300
tttctcgcgc ccgtcggtgc cgtcgccgcg ttcattttta tgacgtgggt tcactggggc    360
caaggagaaa tctatccgct tgttgcgctc gctgacgccg accacctcga tgggcggctc    420
gaacgcggac tgacagccgc catccgcggc gcattgccga tgctcgtccc gtttgtcgcc    480
tttcccgacc agtacgagct cgtcgtgaca accctcgtcg gctcttcga cgccgatgca    540 gcggcgacgg cggcggccgc gttcacgccg accgcacggc tcgcagtcgc ggtcaccgtc    600
ggggggttgg tggcggtcac cctcggtatt ggagctgtcg ctgccagcga gaccggctgg    660
gggccgtggc tgcttgatgc cggcgaaaca gggcttctga ttctgttctt tgcggcggtg    720
ccgccgattt cgccatcgg cctctacttt tgtttctggc actcgcttcg ccacatcgtc    780
cggttgctcg ctgtcgataa ccgggcagca ccggcgctcg atggtcgccg atacggcgcg    840
gcgcttgcgc gctttgctcg ggatgcagcc ccgctgtcag cggcgtcgct cgtgttgctc    900
gggctgttgt atctagccgt gcccggcagc gtcgactcgc cgctttcgct tgtcgggacc    960
tacctcgtgt tgatagccgt gctcacgctc ccgcacgtgg tcgtcgtggc gtggatggac   1020
cacgaacagc ggctctggcg acccggagca tag                                1053

<210> SEQ ID NO 35
<211> LENGTH: 855
<212> TYPE: DNA
<213> ORGANISM: Halobacterium salinarum ATCC700922

<400> SEQUENCE: 35
atgccacacg gcgcgatcga ctacctcgcg ttgccccgcg cggtcacggg caccgtcacc     60
gtgcggtggc tggcggtcgt cggcgtcctc tacctcgtgc tcggtggtgg ctacgccgcc    120
gcgtggtttt tcgcgcccgt tcccgctgcg ttcgcgttcg tcgcgatcac gtggctgcac    180
tgggggcagg gcgacctcta cccgctgctc gacttcctcg acgtcgacta cctcgatacg    240
cgcccgcggc gcgcggcgac ggtcctgatc cggggtggcc tcccgatgct cgtgccgctg    300
ctcgggttcc cggagcggta ccgcagcgtc gtcgacgcgt tcgccgcgcc gttcggcggc    360
tccgtcggcg acctcgcggt gttcgacccg cgcgtccgcc tgtggctggg cgtcgcgttc    420
gcagccgcga ccgtcgcggt gctcgcggcg ggcagacgcc gcaccccactc ccccggcgcg    480 tggcgcgtcg acgccgccga aaccctcctg ttgtgggtgt tcttcttcgt cgtgccgccg    540
gtgttcgccg tcgcgtcta cttctgcgtc tggcactcgg tccggcacgt cgcgcgcgcc    600
atcgccgtcg acggctcggt ccacccgtcg ctgcgcgcgg gcgacatcct cggaccgctg    660
gcccggttcg gcgtggaggc cgcgccgatg acgcggccg cgctcgcgtt gggcggcgtg    720
ctgtggtggg cggtacccaa cccgccgacc acgtcgaat ccggggccgc actctacctc    780
gtgttgatcg ccgtgctcac cctgccacac gtcgccgtgg tcacgtggat ggaccgcgtg    840
cagggcgtcc tctga                                                    855

<210> SEQ ID NO 36
<211> LENGTH: 1080
<212> TYPE: DNA
<213> ORGANISM: Halobacterium salinarum ATCC700922

<400> SEQUENCE: 36
```

```
atgagcaata ggtcgcagtt cgtcccgtcg tggctcgtgc cggaggcagc cggcgaccto      60 ccgttgaccg tgtcgcggct gtcactgctc gcgcttgccg ccgcgttcgc ggtcggatac     120
ggcgcgggct cgcggtccc actggaggtc caggcgggcg tctacctgtt gggtatggtc      180
gcgatgaacc tcccgcacgg cggctacgag catttcgaga acctgcgcg acgggctgcc      240 tccttccagg gcaagtatat cgtcgcctac ctggtcggga tcgcggcgtt cggcgcgctg     300
tttttcgtcg cgcccgtcgc cggactgggg ctggcagtca cggtgccgt cgccaaaggt      360 gggttcggtg gcgtgcagtc gatggacgcc ctctacggaa ctgaccattt gcgcacgcgc     420
ccccagcggt ggctcgccgc cgtcgtccgg gcggcgcgg tgatggtggt tcccatgttg      480
ttctggacgg acgtgttcta cgcgttcagc tcggtcatga tctcgatttt cgaccccagc     540
gccgtgtcgg cgctcggcgg tgacatcgca accggcggc tcgtgctcgg cggcgggtac      600
ggggcgctcg tggtcgcaca cctggggctc ggctaccggc gggcggccgg caccgggtcg     660
ttcctcgccg acgccgccga gacgctgctg ttgatcgcgt acttcgcgct cgttccggtg     720
gtcatcgccg tcgggctgta cttcccgctg tggtactcgg cccgccaggt ggcccgatcg     780
tcggccgtcg acgacacggc gatgacgcag gcagacgcca ccggcatgct tgacgccctg     840
gacgccgacg acccggcgcg cgccacgctt gcctcgtggg cggtgctcat cgtcggcagc     900
gtcgccacgt tcggcctggc ggccgtgctc tggctgctgt ccccacagcc cctgggtggt     960
ggtgggatcc tcgtgggctt ggtcgcgttc tggagcatct tcgtgagcat catcgcgctc    1020
ccgcacgtcg tcgtcggcgg gtggcttgac cgcactcgcg gcatctggta cgtcccataa    1080
```

<210> SEQ ID NO 37
<211> LENGTH: 44
<212> TYPE: DNA
<213> ORGANISM: Artificial Sequence
<220> FEATURE:
<223> OTHER INFORMATION: Forward primer

<400> SEQUENCE: 37
cgagctcagg agcatttaga tgttgaaaac agtagttatt attg                       44

<210> SEQ ID NO 38
<211> LENGTH: 26
<212> TYPE: DNA
<213> ORGANISM: Artificial Sequence
<220> FEATURE:
<223> OTHER INFORMATION: Reverse primer

<400> SEQUENCE: 38
gcccggggtg gcctgaaacg gctacc                                          26

<210> SEQ ID NO 39
<211> LENGTH: 30
<212> TYPE: DNA
<213> ORGANISM: Artificial Sequence
<220> FEATURE:
<223> OTHER INFORMATION: Forward primer

<400> SEQUENCE: 39
gcccgggagg agttaaagaa atgacaattg                                      30

<210> SEQ ID NO 40
<211> LENGTH: 29
<212> TYPE: DNA
<213> ORGANISM: Artificial Sequence
<220> FEATURE:

<223> OTHER INFORMATION: Reverse primer

<400> SEQUENCE: 40
cggatccctt agtttcgata agagcgaac                                    29

<210> SEQ ID NO 41
<211> LENGTH: 31
<212> TYPE: DNA
<213> ORGANISM: Artificial Sequence
<220> FEATURE:
<223> OTHER INFORMATION: Forward primer

<400> SEQUENCE: 41
cggtaccaat gacaaaaaaa gttggtgtcg g                                 31

<210> SEQ ID NO 42
<211> LENGTH: 28
<212> TYPE: DNA
<213> ORGANISM: Artificial Sequence
<220> FEATURE:
<223> OTHER INFORMATION: Reverse primer

<400> SEQUENCE: 42
ttctagatta cgatttgtcg tcatgtcc                                     28

<210> SEQ ID NO 43
<211> LENGTH: 32
<212> TYPE: DNA
<213> ORGANISM: Artificial Sequence
<220> FEATURE:
<223> OTHER INFORMATION: Forward primer

<400> SEQUENCE: 43
ccccgggagg agagaaatta tgcaaacgga ac                                32

<210> SEQ ID NO 44
<211> LENGTH: 27
<212> TYPE: DNA
<213> ORGANISM: Artificial Sequence
<220> FEATURE:
<223> OTHER INFORMATION: Reverse primer

<400> SEQUENCE: 44
tgcatgctta tttaagctgg gtaaatg                                      27

<210> SEQ ID NO 45
<211> LENGTH: 2999
<212> TYPE: DNA
<213> ORGANISM: Artificial Sequence
<220> FEATURE:
<223> OTHER INFORMATION: pSTV28 vector sequence

<400> SEQUENCE: 45
cgtatggcaa tgaaagacgg tgagctggtg atatgggata gtgttcaccc ttgttacacc    60
gttttccatg agcaaactga aacgttttca tcgctctgga gtgaatacca cgacgatttc   120
cggcagtttc tacacatata ttcgcaagat gtggcgtgtt acggtgaaaa cctggcctat   180
ttccctaaag ggtttattga gaatatgttt ttcgtctcag ccaatccctg ggtgagtttc   240
accagttttg atttaaacgt ggccaatatg gacaacttct tcgcccccgt tttcaccatg   300
ggcaaatatt atacgcaagg cgacaaggtg ctgatgccgc tggcgattca ggttcatcat   360
gccgtctgtg atggcttcca tgtcggcaga atgcttaatg aattacaaca gtactgcgat   420
gagtggcagg gcggggcgta atttttttaa ggcagttatt ggtgccctta aacgcctggt   480

```
gctacgcctg aataagtgat aataagcgga tgaatggcag aaattcgaaa gcaaattcga    540
cccggtcgtc ggttcagggc agggtcgtta aatagccgct tatgtctatt gctggtttac    600
cggtttattg actaccggaa gcagtgtgac cgtgtgcttc tcaaatgcct gaggccagtt    660
tgctcaggct ctcccgtgg aggtaataat tgacgatatg atcatttatt ctgcctccca    720
gagcctgata aaacggtta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg   1020
ctcatggcgt tccaatacgc aaaccgcctc tcccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgaat   1260
tcgagctcgg tacccgggga tcctctagag tcgacctgca ggcatgcaag cttggcactg   1320
gccgtcgttt tacaacgtcg tgactgggaa accctggcg ttacccaact taatcgcctt   1380
gcagcacatc ccccttttcgc cagctggcgt aatagcgaag aggcccgcac cgatcgccct   1440
tcccaacagt tgcgcagcct gaatggcgaa tgagcttatc gatgataagc tgtcaaacat   1500
gagaattaca acttatatcg tatgggggctg acttcaggtg ctacatttga agagataaat   1560
tgcactgaaa tctagaaata ttttatctga ttaataagat gatcttcttg agatcgtttt   1620
ggtctgcgcg taatctcttg ctctgaaaac gaaaaaaccg ccttgcaggg cggttttttcg   1680 aaggttctct gagctaccaa ctctttgaac cgaggtaact ggcttggagg agcgcagtca   1740
ccaaaacttg tccttttcagt ttagccttaa ccggcgcatg acttcaagac taactcctct   1800
aaatcaatta ccagtggctg ctgccagtgg tgcttttgca tgtctttccg ggttggactc   1860
aagacgatag ttaccggata aggcgcagcg gtcggactga acgggggggt cgtgcataca   1920
gtccagcttg gagcgaactg cctacccgga actgagtgtc aggcgtggaa tgagacaaac   1980
gcggccataa cagcggaatg acaccggtaa accgaaaggc aggaacagga gagcgcacga   2040
gggagccgcc aggggaaacg cctggtatct ttatagtcct gtcgggtttc gccaccactg   2100
atttgagcgt cagatttcgt gatgcttgtc agggggggcgg agcctatgga aaaacggctt   2160
tgccgcggcc ctctcacttc cctgttaagt atcttcctgg catcttccag gaaatctccg   2220
ccccgttcgt aagccatttc cgctcgccgc agtcgaacga ccgagcgtag cgagtcagtg   2280
agcgaggaag cggaatatat cctgtatcac atattctgct gacgcaccgg tgcagccttt   2340
tttctcctgc cacatgaagc acttcactga caccctcatc agtgccaaca tagtaagcca   2400
gtatacactc cgctagcgct gatgtccggc ggtgcttttg ccgttacgca ccaccccgtc   2460
agtagctgaa caggagggac agctgataga aacagaagcc actggagcac tcaaaaaca   2520 ccatcataca ctaaatcagt aagttggcag catcacccga cgcactttgc gccgaataaa   2580
tacctgtgac ggaagatcac ttcgcagaat aaataaatcc tggtgtccct gttgataccg   2640
ggaagccctg gccaactttt tggcgaaaat gagacgttga tcggcacgta agaggttcca   2700
actttcacca taatgaaata agatcactac cgggcgtatt ttttgagtta tcgagatttt   2760
caggagctaa ggaagctaaa atggagaaaa aaatcactgg atataccacc gttgatatat   2820
```

```
cccaatggca tcgtaaagaa cattttgagg catttcagtc agttgctcaa tgtacctata    2880
accagaccgt tcagctggat attacggcct ttttaaagac cgtaaagaaa aataagcaca    2940
agttttatcc ggcctttatt cacattcttg cccgcctgat gaatgctcat ccggaattt     2999
```

```
<210> SEQ ID NO 46
<211> LENGTH: 32
<212> TYPE: DNA
<213> ORGANISM: Artificial Sequence
<220> FEATURE:
<223> OTHER INFORMATION: Forward primer

<400> SEQUENCE: 46
ccccgggagg agagaaatta tgcaaacgga ac                                    32

<210> SEQ ID NO 47
<211> LENGTH: 27
<212> TYPE: DNA
<213> ORGANISM: Artificial Sequence
<220> FEATURE:
<223> OTHER INFORMATION: Reverse primer

<400> SEQUENCE: 47
tgcatgctta tttaagctgg gtaaatg                                          27

<210> SEQ ID NO 48
<211> LENGTH: 30
<212> TYPE: DNA
<213> ORGANISM: Artificial Sequence
<220> FEATURE:
<223> OTHER INFORMATION: Forward primer

<400> SEQUENCE: 48
ccggaattca taatgagttt tgatattgcc                                       30

<210> SEQ ID NO 49
<211> LENGTH: 37
<212> TYPE: DNA
<213> ORGANISM: Artificial Sequence
<220> FEATURE:
<223> OTHER INFORMATION: Reverse primer

<400> SEQUENCE: 49
ctcctcgagt acgtatcatt atgccagcca ggccttg                               37

<210> SEQ ID NO 50
<211> LENGTH: 31
<212> TYPE: DNA
<213> ORGANISM: Artificial Sequence
<220> FEATURE:
<223> OTHER INFORMATION: Forward primer

<400> SEQUENCE: 50
ctcatgacgg tctgcgcaaa aaaacacgtt c                                     31

<210> SEQ ID NO 51
<211> LENGTH: 32
<212> TYPE: DNA
<213> ORGANISM: Artificial Sequence
<220> FEATURE:
<223> OTHER INFORMATION: Reverse primer

<400> SEQUENCE: 51
ggaattctta actgacggca gcgagttttt tg                                    32
```

```
<210> SEQ ID NO 52
<211> LENGTH: 35
<212> TYPE: DNA
<213> ORGANISM: Artificial Sequence
<220> FEATURE:
<223> OTHER INFORMATION: Forward primer

<400> SEQUENCE: 52
cgaattcagg agcgactaca tgaaaccaac tacgg                              35

<210> SEQ ID NO 53
<211> LENGTH: 31
<212> TYPE: DNA
<213> ORGANISM: Artificial Sequence
<220> FEATURE:
<223> OTHER INFORMATION: Reverse primer

<400> SEQUENCE: 53
ggagctctta gagcgggcgc tgccagagat g                                  31

<210> SEQ ID NO 54
<211> LENGTH: 32
<212> TYPE: DNA
<213> ORGANISM: Artificial Sequence
<220> FEATURE:
<223> OTHER INFORMATION: Forward primer

<400> SEQUENCE: 54
ggtcgacagg aggatcggga tgaccgcgag ac                                 32

<210> SEQ ID NO 55
<211> LENGTH: 30
<212> TYPE: DNA
<213> ORGANISM: Artificial Sequence
<220> FEATURE:
<223> OTHER INFORMATION: Reverse primer

<400> SEQUENCE: 55
gctgcagtta tgcgcgggtt cctgcaaatg                                    30

<210> SEQ ID NO 56
<211> LENGTH: 31
<212> TYPE: DNA
<213> ORGANISM: Artificial Sequence
<220> FEATURE:
<223> OTHER INFORMATION: Forward primer

<400> SEQUENCE: 56
gactagtgaa ttcaggaggt aataaatatg g                                  31

<210> SEQ ID NO 57
<211> LENGTH: 22
<212> TYPE: DNA
<213> ORGANISM: Artificial Sequence
<220> FEATURE:
<223> OTHER INFORMATION: Reverse primer

<400> SEQUENCE: 57
cactagttag tttttgattt tg                                            22

<210> SEQ ID NO 58
<211> LENGTH: 35
<212> TYPE: DNA
<213> ORGANISM: Artificial Sequence
<220> FEATURE:
<223> OTHER INFORMATION: Forward primer
```

<400> SEQUENCE: 58
ggaattcagg agcggttcca tggagataat atttg    35

<210> SEQ ID NO 59
<211> LENGTH: 27
<212> TYPE: DNA
<213> ORGANISM: Artificial Sequence
<220> FEATURE:
<223> OTHER INFORMATION: Reverse primer

<400> SEQUENCE: 59
gactagttaa agacttgagc caccatg    27

<210> SEQ ID NO 60
<211> LENGTH: 33
<212> TYPE: DNA
<213> ORGANISM: Artificial Sequence
<220> FEATURE:
<223> OTHER INFORMATION: Forward primer

<400> SEQUENCE: 60
ggaattcagg aggccgagta tgagtaacgc gtc    33

<210> SEQ ID NO 61
<211> LENGTH: 27
<212> TYPE: DNA
<213> ORGANISM: Artificial Sequence
<220> FEATURE:
<223> OTHER INFORMATION: Reverse primer

<400> SEQUENCE: 61
gactagttat gctccgggtc gccagag    27

<210> SEQ ID NO 62
<211> LENGTH: 32
<212> TYPE: DNA
<213> ORGANISM: Artificial Sequence
<220> FEATURE:
<223> OTHER INFORMATION: Forward primer

<400> SEQUENCE: 62
ggaattcagg aggtgttcgg catgccacac gg    32

<210> SEQ ID NO 63
<211> LENGTH: 30
<212> TYPE: DNA
<213> ORGANISM: Artificial Sequence
<220> FEATURE:
<223> OTHER INFORMATION: Reverse primer

<400> SEQUENCE: 63
gactagttag aggacgccct gcacgcggtc    30

<210> SEQ ID NO 64
<211> LENGTH: 34
<212> TYPE: DNA
<213> ORGANISM: Artificial Sequence
<220> FEATURE:
<223> OTHER INFORMATION: Forward primer

<400> SEQUENCE: 64
ggaattcagg aggtattcat atgagcaata ggtc    34

<210> SEQ ID NO 65
<211> LENGTH: 28

```
<212> TYPE: DNA
<213> ORGANISM: Artificial Sequence
<220> FEATURE:
<223> OTHER INFORMATION: Reverse primer

<400> SEQUENCE: 65
gactagttat gggacgtacc agatgccg                                     28
```

METHOD FOR PRODUCING RETINOID FROM MICROORGANISM

CROSS REFERENCE TO RELATED APPLICATIONS

This application is a National Phase application under 35 U.S.C. §371 of International Application No. PCT/KR2012/006071, filed Jul. 30, 2012, which claims priority to and the benefit of Republic of Korea Patent Application Nos. 10-2011-0075715 filed Jul. 29, 2011 and 10-2012-0083185 filed Jul. 30, 2012, the disclosures of which are incorporated herein by reference in its entirety.

BACKGROUND

1. Technical Field

The present invention relates to a method for production of retinoid from a microorganism with retinoid producing efficacy.

2. Description of the Related Art

Retinoid belongs to a class of lipophilic isoprenoid molecules chemically associated with vitamin A. The retinoid includes β-inone cyclic and polyunsaturated branched chains, together with alcohol (e.g., retinol), aldehyde (e.g., retinal), carboxylic acid (e.g., retinoic acid) or ester (e.g., retinyl acetate) functional groups. It is well known that such functional groups play an essential role in health care of a human body such as eyesight protection, bone growth and regeneration, anti-oxidation effects and prevention of skin aging, and may also reduce danger of cancer.

In recent years, the retinoid has attracted a great interest as an efficient raw material for cosmetics and medicaments useful for wrinkle improvement and treatment of skin disease. A scale of retinoid market is estimated at about 16 billion dollars over the world. Chemically synthesized retinoid is a representative raw material commercially available in the market. Retinol is produced by acidification or hydrolysis of retinal which was chemically synthesized through reduction of a pentadiene derivative. However, such a chemical process as described above entails disadvantages such as complicated purification processes and generation of undesirable byproducts. An animal creates retinoid using carotinoid obtained from fruits and vegetables, while a plant cannot synthesize retinoid. An overall path of retinoid synthesis is possibly embodied only in a specific microorganism that contains bacteriorhodopsin or proteorhodopsin having retinal as a prosthetic group. Nevertheless, the microorganism generates a protein combination form of retinal, thus not being preferable in mass production of free retinoids. Until now, although partially restricted attempts using enzymes for biological production have been executed, these have not yet gained successful results. Accordingly, there is still a need for development of a biotechnological method using metabolically transformed microorganisms in order to produce retinoid.

The retinoid is chemically unstable due to a conjugated and active double bond, and easily oxidized and becomes isomeric by heat, oxygen and light. Further, the retinoid is liable to be degraded through retinoic acid in biological aspects. Accordingly, an effective method for production of retinoid has yet to be developed.

SUMMARY

Therefore, an object of the present invention is to provide a method for effectively producing retinoid from a microorganism.

According to an aspect of the present invention, there is provided a method for production of retinoid from a microorganism, including: culturing a microorganism having retinoid producing efficacy in a medium containing a lipophilic substance; and isolating retinoid from the lipophilic substance phase.

The method may include culturing the microorganism having retinoid producing efficacy in a medium containing a lipophilic substance.

The term "microorganism" used herein may include a cell possible cultured in a liquid medium. The microorganism may include prokaryote cells, eukaryote cells or isolated animal cells, which are possibly cultured in a liquid medium. Such microorganisms may include, for example, bacteria, fungi or a combination thereof. Bacteria may include, for example, gram positive bacteria, gram negative bacteria or a combination thereof. The gram negative bacteria may include species of the genus *Escherichia*. The gram positive bacteria may include species of the genus *bacillus*, genus *corynebacterium, lactobacillus* or a combination thereof. The fungi may include yeast, *kluyveromyces* or a combination thereof. The microorganism may have natural or foreign genes introduced therein. The foreign gene may be a gene in association with production of retinoid such as at least one gene in an MEP or MVA path. The animal cell may include cells used for production of recombinant proteins. For instance, CHO cell, BHK cell or a combination thereof may be included.

The microorganism of the genus *Escherichia* having retinoid producing efficacy may include microorganisms of the genus of natural or transformed *Escherichia*. The microorganism in the natural genus *Escherichia* is known to have the MEP path as an inherent path for retinoid synthesis. The microorganism in the transformed genus *Escherichia* may include genes associated with an inherent MEP path for retinoid synthesis, genes associated with a foreign MVA path for retinoid synthesis or a combination thereof, which are introduced therein. The MVA path gene may be a gene encoding an enzyme in a foreign mevalonate path in association with production of IPP from acetyl-CoA. Alternatively, a strain into which a gene encoding an enzyme associated with synthesis of β-carotene from the above IPP has been introduced may also be included. Further, the foregoing microorganism may be one having at least two copies of IPP isomerases introduced therein, which in turn, shows promoted conversion from IPP to DMAPP. Therefore, the microorganism may the retinoid at a high concentration. FIG. 1 is a view schematically illustrating an MEP path and a foreign MVA path of retinal biosynthesis.

The microorganism in the natural genus *Escherichia* may include, for example, *Escherichia coli*. Such genus *Escherichia coli* may include, for example, DH5α, MG1655, BL21 (DE), S17-1, XL1-Blue, BW25113 or a combination thereof.

The microorganism in the transformed genus *Escherichia* may be one transformed into, for example: a gene encoding acetyl-CoA acetyl transferase/hydroxymethylglutaryl (HMG)-CoA reductase derived from *Enterococcus faecalis*, which is defined by SEQ. ID No. 1; a gene encoding HMG-CoA synthase derived from *Enterococcus faecalis*, which is defined by SEQ. ID No. 2; a gene encoding mevalonate kinase derived from *Streptococcus pneumoniae*, which is defined by SEQ. ID No. 3; a gene encoding phosphomevalonate kinase derived from *Streptococcus pneumoniae*, which is defined by SEQ. ID No. 4; a gene encoding mevalonate diphosphate decarboxylase derived from *Streptococcus pneumoniae*, which is defined by SEQ.

ID No. 5; a gene encoding isopentinyl diphosphate (IPP) isomerase derived from *Escherichia coli*, which is defined by SEQ. ID No. 6; a gene encoding geranylgeranyl pyrophosphate (GGPP) synthase derived from *Pantoea agglomerans*, which is defined by SEQ. ID No. 7; a gene encoding phytoene synthase derived from *Pantoea agglomerans*, which is defined by SEQ. ID No. 8; a gene encoding phytoene dehydrogenase derived from *Pantoea agglomerans*, which is defined by SEQ. ID No. 9; and a gene encoding lycopene β-cyclase derived from *Pantoea ananatis*, which is defined by SEQ. ID No. 10.

The microorganism in the transformed genus *Escherichia* may be one transformed into any one of the genes defined by SEQ. ID Nos. 1 to 10, and may be further transformed into at least one selected from a group consisting of, for example: a gene encoding β-carotene monooxygenase derived from uncultured marine bacterium 66A03, which is defined by SEQ. ID No. 13; a gene encoding β-carotene 15,15'-monooxygenase derived from *Mus musculus*, which is defined by SEQ. ID No. 14; a gene encoding brp-like protein 2 (brp 2) derived from *Natronomonas pharaonis* ATCC35678, which is defined by SEQ. ID No. 15; and a gene encoding β-carotene monooxygenase derived from *Halobacterium salinarum* ATCC700922, which is defined by SEQ. ID No. 16 or 17, or the like.

The microorganism described above may produce retinoid further transformed into a gene encoding IPP isomerase derived from *Haematococcus pluvialis*, which is defined by SEQ. ID No. 12.

The microorganism having retinoid producing efficacy may be transformed into a gene encoding 1-deoxyxylolose-5-phosphate (DXP) synthase (dxs) derived from *Escherichia coli*, which is defined by SEQ. ID No. 11. Since DXP is an enzyme corresponding to a process of determining a velocity in an inherent MEP path, the above microorganism can produce β-carotene at a high concentration by further introducing a gene encoding DXP synthase.

If the microorganism having retionid producing efficacy of the present invention belongs to the genus *Escherichia*, it may be, for example, *Escherichia coli* DH5α/pTDHB/pSNA with Accession No. KCTC 11254BP (Korean collection for type culture, deposited on Jan. 2, 2008) or *Escherichia coli* DH5α/pTDHBSR/pSNA with Accession No. KCTC 11255BP (Korean collection for type culture, deposited on Jan. 2, 2008). In particular, or *Escherichia coli* DH5α/pTDHBSR/pSNA can produce retinoid with high productivity from a carbon source in a medium. The microorganisms, *Escherichia coli* DH5α/pTDHB/pSNA and *Escherichia coli* DH5α/pTDHBSR/pSNA, were duly deposited with Korean Collection for Type Cultures (KCTC) (having the address of Biological Resource Center (BRC), Korea Research Institute of Bioscience and Biotechnology (KRIBB), 52 Eoeun-dong, Yuseong-gu, Daejeon 305-333, Republic of Korea) under the Access numbers of KCTC11254BP and KCTC 11255BP, respectively, on Jan. 2, 2008. The deposits have been made under the terms of the Budapest Treaty and all restrictions imposed by the depositor on the availability to the public of the biological material will be irrevocably removed upon the granting of a patent.

According to one embodiment, the microorganism described above may be a microorganism in the genus *Escherichia* transformed into, for example: a gene encoding acetyl-CoA acetyltransferase/hydroxymethylglutaryl (HMG)-CoA reductase derived from *Enterococcus faecalis*, which is defined by SEQ. ID No. 1; a gene encoding HMG-CoA synthase derived from *Enterococcus faecalis*, which is defined by SEQ. ID No. 2; a gene encoding mevalonate kinase derived from *Streptococcus pneumoniae*, which is defined by SEQ. ID No. 3; a gene encoding phosphomevalonate kinase derived from *Streptococcus pneumoniae*, which is defined by SEQ. ID No. 4; a gene encoding mevalonate diphosphate decarboxylase derived from *Streptococcus pneumoniae*, which is defined by SEQ. ID No. 5; a gene encoding isopentinyl diphosphate (IPP) isomerase derived from *Escherichia coli*, which is defined by SEQ. ID No. 6; a gene encoding geranylgeranyl pyrophosphate (GGPP) synthase derived from *Pantoea agglomerans*, which is defined by SEQ. ID No. 7; a gene encoding phytoene synthase derived from *Pantoea agglomerans*, which is defined by SEQ. ID No. 8; a gene encoding phytoene dehydrogenase derived from *Pantoea agglomerans*, which is defined by SEQ. ID No. 9; a gene encoding lycopene β-cyclase derived from *Pantoea ananatis*, which is defined by SEQ. ID No. 10; a gene encoding 1-deoxyxylolose-5-phosphate (DXP) synthase (dxs) derived from *Escherichia coli*, which is defined by SEQ. ID No. 11; and a gene encoding IPP isomerase derived from *Haematococcus pluvialis*, which is defined by SEQ. ID No. 12. More particularly, such a microorganism in the genus *Escherichia* as described above may be a microorganism in the genus *Escherichia* further transformed into at least one gene selected from a group consisting of, for example: a gene encoding β-carotene monooxygenase derived from uncultured marine bacterium 66A03, which is defined by SEQ. ID No. 13; a gene encoding β-carotene 15,15'-monooxygenase derived from *Mus musculus*, which is defined by SEQ. ID No. 14; a gene encoding brp-like protein 2 (brp 2) derived from *Natronomonas pharaonis* ATCC35678, which is defined by SEQ. ID No. 15; and a gene encoding β-carotene monooxygenase derived from *Halobacterium salinarum* ATCC70922, which are defined by SEQ. ID Nos. 16 and 17. The gene encoding β-carotene monooxygenase derived from uncultured marine bacterium 66A03, which is defined by SEQ. ID No. 13, may have a base sequence defined by SEQ. ID No. 32, which is codon-optimized in *Escherichia coli*.

In the present text, the term "retinoids" means a species of chemical substances chemically associated with vitamin A. The retinoid may have a structure consisting of a cyclic end group, polyene branched chain and polar end group. A conjugate system formed by alternately aligning C=C double bonds in the polyene branched chain may express color of the retinoid (usually yellow, orange or red color). Most of retinoids are chromophore. By altering the branched chain and end groups, a variety of retinoids may be produced. Such retinoids may include retinal, retinol, retinoic acid, retinyl acetate or a combination thereof. Further, the retinoid may include any product of in vivo degradation of retinal, retinol, retinoic acid, retinyl acetate or a combination thereof.

The retinoid is a material having 20 basic carbon atoms and, according to fatty acid prosthetic groups bonded thereto, the final number of carbon atoms may be changed. For instance, in case of acetate bonding, the final number of carbon atoms is 22. On the other hand, for oleic acid bonding, the final number of carbon atoms may be 38.

The lipophilic substance described above may be an organic compound having 8 to 50 carbon atoms with lipophilic properties.

The lipophilic substance may include, for example, an alkane compound having 8 to 50 carbon atoms, a compound represented by Formula 1 below, a compound represented by Formula 2 below, or a combination thereof.

$R_1(CO)OR_2$ [Formula 1]

(wherein $R_1$ and $R_2$ are each independently alkyl having 8 to 50 carbon atoms, and CO represents a carbonyl group).

[Formula 2]

$$\begin{array}{l} CH_2O(CO)R_3 \\ | \\ CHO(CO)R_4 \\ | \\ CH_2O(CO)R_5 \end{array}$$

(wherein $R_3$, $R_4$ and $R_5$ are each independently alkyl having 8 to 50 carbon atoms, and CO represents a carbonyl group).

The alkane compound having 8 to 50 carbon atoms may be straight alkane, brached alkane, cyclic alkane or a combination thereof. The alkane compound may include compounds having carbon atoms in a range of, for example: 8 to 46; 8 to 40; 8 to 36; 8 to 30; 8 to 26; 8 to 20; 8 to 16; 8 to 12; 8 to 10; 10 to 50; 10 to 46; 10 to 40; 10 to 36; 10 to 30; 10 to 26; 10 to 20; 10 to 17; to 12; 10 to 50; 10 to 46; 12 to 50; 12 to 46; 12 to 36; 12 to 30; 12 to 26; 12 to 20; or 12 to 16.

The straight alkane may include alkanes having 8 carbon atoms (octane), 10 carbon atoms (decane), 12 carbon atoms (dodecane), 14 carbon atoms (tetradecane), or alkanes having 16, 18, 20, 22, 24, 26, 28, 30, 32, 34, 36, 38, 40, 42, 44, 46, 48 or 50 carbon atoms, or a combination thereof.

The branched alkane may include alkanes having 8, 10, 12, 14, 16, 18, 20, 22, 24, 26, 28, 30, 32, 34, 36, 38, 40, 42, 44, 46, 48 or 50 carbon atoms, or a combination thereof. The branched alkane may include saturated analogues of a terpene compound. For instance, phytosqualane may be included.

A combination of the straight alkane, branched alkane and cyclic alkane may be mineral oil. The mineral oil may be a mixture of alkanes having 15 to 40 carbon atoms, which are derived from non-vegetable raw materials (mineral). The alkane having 15 to 40 carbon atoms may include, for example, at least two mixtures of alkanes having 15, 16, 17, 18, 19, 20, 21, 22, 23, 24, 25, 26, 27, 28, 29, 30, 31, 32, 33, 34, 35, 36, 37, 38, 39 or 40 carbon atoms.

The mineral oil may be lightweight or heavy mineral oil. The lightweight mineral oil is a substance generally having a density of 880 to 920 kg/m$^3$, a specific gravity of 820 to 860 kg/m$^3$ at 20° C., and a fluid viscosity of 14 to 18 cst at 40° C. On the other hand, the heavy mineral oil is a substance generally having a density of 920 kg/m3, a specific gravity of 860 to 900 kg/m$^3$ at 20° C., and a fluid viscosity of 65 to 85 cst at 40° C.

In the compound represented by Formula 1, $R_1$ and $R_2$ are each independently straight, branched or cyclic alkyl having 8 to 50 carbon atoms. Herein, $R_1$ and $R_2$ may be each independently alkyl having 8, 10, 12, 14, 16, 18, 20, 22, 24, 26, 28, 30, 32, 34, 36, 38, 40, 42, 44, 46, 48 or 50 carbon atoms.

$R_1$ and $R_2$ may be each independently alkyl having carbon atoms in a range of 8 to 50, for example: 8 to 46; 8 to 40; 8 to 36; 8 to 30; 8 to 26; 8 to 20; 8 to 16; 8 to 12; 8 to 10; 10 to 50; 10 to 46; 10 to 40; 10 to 36; 10 to 30; 10 to 26; 10 to 20; 10 to 16; 10 to 12; 10 to 50; 10 to 46; 12 to 50; 12 to 46; 12 to 36; 12 to 30; 12 to 26; 12 to 20; or 12 to 16. $R_1$ may be a straight alkyl having 13 carbon atoms while $R_2$ is isopropyl. Further, $R_1$ may be ethylpentyl while $R_2$ is cetyl.

In the compound represented by Formula 2, $R_3$, $R_4$ and $R_5$ are each independently straight, branched or cyclic alkyl having 8 to 50 carbon atoms.

$R_3$, $R_4$ and $R_5$ may be each independently alkyl having 8, 10, 12, 14, 16, 18, 20, 22, 24, 26, 28, 30, 32, 34, 36, 38, 40, 42, 44, 46, 48 or 50 carbon atoms. The foregoing compound may contain $R_3$, $R_4$ and $R_5$, which are each independently alkyl having carbon atoms in a range of 8 to 50, for example: 8 to 46; 8 to 40; 8 to 36; 8 to 30; 8 to 26; 8 to 20; 8 to 16; 8 to 12; 8 to 10; 10 to 50; to 46; 10 to 40; 10 to 36; 10 to 30; 10 to 26; 10 to 20; 10 to 16; 10 to 12; 10 to 50; 10 to 46; 12 to 50; 12 to 46; 12 to 36; 12 to 30; 12 to 26; 12 to 20; or 12 to 16.

The lipophilic substance may include, for example, octane, decane, dodecane, tetradecane, phytosqualane, mineral oil, isopropyl myristate, cetyl ethylhexanoate, dioctanoyl decanoyl glycerol, squalane, or a combination thereof.

The lipophilic substance may not only stabilize produced retinoids but also increase productivity of the retinoids by microorganisms. The lipophilic substance does not affect growth of microorganisms or may slightly influence on the same.

Culture may be performed in a synthetic, semi-synthetic or combined culture medium. Such a culture medium may include, for example, a medium consisting of a carbon source, nitrogen source, vitamin and mineral. For instance, a Man-Rogosa-Sharp (MRS) liquid medium or a milk-added liquid medium may be used.

The carbon source of the medium may include starch, dextrose, sucrose, galactose, fructose, glycerol, glucose, or a mixture thereof. For instance, glycerol may be used as the carbon source. The nitrogen source may include ammonium sulfate, ammonium nitrate, sodium nitrate, glutamic acid, casaminoic acid, yeast extract, peptone, tryptone, soy bean husk, or a mixture thereof. Mineral may include sodium chloride, potassium (II) phosphate, magnesium sulfate, or a mixture thereof.

When the culturing is executed in a fermentation tank, glucose is preferably used as a carbon source. For test tube culture, glycerol is preferably used as a carbon source.

The carbon source, nitrogen source and mineral in the medium for culturing microorganisms are used in an amount of 10 to 100 g, 5 to 40 g and 0.5 to 4 g, respectively, to 1 liter.

Vitamin added to a typical culture medium under general culture conditions of *Escherichia coli* may be vitamin A, vitamin B, vitamin C, vitamin D, vitamin E or a mixture thereof. The vitamin may be added to the typical culture medium together with such carbon source, nitrogen source and/or mineral as described above. Otherwise, the vitamin may be alternatively added to a sterilized medium.

The culturing may be executed under general culture conditions. The culturing may be executed at a temperature in a range of 15 to 45° C., for example, 15 to 44° C.; 15 to 43° C.; 15 to 42° C.; 15 to 41° C.; 15 to 40° C.; 15 to 39° C.; 15 to 38° C.; 15 to 37° C.; 15 to 36° C.; 15 to 35° C.; 15 to 34° C.; 15 to 33° C.; 15 to 32° C.; 15 to 31° C.; 15 to 30° C.; 20 to 45° C.; 20 to 44° C.; 20 to 43° C.; 20 to 42° C.; 20 to 41° C.; 20 to 40° C.; 20 to 39° C.; 20 to 38° C.; 20 to 37° C.; 20 to 36° C.; 20 to 35° C.; 20 to 34° C.; 20 to 33° C.; 20 to 32° C.; 20 to 31° C.; 20 to 30° C.; 25 to 45° C.; 25 to 44° C.; 25 to 43° C.; 25 to 42° C.; 25 to 41° C.; 25 to 40° C.; 25 to 39° C.; 25 to 38° C.; 25 to 37° C.; 25 to 36° C.; 25 to 35° C.; 25 to 34° C.; 25 to 33° C.; 25 to 32° C.; 25 to 31° C.; 25 to 30° C.; 27 to 45° C.; 27 to 44° C.; 27 to 43° C.; 27 to 42° C.; 27 to 41° C.; 27 to 40° C.; 27 to 39° C.; 27 to 38° C.; 27 to 37° C.; 27 to 36° C.; 27 to 35° C.; 27 to 34° C.; 27 to 33° C.; 27 to 32° C.; 27 to 31° C.; or 27 to 30° C.

In order to collect or recover concentrated strain after removing the culture medium in a culture solution, centrifugation or filtration may be conducted. Such a process may be optionally executed according to demands of those skilled in the art. By freezing or freeze-drying the concentrated strain according to any conventional method, activities of the strain may be retained.

According to one example of the culturing, the culturing may be performed in a medium containing glycerol as a carbon source. Glycerol may be only the carbon source in the medium. The culturing may be conducted in a medium containing glycerol in an amount of 0.5 to 5.0% (w/v), for example: 0.5 to 4.5% (w/v); 0.5 to 4.0% (w/v); 0.5 to 3.5% (w/v); 0.5 to 3.0% (w/v); 0.5 to 2.5% (w/v); 0.5 to 2.0% (w/v); 0.5 to 1.5% (w/v); 1 to 4.5% (w/v); 1 to 4.0% (w/v); 1 to 3.5% (w/v); 1 to 3.0% (w/v); or 1 to 2.5% (w/v). Such a medium may be an YT medium including glycerol and arabinose added thereto. The YT medium may include 1.6 wt. % of tryptone, 1 wt. % of yeast extract and 0.5 wt. % of NaCl.

The culturing may be performed in a culture medium in the presence of a lipophilic substance while placing a dodecane phase formed of a lipophilic substance on the surface of the medium. The culturing may be performed under agitation.

The agitation may be conducted at a range of 100 to 300 rpm, for example, 100 to 280 rpm, 100 to 260 rpm, 100 to 240 rpm, 100 to 220 rpm, 100 to 200 rpm, 100 to 180 rpm, 100 to 160 rpm, 100 to 140 rpm, 100 to 120 rpm, 120 to 300 rpm, 120 to 280 rpm, 120 to 260 rpm, 120 to 240 rpm, 120 to 220 rpm, 120 to 200 rpm, 120 to 180 rpm, 120 to 160 rpm, 120 to 140 rpm, 150 to 300 rpm, 150 to 280 rpm, 150 to 260 rpm, 150 to 240 rpm, 150 to 220 rpm, 150 to 200 rpm, 150 to 180 rpm, 140 to 160 rpm, 200 to 300 rpm, 200 to 280 rpm, 200 to 260 rpm, 200 to 240 rpm, 200 to 220 rpm, or 150 rpm.

In case of agitating, the lipophilic substance, that is, dodecane may be dispersed in the medium and contact with cells. Since the lipophilic substance is dispersed in the medium to increase a microorganism-contacting area, retinoid may be efficiently isolated from the cells during culturing, thereby enabling stabilization and dissolution of the retinoid.

When a microorganism for producing retinoids was cultured without the lipophilic substance, that is, the dodecane phase, the production of retinoids may reach a maximum level at a constant time and, thereafter, become decrease. The reason of such facts may be because a further synthesis of retinoid is stopped during the growth of microorganism has stagnated, while occurring intracellular oxidative degradation of the retinoid.

If the microorganism is cultured in a culture medium in the presence of the lipophilic substance, that is, dodecane phase, the produced retinoid may be absorbed in to the lipophilic substance, that is, dodecane phase before the retinoid is degraded in the cell, thereby improving productivity of retinoid.

The lipophilic substance, that is, dodecane phase does not affect upon the cellular growth of a microorganism in the genus *Escherichia*, instead, may be hydrophobic and used for extracting the retinoid and have a low volatility. FIG. 2 illustrates conversion of β-carotene into retinoids including retinal, retinol, retinoic acid and retinyl ester.

A ratio by volume of medium to lipophilic substance may be, for example: 1:0.1 to 3.0, 1:0.5 to 3.0, 1:1.0 to 3.0, 1:1.5 to 3.0, 1:2.0 to 3.0, 1:2.5 to 3.0, 1:0.2 to 2.5, 1:0.2 to 2.0, 1:0.2 to 1.5, 1:0.2 to 1.0, 1:0.2 to 0.5, 1:0.5 to 2.5, 1:0.5 to 2.0, 1:0.5 to 1.5, 1:0.5 to 1.0, 1:0.8 to 2.5, 1:0.8 to 2.0, 1:0.8 to 1.5, 1:0.8 to 1.2, 1:0.8 to 1.0, or the like.

According to one embodiment, the medium may contain glycerol at a concentration of about 2.0% during culturing, the microorganism in the genus *Escherichia* may be *Escherichia coli* DH5α or MG1655, and the culturing may include culturing using 7 ml of a culture solution at about 29° C.

The foregoing method may include isolating retinoid from a lipophilic substance phase. A method for isolation of the retinoid including, for example, retinal, retinol, retinoic acid, retinyl ester or a combination thereof is well known in the art. For example, the retinoid may be isolated by a conventional method such as ion exchange chromatography, HPLC or the like. For instance, in order to obtain a high purity product after recovering a strain and extracting the same using a solvent such as acetone, separation and purification through HPLC or crystallization may be conducted.

A method for production of retinoid from a microorganism in the genus *Escherichia* according to one embodiment of the present invention may include: culturing the microorganism having retinoid producing efficacy in the genus *Escherichia*, in a medium including a lipophilic substance; and isolating the retinoid from the lipophilic substance phase, wherein the lipophilic substance is an alkane compound having 8 to 50 carbon atoms, a compound represented by Formula 1, a compound represented by Formula 2 or a combination thereof.

The method for production of retinoid according to the present invention may produce retinol with high efficiency.

DETAILED DESCRIPTION

Figure 1:
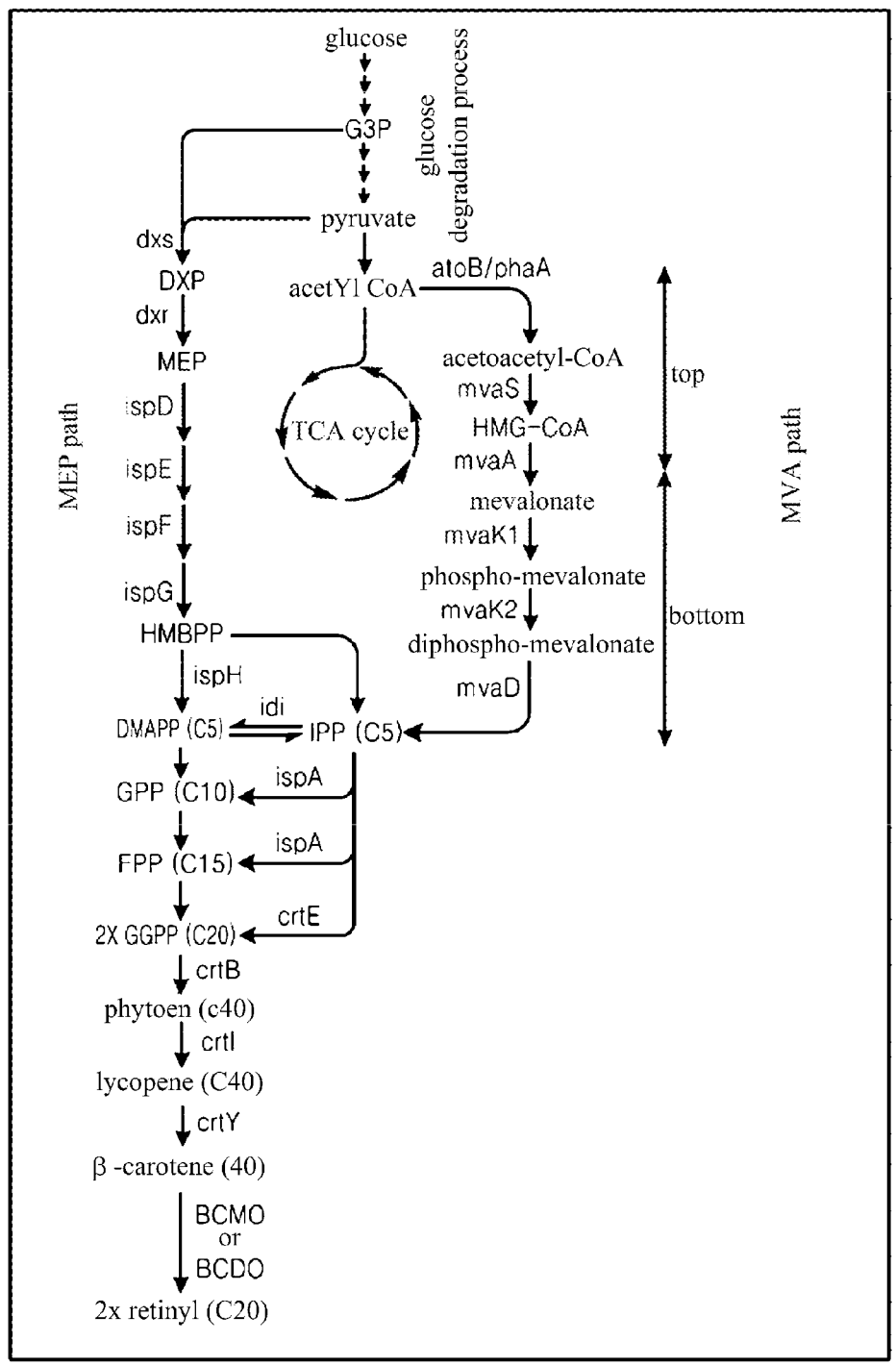
FIG. 1 is a view schematically illustrating an MEP path and a foreign MVA path of retinal biosynthesis.

Hereinafter, the present invention will be described in more details according to the following examples. However, these examples are proposed for illustrative purposes only and the scope of the present invention is not particularly limited thereto. In the examples, the following experimental materials and methods have been used.

Bacteria Strain and Culture Conditions

*Escherichia coli* DH5α was used for gene cloning and retinoid production. Alternatively, *Escherichia coli* MG1655, BL21 (DE3), XL1-Blue, S17-1 and BW25113 were used to investigate an optimum strain for retinoid production. The culture for retinoid production was executed in a 2YT medium (including 16 g of tryptone, 10 g of yeast extract and 5 g of NaCl per liter) at 29° C. using an agitation incubator operating at 250 rpm. A major and additional carbon sources were glycerol and arabinose, which were added in concentrations of 0.5 to 2% (w/v) and 0.2% (w/v), respectively, to the incubator. Alternative carbon sources for retinoid production, for example, glucose, galactose, xylose and maltose were compared to glycerol. Ampicillin (100 μg/mL) and chloramphenicol (50 μg/mL) were optionally added to a culture solution requiring the same. The culturing was conducted in a test tube containing 7 ml of medium. Cell growth was determined by measuring an optical density at 600 nm ($OD_{600}$). In a 2-phase culture method for production of retinoid, 1 mL of dodecane (Cat. No. 297879, Sigma, USA) was placed on 5 ml of the culture medium.

Conditions for Analysis of β-Carotene and Retinoid

β-carotene and retinoid were extracted from bacteria cell pellets through acetone. In the 2-phase culture method including dodecane capping, cell pieces were completely removed by collecting a dodecane phase containing retinoid and centrifuging the same at 14,000 rpm for 10 minutes. The acetone extraction product and dodecane phase were analyzed using HPLC (LC-20A, Shimadzu, Kyoto, Japan) at detection wavelengths of 370 nm (retinal), 340 nm (retinol and retinyl acetate) and 454 nm (β-carotene). The analysis was performed using a Symmetry C18 type (250 mm×4.6 mm, 5 m) HPLC column including Sentry Guard C18 (15 mm×4.6 mm, 5 m). A mobile phase of the column was each of methanol and acetonitrile in ratios of 95:5 and 70:30, respectively, for analyzing retinoid and β-carotene. HPLC analysis was performed at a flow rate of 1.5 ml/min and a column temperature of 40° C. Retinal (Cat. No. R2500), retinol (Cat. No. R7632), retinyl acetate (Cat. No. R4632) and β-carotene (Cat. No. C4582) were purchased from Sigma Co. (USA) and dissolved in acetone, respectively, to prepare standard compounds, and each of the prepared standard compounds was used. Through three independent experiments, results were obtained and represented by a mean±SD.

EXAMPLE 1

Preparation of Vector for Producing *Escherichia coli* with High Productivity of β-Carotene and Retinal Conventional processes involving genome DNA preparation, restriction enzyme cleavage, transformation and standard molecular biological technologies have been executed according to description in related documents (Sambrook and Russell 2001). PCR was performed using pfu DNA polymerase according to standard protocols (Solgent Co., Korea). blh gene of uncultured marine bacteria 66A03 (Genbank accession No. AAY68319) was synthesized into Genofocus (Daejeon, Korea) according to codon-optimization by Gene Designer software (DNA 2.0, Menlo Park, USA), in order to express the above gene in *Escherichia coli*.

According to the present example, an enzyme involved in a velocity determination process, that is, a gene encoding DXP synthase was additionally introduced into *Escherichia coli* having an MEP path and, at the same time, a gene encoding an enzyme associated with a mevalonate path was selected from a variety of gene resources and introduced, thus preparing *Escherichia coli* with high productivity of β-carotene.

(1) Preparation of pSNA Vector Including a Gene Encoding an Enzyme in a Mevalonate Path Associated with Synthesis of IPP from a Carbon Source Genes encoding an enzyme in a mevalonate path associated with IPP synthesis from a carbon source used in the present experiment are shown in Table 1 below.

TABLE 1

| Name of enzyme | Gene | Gene sequence (Genbank accession No.) |
|---|---|---|
| Acetyl-CoA acetyltransferase/hydroxymethylglytaryl (HMG)-CoA reductase derived from *Enterococcus faecalis* | mvaE | SEQ. ID No. 18 (AF290092) |
| HMG-CoA synthase derived from *Enterococcus faecalis* | mvaS | SEQ. ID No. 19 (AF290092) |

TABLE 1-continued

| Name of enzyme | Gene | Gene sequence (Genbank accession No.) |
|---|---|---|
| Mevalonate kinase derived from *Streptococcus pneumonia* | mvaK1 | SEQ. ID No. 20 (AF290099) |
| Phosphomevalonate kinase derived from *Streptococcus pneumonia* | mvaK2 | SEQ. ID No. 21 (AF290099) |
| Mevalonate diphosphate decarboxylase derived from *Streptococcus pneumoniae* | mvaD | SEQ. ID No. 22 (AF290099) |
| Isopentenyl diphosphate (IPP) isomerase derived from *Escherichia coli* | Idi | SEQ. ID No. 23 (U00096) |

Primers and restriction enzymes to amplify genes listed in Table 1 have been described.

TABLE 2

| | | Primer sequence | Restriction enzyme |
|---|---|---|---|
| mvaE | F | SEQ. ID No. 37 | SacI |
| | R | SEQ. ID No. 38 | SmaI |
| mvaS | F | SEQ. ID No. 39 | SmaI |
| | R | SEQ. ID No. 40 | BamHI |
| mvaK1, mvaK2, mvaD | F | SEQ. ID No. 41 | KpnI |
| | R | SEQ. ID No. 42 | XbaI |
| Idi | F | SEQ. ID No. 43 | SmaI |
| | R | SEQ. ID No. 44 | SphI |

The primer sequences and restriction enzymes used in cloning the genes listed in Table 1 are stated in Table 2. Since mvaK1, mvaK2 and mvaD are present as a single operon in a chromosome, a whole operon rather than individual genes was subjected to PCR cloning at once.

The genes listed in Table 1 were amplified using the primers listed in Table 3 through PCR which uses a chromosome DNA in each strain including corresponding gene as a matrix. The amplified product was introduced into pSTV28 vector (Takara Korea, Korea) (SEQ. ID No. 45) using the restriction enzymes listed in Table 2, thereby preparing the vector pSNA. The vector pSNA includes all of genes encoding the enzyme in a mevalonate path, which can produce IPP from acetyl-CoA.

(2) Preparation of Vectors pT-HB and pT-DHB Including a Gene Encoding an Enzyme Associated with Synthesis of β-Carotene from IPP Genes encoding an enzyme associated with synthesis of β-carotene from IPP used in the present experiment, as well as DXP synthase gene as an enzyme involved in the velocity determination process in the MEP path, are shown in Table 3 below.

TABLE 3

| Name of enzyme | Gene | Gene sequence (Genbank accession No.) |
|---|---|---|
| IPP isophomerase derived from *Haematococcus pluvialis* | ipiHpl | SEQ. ID No. 24 (AF082325) |
| 1-deoxyxylolose-5-phosphate (DXP) synthase derived from *Escherichia coli* | dxs | SEQ. ID No. 25 (U00096) |
| Geranylgeranyl pyrophosphate (GGPP) synthase derived from *pantoea agglomerans* | crtE | SEQ. ID No. 26 (M87280) |
| Phytoene synthase derived from *pantoea agglomerans* | crtB | SEQ. ID No. 27 (M87280) |
| Phytoene dehydrogenase derived from *pantoea agglomerans* | crtI | SEQ. ID No. 28 (M87280) |
| Lycopene β-cyclase derived from *pantoea ananatis* | crtY | SEQ. ID No. 29 (D90087) |

TABLE 4

| Gene | | Primer sequence | Restriction enzyme |
|---|---|---|---|
| ipiHpl | F | SEQ. ID No. 46 | SmaISphI |
| | R | SEQ. ID No. 47 | |
| dxs | F | SEQ. ID No. 48 | EcoR1SnaBI |
| | R | SEQ. ID No. 49 | |
| crtE | F | SEQ. ID No. 50 | BspHIEcoRI |
| | R | SEQ. ID No. 51 | |
| crtB, crtI | F | SEQ. ID No. 52 | EcoR1SacI |
| | R | SEQ. ID No. 53 | |
| crtY | F | SEQ. ID No. 54 | SalIPstI |
| | R | SEQ. ID No. 55 | |

The primer sequences and restriction enzymes used in cloning the genes listed in Table 3 are stated in Table 4. Since crtB and crtI are present as a single operon in a chromosome, a whole operon rather than individual genes was subjected PCR cloning at once.

The genes listed in Table 3 were amplified using the primers listed in Table 4 through PCR which uses a chromosome DNA in each strain including corresponding gene as a matrix. The amplified product was introduced into pTrc99A vector (Genbank accession No. M22744) (SEQ. ID No. 30) using the restriction enzymes listed in Table 4, thereby preparing the vector pT-DHB. The vector pTDHB includes all of genes encoding the enzyme associated with synthesis of β-carotene from IPP, as well as DXP synthase (dxs) gene as an enzyme used in the velocity determination process in the MEP path. Further, among the genes listed in Table 3, all genes other than dxs were introduced into pTrc99A vector using the restriction enzymes listed in Table 4, thereby preparing the vector pT-HB.

(3) Preparation of a Vector Including a Gene Encoding an Enzyme Associated with Synthesis of Retinal from β-Carotene Genes encoding an enzyme associated with synthesis of retinal from β-carotene used in the present experiment are shown in Table 5 below. As a gene encoding β-carotene monooxygenase derived from uncultured marine bacterium 66A03, SR gene which is an *Escherichia coli* codon-optimized sequence of blh was used.

TABLE 5

| Name of enzyme | Gene | Gene sequence (Genbank accession No.) |
|---|---|---|
| β-carotene monooxygenase derived from uncultured marine bacterium 66A03 | blh | SEQ. ID No. 31 (DQ065755) |
| β-carotene monooxygenase derived from uncultured marine bacterium 66A03 | SR (*Escherichia coli* codon-optimized sequence of blh) | SEQ. ID No. 32 |
| β-carotene 15,15'-monooxygenase derived from *Mus musculus* | BcmoI | SEQ. ID No. 33 (NM_021486) |
| Brp-like protein 2 derived from *Natronomonas pharaonis* ATCC35678 | brp2 | SEQ. ID No. 34 (CR936257) |
| β-carotene monooxygenase derived from *Halobacterium salinarum* ATCC700922 | Blh | SEQ. ID No. 35 (AE004437) |
| β-carotene monooxygenase derived from *Halobacterium salinarum* ATCC700922 | Brp | SEQ. ID No. 36 (AE004437) |

TABLE 6

| Gene | | Primer sequence | Restriction enzyme |
|---|---|---|---|
| SR | F | SEQ. ID No. 56 | EcoR1SpeI |
| | R | SEQ. ID No. 57 | |
| bcmo1 | F | SEQ. ID No. 58 | EcoR1SpeI |
| | R | SEQ. ID No. 59 | |
| brp2 | F | SEQ. ID No. 60 | EcoR1SpeI |
| | R | SEQ. ID No. 61 | |
| blh | F | SEQ. ID No. 62 | EcoR1SpeI |
| | R | SEQ. ID No. 63 | |
| brp | F | SEQ. ID No. 64 | EcoR1SpeI |
| | R | SEQ. ID No. 65 | |

The primer sequences and restriction enzymes used in cloning the genes listed in Table 5 are stated in Table 6. The genes listed in Table 5 were amplified using the primers listed in Table 6 through PCR which uses a chromosome DNA in each strain including a corresponding gene as a matrix. The amplified product was introduced into pT-HB vector using the restriction enzymes listed in Table 6, respectively, thereby preparing the vectors pT-HBSR, pT-HBBcmo1, pT-HBbrp2, pT-HBblh and pT-HBbrp. Such vectors pT-HBSR, pT-HBBcmo1, pT-HBbrp2, pT-HBblh and pT-HBbrp are vectors formed by introducing SR, Bcmo1, brp2, blh and brp genes into pT-HB vector, respectively, and have included all of genes encoding an enzyme associated with the synthesis of retinal through β-carotene from IPP. After cutting SR gene from pT-HBSR using SpeI, the cut gene was introduced into a corresponding part of pT-DHB, thus preparing pT-DHBSR.

EXAMPLE 2

Comparison of Different BCM(D)O Genes in Relation to Retinal Production

Retinal may be produced by introduction of BCM(D)O gene encoding β-carotene mono(di)oxygenase, which is a recombinant *Escherichia coli* producing β-carotene. The present inventors have conducted cloning of BCM(D)O gene from two bacteria, i.e., *Halobacterium* sp NRC-1 (blh and brp genes) and *Natronomonas pharaonis* (brp2 gene), as well as *Mus musculus* (Bcmo1 gene) of a vertebrate animal. The present inventors have synthesized codon-optimized BCDO gene (SR) on the basis of an amino acid sequence of uncultured marine bacterium 66A03 blh gene. BCM(D)O gene (SR) was used to prepare retinal synthetic plasmids pT-HBblh, pT-HBbrp, pT-HBbrp2, pT-HBBcmo1 and pT-HBSR, respectively. The recombinant *Escherichia coli* cell containing each of retinal plasmids was cultured in a 2YT medium including 0.5% (w/v) of glycerol and 0.2% (w/v) of arabinose as a carbon source at 29° C. for 48 hours.

Figure 3:
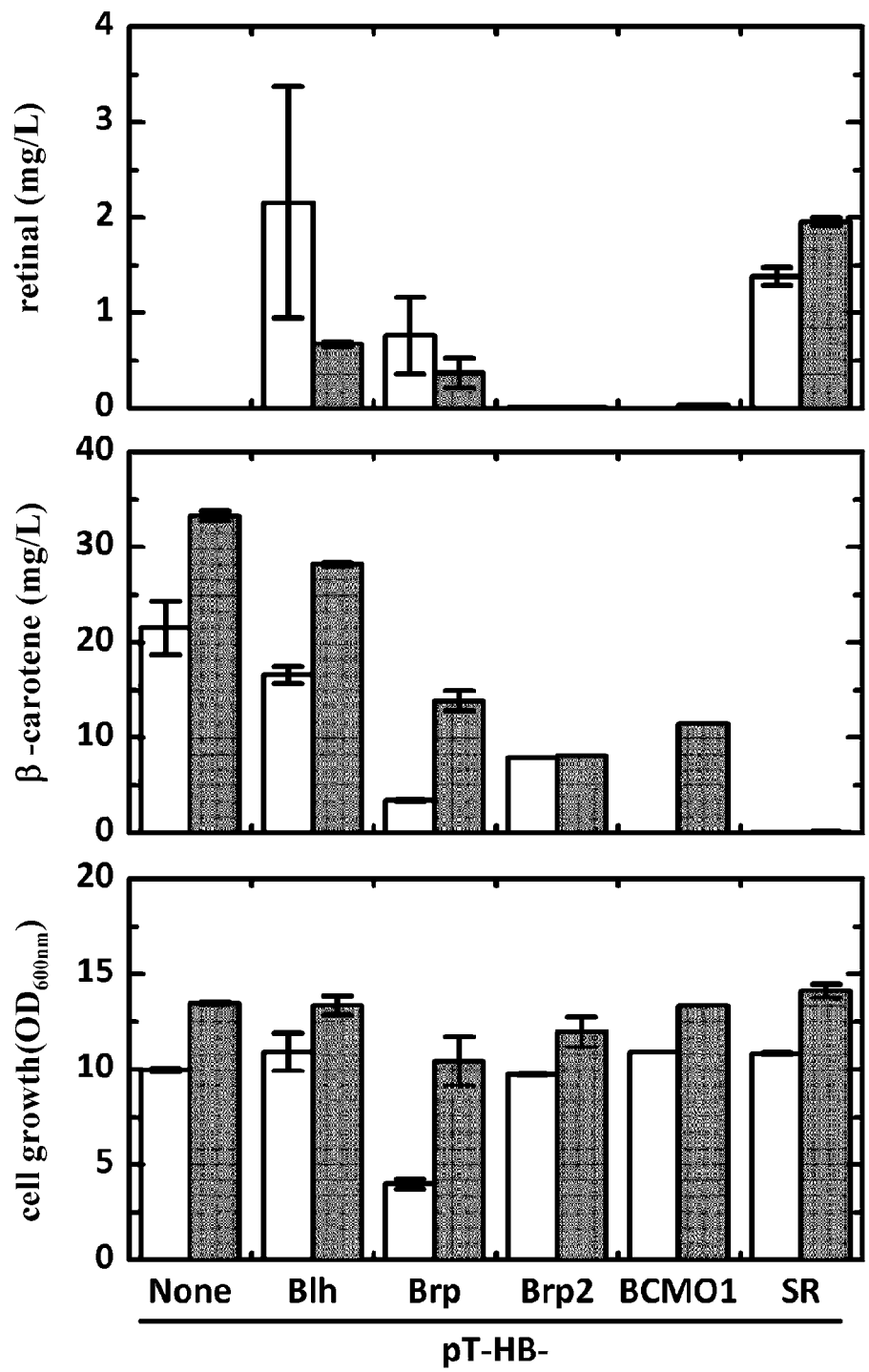
FIG. 3 illustrates production of retinal, production of β-carotene and cell growth of *Escherichia coli* including pT-HB, pT-HBblh, pT-HPbrp, pT-HBbrp2, pT-HBBCMO1 and pT-HBSR.

FIG. 3 illustrates production of retinal, production of β-carotene and cell growth of *Escherichia coli* including pT-HB, pT-HBblh, pT-HBbrp, pT-HBbrp2, pT-HBBCMO1 and pT-HBSR. More particularly, white and grey bars show numerical values at 24 hours and 48 hours, respectively.

As shown in FIG. 3, the recombinant *Escherichia coli* pT-HBblh, pT-HBbrp and pT-HBSR have produced 2.2, 0.8 or 1.4 mg/L of retinal, respectively, at 24 hours. However, retinal production by the recombinant *Escherichia coli* pT-HBblh or pT-HBbrp was reduced to 0.7 or 0.4 mg/L, respectively, at 48 hours, whereas *Escherichia coli* pT-HBSR showed a slight increase in retinal production. The decrease in retinal production after 24 hours may be caused by oxidative degradation of retinal in the cell. An amount of retinal obtained from the culture solution depends upon both intracellular synthesis and degradation of retinal.

For *Escherichia coli* including pT-HBblh or pT-HBbrp, a retinal productivity at 24 hours after culturing may be lower than a rate of degradation of the same. In the culture of *Escherichia coli* strain including pT-HBbrp2 or pT-HBBcmo1, a trace amount of retinal was detected. *Escherichia coli* without BCM(D)O gene has produced 35 mg/L of β-carotene, but did not produce retinal. Since β-carotene is a precursor just before retinal, a β-carotene consumption by BCM(D)O may be exactly proportional to the retinal productivity if there was retinal degradation. β-carotene remained in a culture solution of *Escherichia coli* including BCM(D)O other than SR, therefore, β-carotene cleavage activity of SR was expected to be the highest level among tested BCM(D)O. Accordingly, in an additional experiment, SR enzyme was adopted for retinal production. The cell growth did not come under the influence of over-expression of BCM(D)O gene except for *N. pharaonis* brp gene exhibiting delayed cell growth.

EXAMPLE 3

Gene Manipulation into MEP and MVA Paths for Supplying a Building Block

Retinal building blocks, that is, IPP and DMAPP may be synthesized in *Escherichia coli* through an inherent MEP path and a foreign MVA path (FIG. 1).

It was reported that synthesis of 1-deoxy-d-xylolose-5-phosphate (DXP) is an important velocity restriction process in the MEP path. Therefore, over-expression of DXP synthase (to be encoded by dxs) increased production of lycopene and β-carotene in previous inventions of the present inventors. By introducing dxs gene into before the MEP path among pT-HBSR, pT-DHBSR was prepared.

Figure 4:
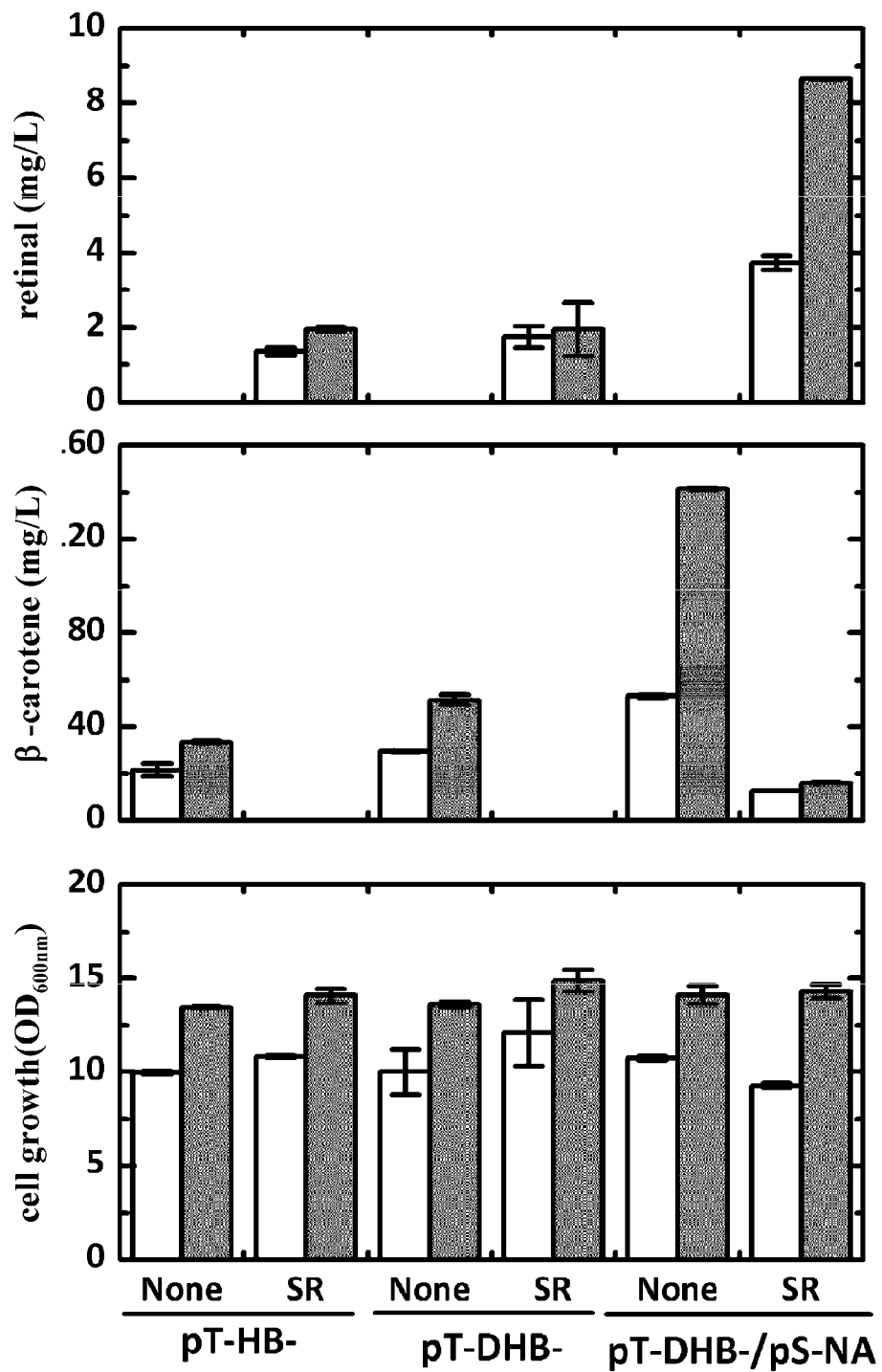
FIG. 4 illustrates production of retinal, production of β-carotene and cell growth of *Escherichia coli* including pT-HB, pT-HBSR, pT-DHB and pT-DHBSR, as well as *Escherichia coli* including pT-DHB or pT-DHBSR together with pS-NA as an MVA path plasmid.

FIG. 4 illustrates production of retinal and β-carotene, and cell growth of *Escherichia coli* including pT-HB, pT-HBSR, pT-DHB and pT-DHBSR, as well as *Escherichia coli* including pT-DHB or pT-DHBSR together with pS-NA as an MVA path plasmid. More particularly, white and grey bars show numerical values at 24 hours and 48 hours, respectively.

Figure 2:
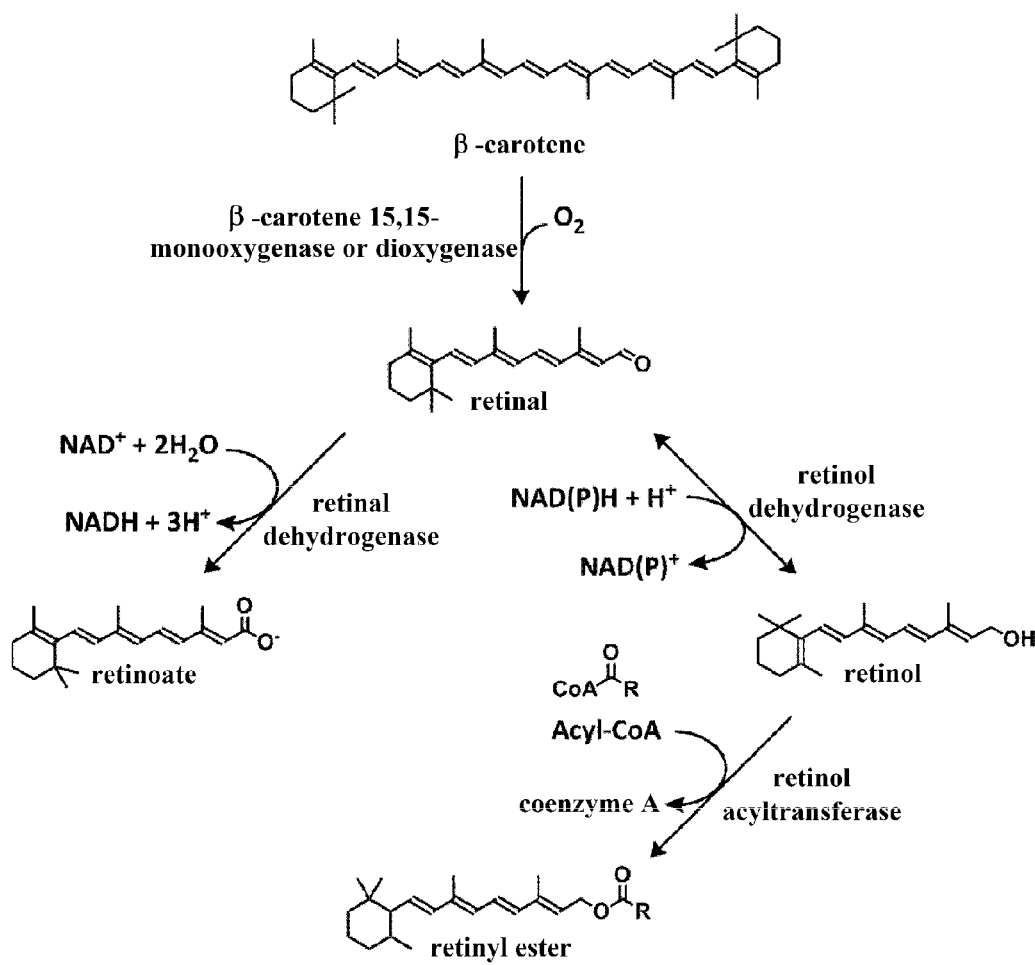
FIG. 2 illustrates retinoid conversion of β-carotene into retinoid including retinal, retinol, retinoic acid and retinyl ester.

As shown in FIG. 4, the retinal productivity of *Escherichia coli* pT-DHBSR was a little higher than that of *Escherichia coli* pT-DHB at 24 hours, while being substantially similar to the same at 48 hours. However, β-carotene production by *Escherichia coli* pT-DHB was increased by about 1.5 times due to over-expression of dxs, as compared to *Escherichia coli* pT-HB. It is known that a foreign MVA path in *Escherichia coli* considerably increases production of isoprenoid by providing sufficient amounts of IPP and DMAPP building blocks. *Escherichia coli* pT-DHBSR/pS-NA including an additional foreign MVA path have produced 8.7 mg/L of retinal for 48 hours, which is 4 times higher than the productivity of *Escherichia coli* pT-DHBSR. For an *Escherichia coli* strain including SR gene, β-carotene did not remain or slightly remained in the cell. This condition is presumed due to an effective cleavage reaction of β-carotene by SR. There was a considerable difference between an amount of β-carotene (a substrate) consumption and an amount of produced retinal (a product). This difference may be due to the presence of a cellular reaction to metabolize retinal in *Escherichia coli* as well as biological degradation of retinal. Accordingly, formation of an alternative retinoid derived from retinal by any enzyme in *Escherichia coli* may be under consideration. Since the retinal can be converted into retinol, retinoic acid and retinyl ester by cell-enzyme reaction (FIG. 2), retinal derivatives contained in an *Escherichia coli* culture solution were subjected to analysis. The analysis results showed that retinal derivatives other than retinoic acid were formed. According to further experiments, production of retinal, retinol and retinyl acetate was determined.

EXAMPLE 4

Effects of *Escherichia coli* Strain, Culture Conditions and Carbon Source in Relation to Retinoid Production (1) Strain With regard to production of retinoid including retinal, retinol and retinyl acetate, effects of *Escherichia coli* strains were investigated. Five *Escherichia coli* strains including pT-DHBSR and pS-NA, that is, MG1655, DH5α, XL1-Blue, S17-1 and BL21 (DE3) were used to produce retinoid. Table 7 shows characteristics of six *Escherichia coli* strains including the foregoing five strains.

TABLE 7

| E. coli strain | Details |
| --- | --- |
| MG1655 | K12, wild type |
| DH5α | F−, φf80dlacZΔM15, Δ(lacZYA-argF)U169, deoR, recA1endA1, hsdR17($r_K^-m_K^+$), phoA, supE44, λ−, thi-1, gyrA96, relA1 |
| XL1-Blue | hsdR17, supE44, recA1, endA1, gyrA46, thi, relA1, lac/F'[proAB+, lacI$^q$, lacZΔM15::Tn10(tet$^r$)] |
| S17-1 | recA pro hsdR RP4-2-Tc::Mu-Km::Tn7 |
| BL21 (DE3) | F−, ompT, hsdS$_B$($r_B^-m_B^-$), gal(lcI857, ind1, Sam7, nin5, lacUV5-T7 gene1), dcm(DE3) |
| BW25113 | Δ(araD-araB)567, ΔlacZ4787(::rrnB-3), lambda−, rph-1, Δ(rhaD-rhaB)568, hsdR514 |

Figure 5:
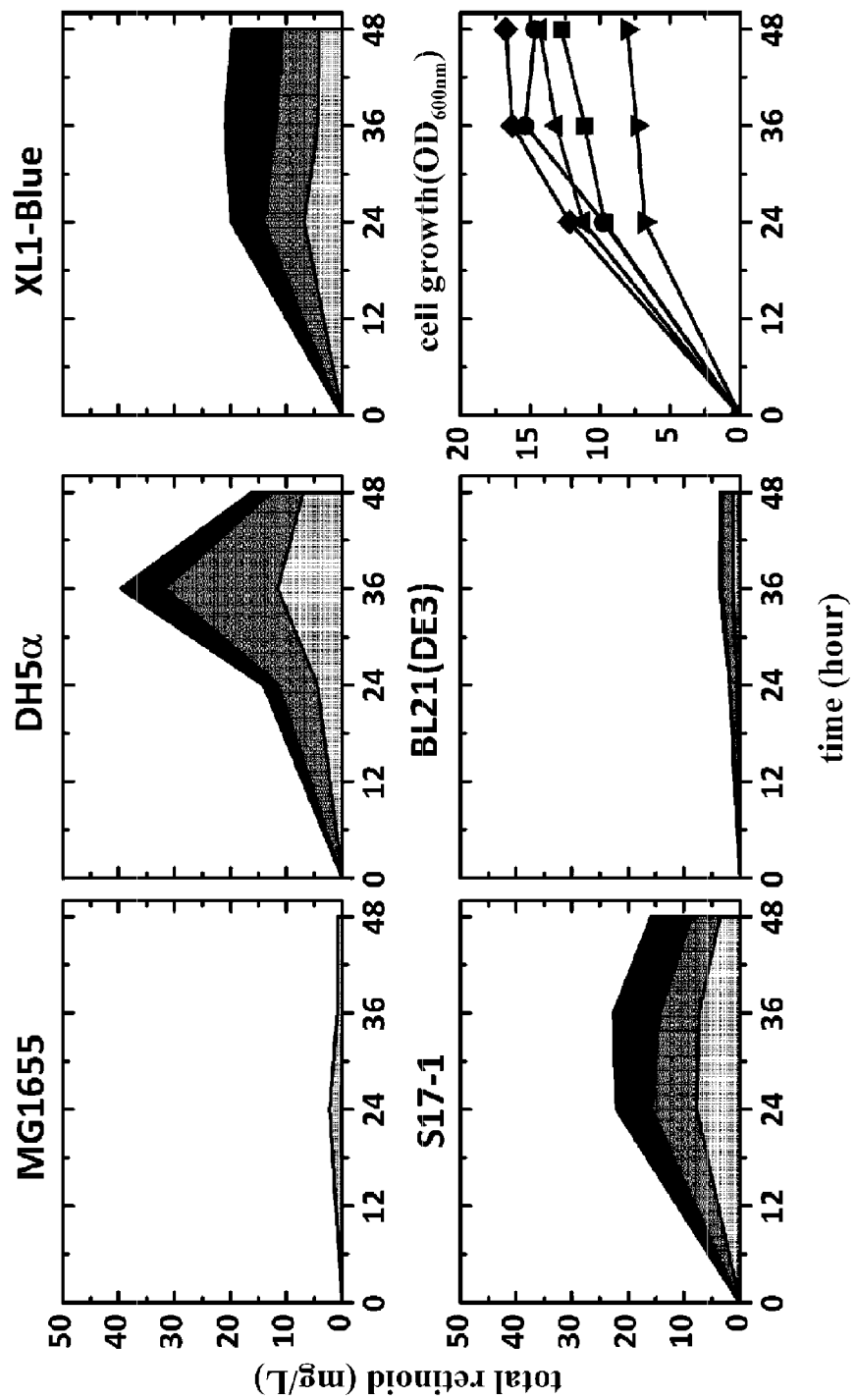
FIG. 5 illustrates retinoid production and cell growth by a variety of *Escherichia coli* strains including pT-DHBSR and pS-NA.

FIG. 5 illustrates retinoid production and cell growth of five *Escherichia coli* strains, respectively, of which each has pT-DHBSR and pS-NA. Culturing was conducted in a 2YT medium including 0.5% (w/v) of glycerol and 0.2% (w/v) of arabinose at 29° C. for 48 hours. Retinal, retinol and retinyl acetate are represented by bright grey, dark grey and black colors, respectively. Also, in case of cell growth, MG1655, DH5α, XL1-Blue, S17-1 and BL21 (DE3) are represented by ■, ●, ▲, ▼ and ♦, respectively.

As shown in FIG. 5, *Escherichia coli* DH5α has produced 40 mg/L, that is, the largest amount of retinoid at 36 hours, and *Escherichia coli* S17-1 and XL1-Blue have produced about 22 mg/L, that is, the second largest amount of retinoid. However, from *Escherichia coli* MG1655 and BL21 (DE3), only a trace amount of retinoid was produced. Therefore, *Escherichia coli* DH5α was adopted as a strain for retinoid production.

(2) Culture Conditions

With regard to production of retinoid, effects of dissolved oxygen were investigated with difference test volumes in a test tube having a diameter of 30 mm.

Figure 6:
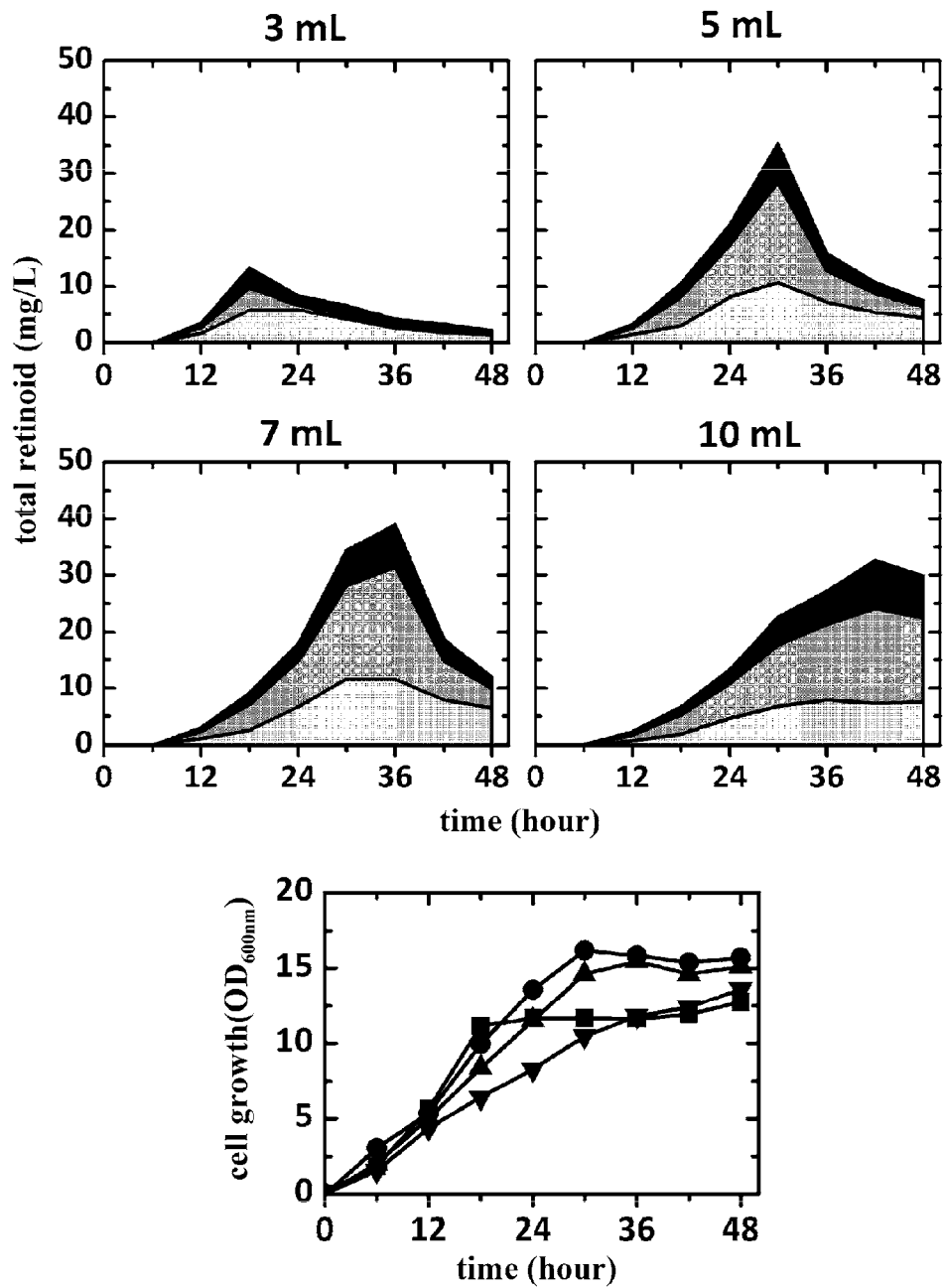
FIG. 6 illustrates retinoid production and cell growth of *Escherichia coli* including pT-DHBSR and pS-NA depending on a test volume of a culture solution.

FIG. 6 illustrates retinoid production and cell growth of *Escherichia coli* including pT-DHBSR and pS-NA depending on test volume. Referring to FIG. 6, retinal, retinol and retinyl acetate are represented by bright grey, dark grey and black colors, respectively. Also, in case of cell growth, test volumes of 3 mL, 5 mL, 7 mL and 10 mL are represented by ■, ■, ▲ and ▼, respectively. Culturing was conducted in a 2YT medium including 0.5% (w/v) of glycerol and 0.2% (w/v) of arabinose at 29° C. for 48 hours.

As shown in FIG. 6, it was found that retinoid production more early reached the maximum level at a small test volume (corresponding to highly dissolved oxygen), and the production was deemed to more quickly decrease due to oxidative degradation. With 10 mL of test volume, both of cell growth and retinoid production were delayed, while degradation of the product was observed by a small extent. It was found that the optimum test volume for retinoid production is 7 mL.

Figure 7:
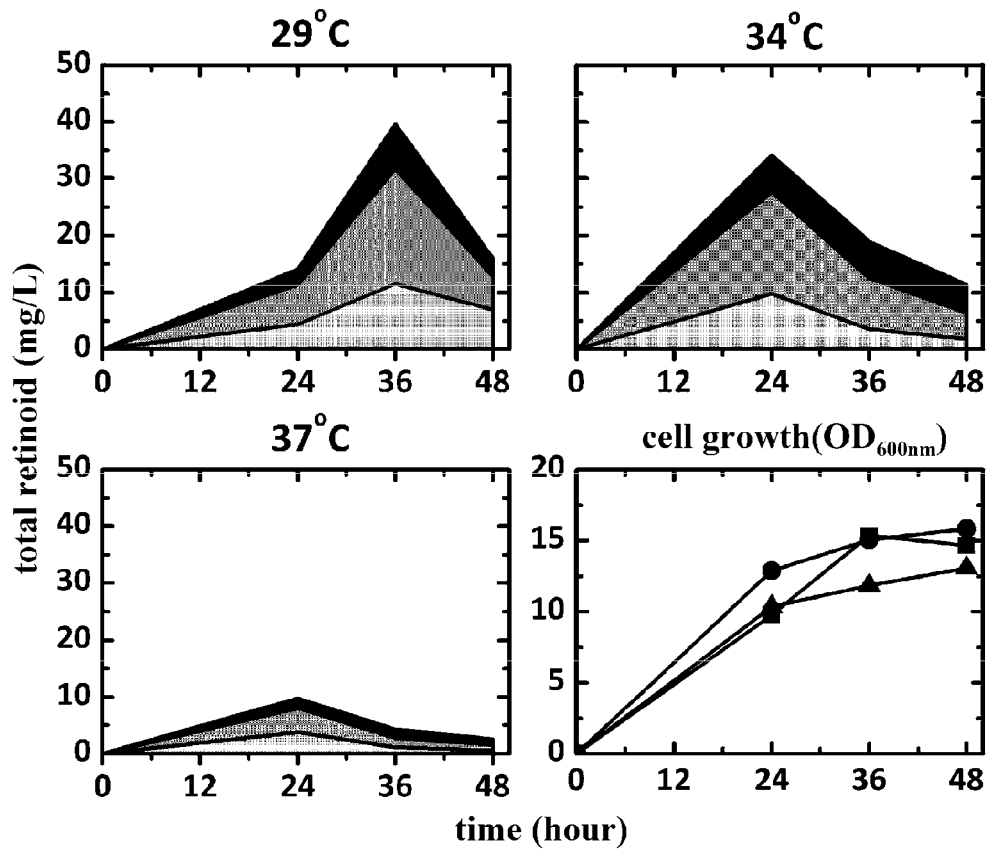
FIG. 7 illustrates retinoid production and cell growth of *Escherichia coli* including pT-DHBSR and pS-NA depending on a culture temperature.

Further, the retinoid production depending upon the temperature was investigated. FIG. 7 illustrates retinoid production and cell growth of *Escherichia coli* including pT-DHBSR and pS-NA depending on a culture temperature. Referring to FIG. 7, retinal, retinol and retinyl acetate are represented by bright grey, dark grey and black colors, respectively. Also, in case of cell growth, culture temperatures of 29° C., 34° C. and 37° C. are represented by ■, ● and, respectively. Culturing was conducted in a 2YT medium including 0.5% (w/v) of glycerol and 0.2% (w/v) of arabinose at 29° C., 34° C. and 37° C., respectively, for 48 hours.

As shown in FIG. 7, the retinoid production has come under an influence of culture temperature and the highest production was accomplished at 29° C.

(3) Carbon Source

Effects of different carbon sources upon production of retinoid were compared.

Figure 8:
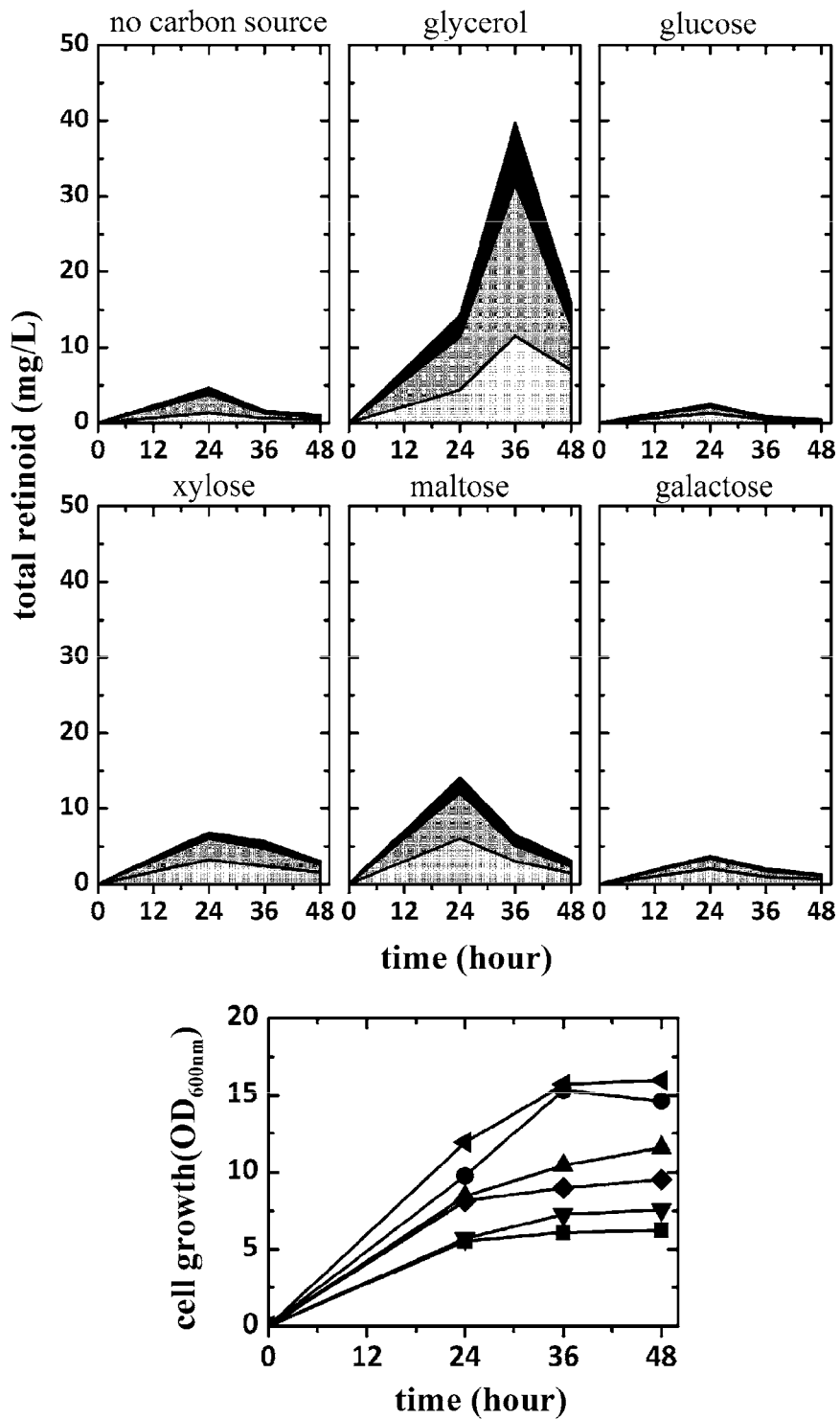
FIG. 8 illustrates retinoid production and cell growth of *Escherichia coli* including pT-DHBSR and pS-NA depending on a carbon source.

FIG. 8 illustrates retinoid production and cell growth of *Escherichia coli* including pT-DHBSR and pS-NA depending on the carbon source. Referring to FIG. 8, retinal, retinol and retinyl acetate are represented by bright grey, dark grey and black colors, respectively. Also, in case of cell growth, no carbon source, and the carbon sources of glycerol, glucose, xylose, maltose and galactose are represented by ■, ●, ▲, ▼, ♦ and, respectively. Culturing was conducted in a 2YT medium including 0.2% (w/v) of arabinose and 0.5% (w/v) of glycerol, glucose, xylose, maltose or galactose, at 29° C. for 48 hours.

As shown in FIG. 8, it was found that glycerol was the best carbon source for retinoid production. When glucose or galactose was used as the carbon source, the retinoid productivity was lower than that in case where the carbon source was not used.

Next, effects of a concentration of glycerol upon the retinoid production and cell growth were investigated. *Escherichia coli* DH5α(pT-DHBSR/pSNA) was grown in a 2YT medium including glycerol in a range of 0.0% to 2.0% (w/v), at 29° C.

Figure 9:
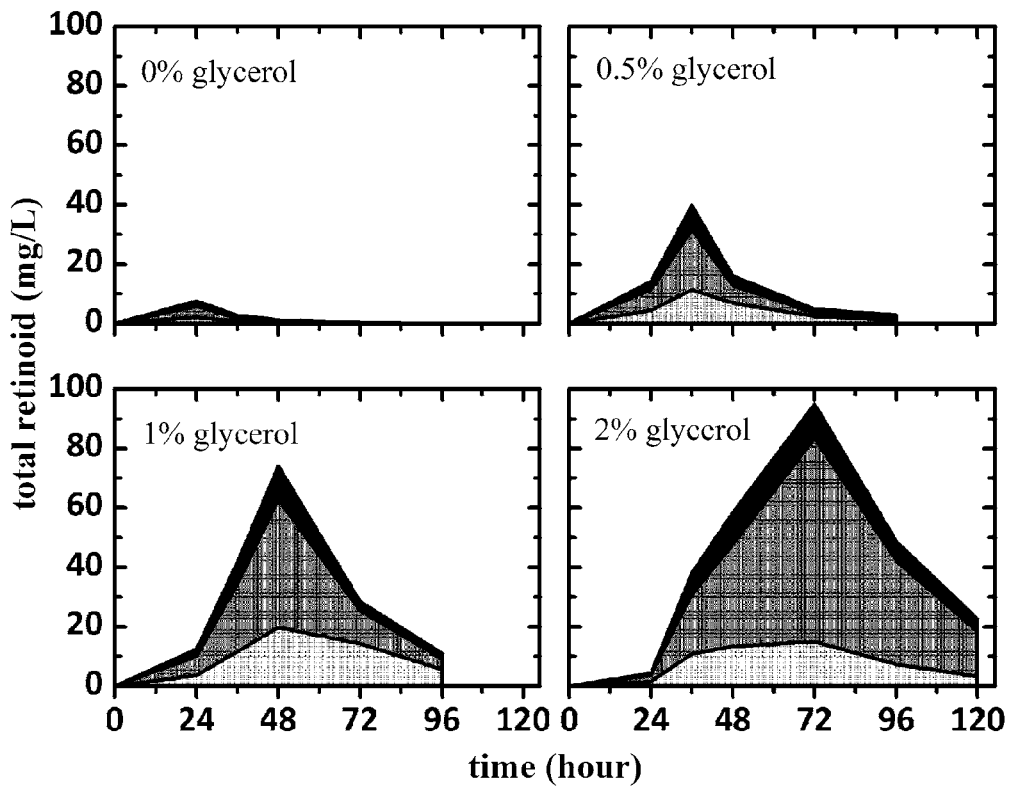
FIGS. 9 and 10 illustrate retinoid production and cell growth of *Escherichia coli* including pT-DHBSR and pS-NA depending on a concentration of glycerol as a carbon source, respectively.

FIG. 9 illustrates production of retinoids (retinal, retinol and retinyl acetate) of *Escherichia coli* including pT-DHBSR and pS-NA. Retinal, retinol and retinyl acetate are represented by bright grey, dark grey and black colors, respectively.

Figure 10:
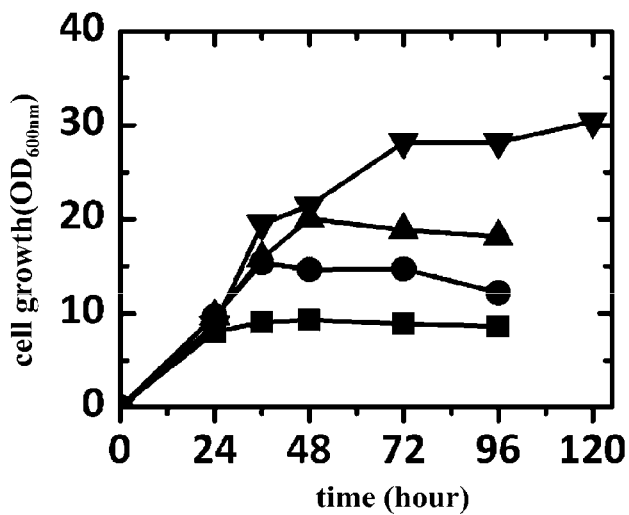

FIG. 10 illustrates cell growth of *Escherichia coli* including pT-DHBSR and pS-NA. Given glycerol concentrations of 0%, 0.5%, 1% and 2% are represented by ■, ●, ▲ and ▼, respectively.

As shown in FIGS. 9 and 10, the cell growth was proportional to the glycerol concentration and increased. With the glycerol concentration of 0.5, 1.0 and 2.0% (w/v), the cell growth has become stagnate at 36, 48 and 72 hours, respectively. At the above time, the maximum retinoid productivity was accomplished and, thereafter, the productivity was considerably reduced during stagnation. It can be seen that the retinoid production generally increases after 24 hours. The retinoid productivity was about 95 mg/L, the highest level, at 2.0% (w/v) of glycerol among various glycerol concentrations, which is substantially 2.4 times higher than the maximum retinoid productivity at 0.5% (w/v) of glycerol. An increase in glycerol concentration delayed the stagnation while extending a period of retinoid production.

From all culture solutions, it was observed that the retinoid production was extremely reduced during stagnation of the cell growth, and this condition is deemed to be caused by discontinued production of retinoid during stagnation and intracellular oxidative degradation of the same.

(4) Culture in the Presence of Dodecane

Strains containing transformed pT-DHBSR/pSNA were used for six strains listed in Table 7. After adding 1 mL of dodecane to 5 ml of medium, culturing was conducted according to such conditions as described in "bacteria strain and culture conditions." The medium used herein was a 2YT medium including 0.2% (w/v) of arabinose and 0.5% (w/v) of glycerol added thereto.

Figure 11:
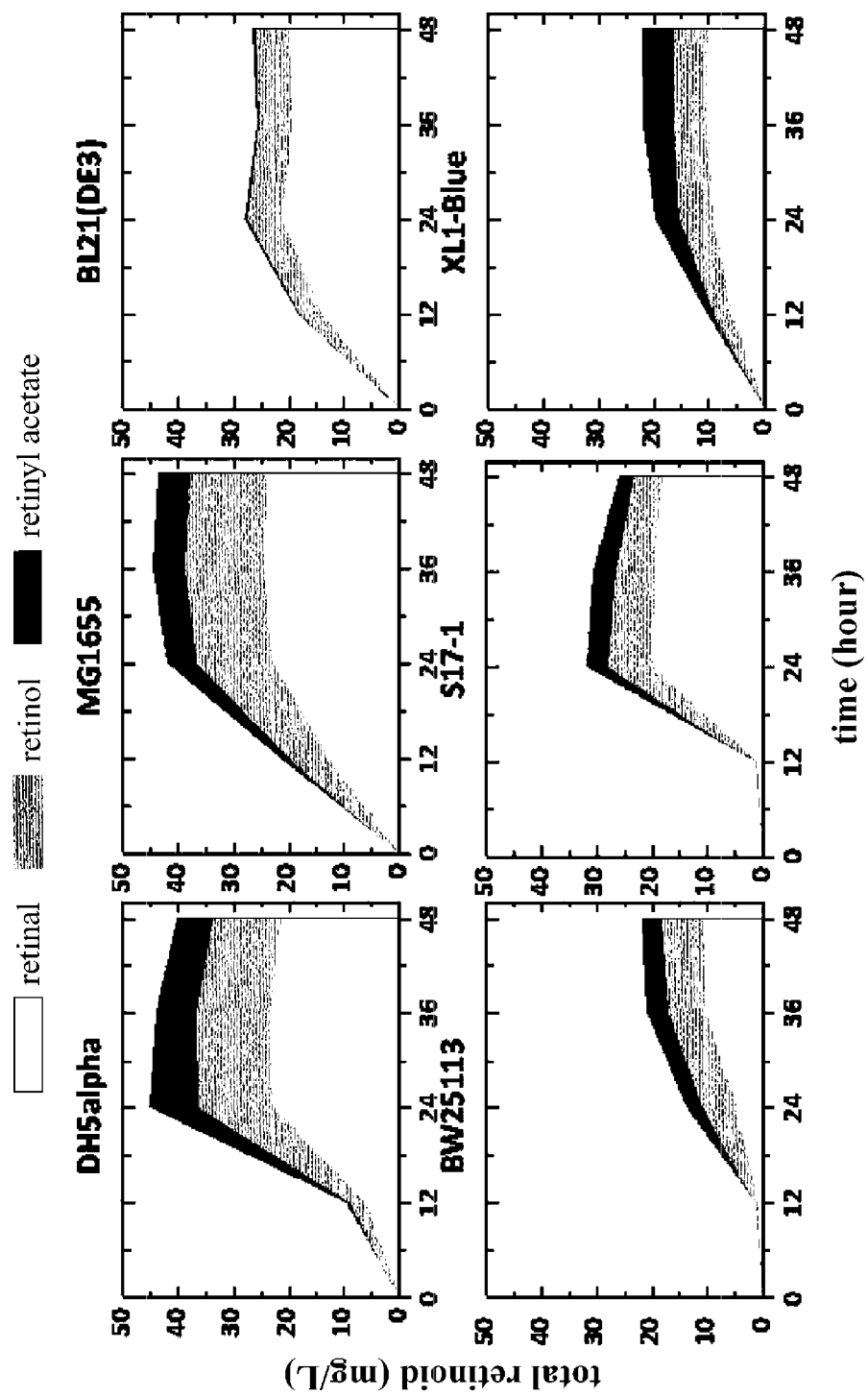
FIGS. 11 and 12 illustrate results of retinoid production and cell growth by a variety of *Escherichia coli* strains in the presence of dodecane, respectively.

FIG. 11 illustrates results of the retinoid production depending on different *Escherichia coli* strains for retinoid production. As shown in FIG. 11, DH5α and MG1655 showed the largest amount of retinoid production. For MG1655, the cell growth and retinoid productivity were increased, as compared to no addition of dodecane. A cell growth rate and a rate of increasing retinoid productivity for MG1655 were obviously faster than DH5α. BL21 (DE3) strain showed a still high cell growth but had scarcely any production of retinyl acetate. Consequently, it was determined that DH5α and MG1655 among six strains are relatively suitable, as compared to other strains.

Figure 12:
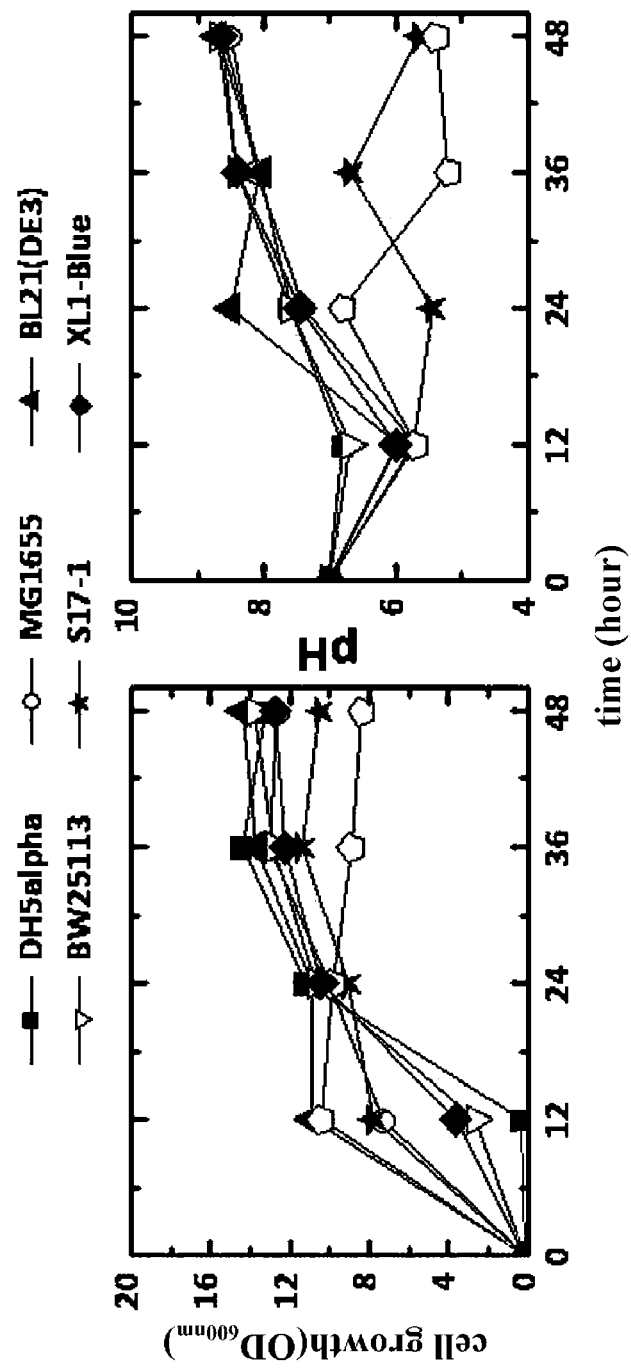

FIG. 12 illustrates results of growth of strains for retinoid production in the presence of dodecane.

Figure 13:
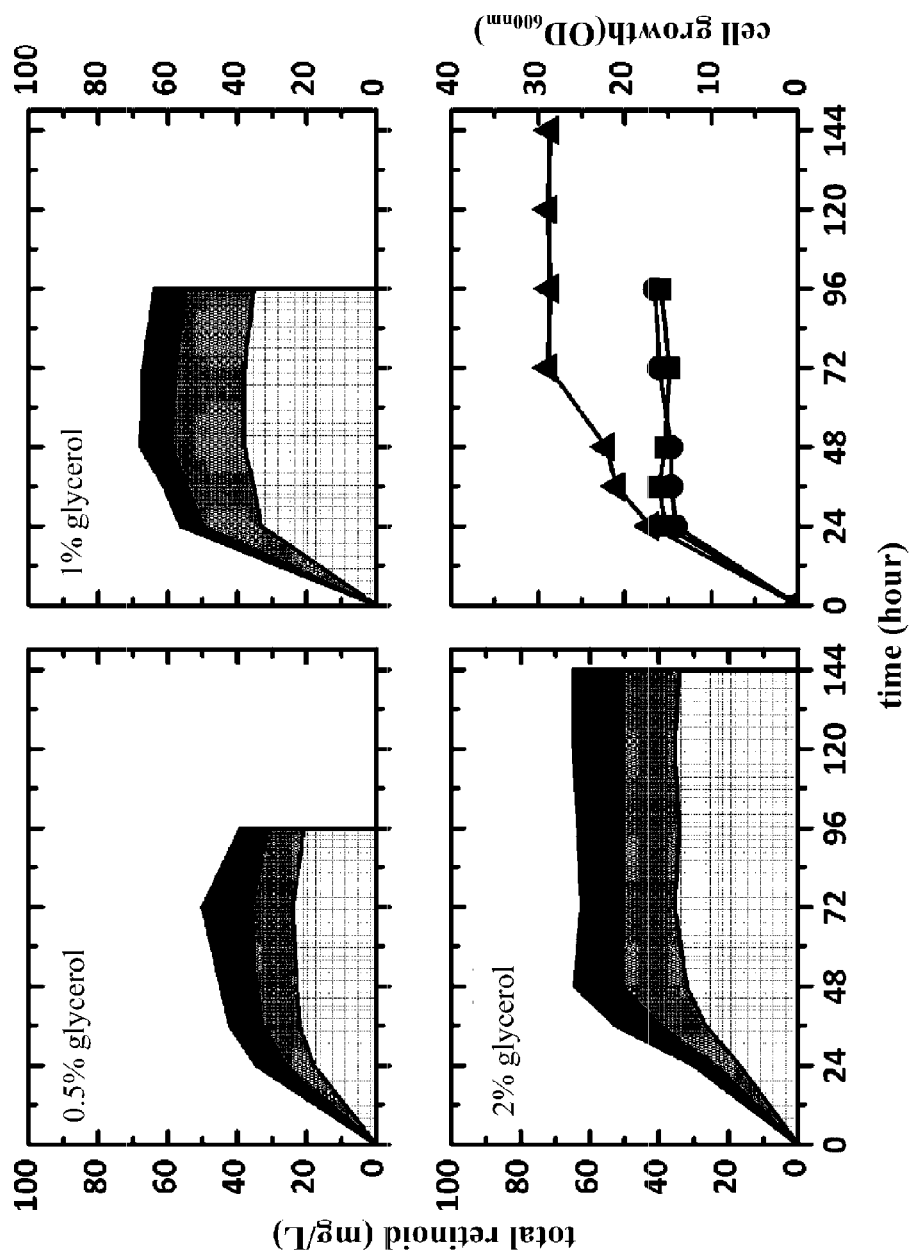
FIG. 13 illustrates retinoid production and cell growth of *Escherichia coli* (pT-DHBSR/pS-NA) depending on a concentration of glycerol as a carbon source in a 2-phase culture system including 1 mL of dodecane in 5 ml of culture medium.

FIG. 13 illustrates results of retinoid production and growth in the presence of dodecane, depending on the concentration of glycerol as a carbon source.

EXAMPLE 5

2-Phase Culture Using Dodecane for In-Situ Extraction of Retinoid

In order to prevent intracellular degradation of retinoid, a 2-phase culture method was conducted using a hydrophobic solvent, that is, dodecane, in order to perform in-situ extraction of retinoid from cells. Dodecane was selected since it has a low toxicity to *Escherichia coli* I, a high hydrophobicity (log $P_{o/w}$, 6.6) for extracting hydrophobic retinoid, and low volatile properties not to cause evaporation loss.

In the present example, 1 mL of dodecane was added to 5 ml of culture solution. FIG. 13 illustrates retinoid production and cell growth of *Escherichia coli* (pT-DHBSR/pS-NA) in a 2-phase culture system including 1 mL of dodecane in 5 ml of culture medium. With regard to retinoid production, retinal, retinol and retinyl acetate are represented by bright grey, dark grey and black colors, respectively. In the case of cell growth, given glycerol concentrations of 0.5%, 1% and 2% are represented by ■, ● and ▲, respectively.

Retinoid was extracted into the dodecane phase while an insignificant amount of retinoid was detected in the culture solution and cell mass (data not shown). As a result, the retinoid productivity was measured from the dodecane phase. As shown in FIG. 13, in-situ extraction could minimize intracellular degradation of retinoid by dodecane. The retinoid among the dodecane phase was deemed to be relatively stable and remained without significant oxidative degradation thereof. As comparing with the results shown in FIGS. 9 and 10 (without addition of dodecane), the retinoid production was remarkably increased even at 24 hours in case of adding the dodecane. Further, the cell growth did not come under an influence of the dodecane addition while the retinoid production was not decreased during stagnation. However, in the culture using 2% (w/v) glycerol, the retinoid production was not so higher than that in case of using 1% (w/v) glycerol, even though the cell growth was remarkably increased in proportion to an increase in glycerol concentration from 1% (w/v) to 2% (w/v). When the volume of dodecane addition is 1 mL, it is insufficient to conduct effective in-situ extraction of retinoid in the culture using 2% (w/v) of glycerol.

Figure 14:
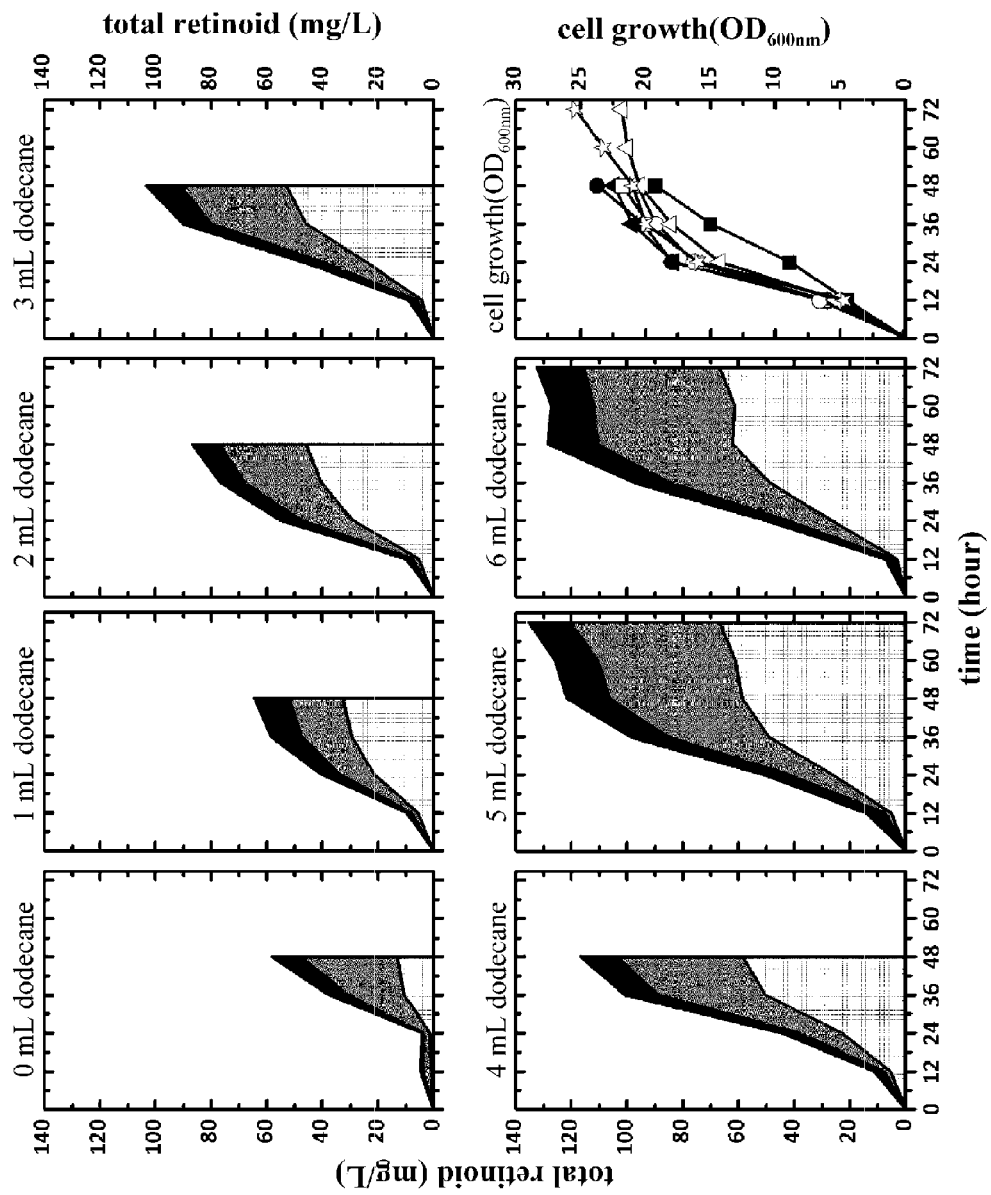
FIG. 14 illustrates retinoid production and cell growth of *Escherichia coli* (pT-DHBSR/pS-NA) in a 2-phase culture system depending on the volume of dodecane.

In order to investigate effects of the volume of dodecane addition on the retinoid production and cell growth, 1 mL to 5 mL of dodecane was initially added to a culture solution including 2% (w/v) of glycerol (FIG. 14).

FIG. 14 illustrates retinoid production and cell growth of *Escherichia coli* (pT-DHBSR/pS-NA) in a 2-phase culture system, depending on the volume of dodecane. With regard to the retinoid production, retinal, retinol and retinyl acetate are represented by bright grey, dark grey and black colors, respectively. In case of cell growth, volumes of overlaying dodecane of 0 mL, 1 mL, 2 mL, 3 mL, 4 mL, 5 mL and 6 mL are represented by ■, ●, ▲, □, ○, △ and ☆, respectively.

Figure 15:
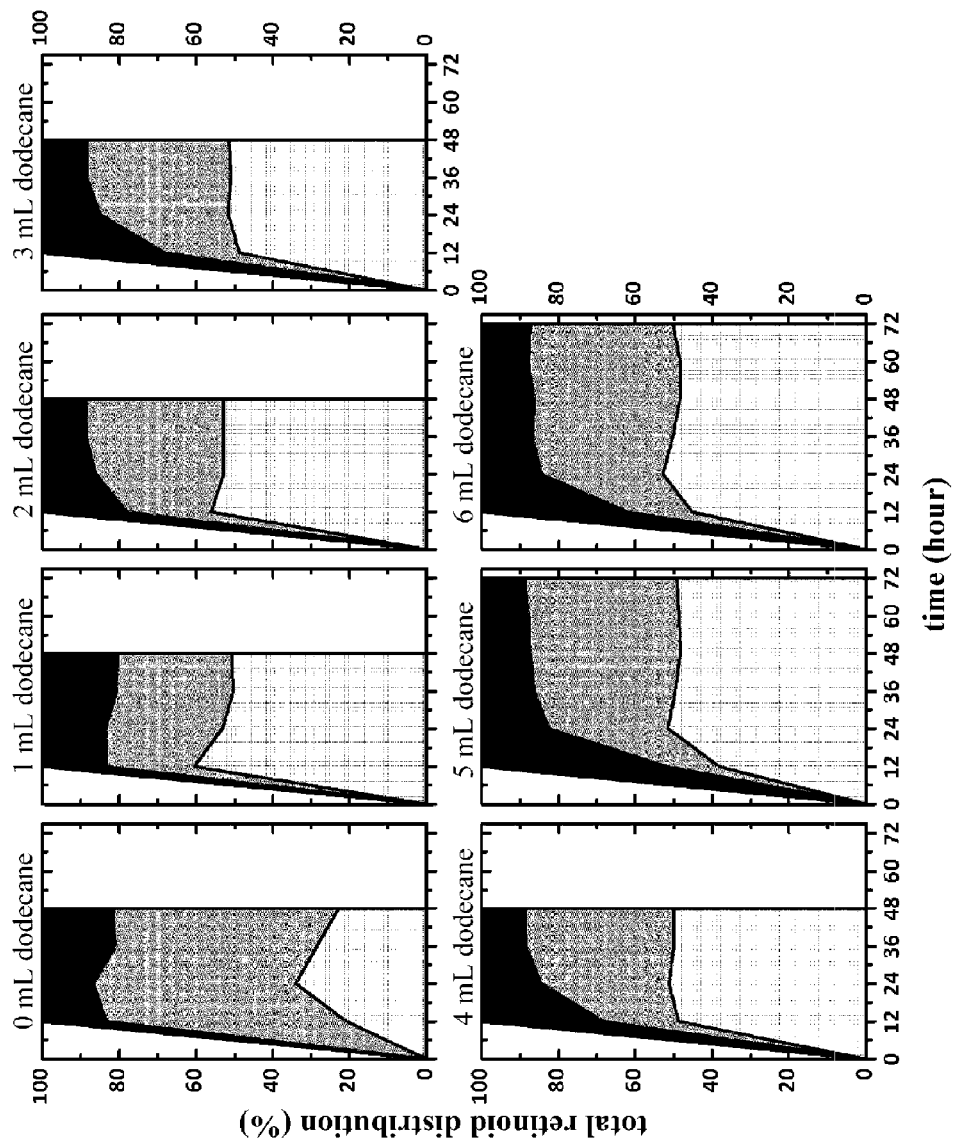
FIG. 15 illustrates distributions of retinoid depending on a culturing time of *Escherichia coli* (pT-DHBSR/pS-NA) and a volume of dodecane in a 2-phase culture system, which are represented in terms of percentages of individual constituents to total retinoid.

FIG. 15 illustrates a distribution of retinoid depending on culturing time and volume of dodecane, in terms of percentages of individual constituents to total retinoid. Retinal, retinol and retinyl acetate are represented by bright grey, dark grey and black colors, respectively.

As shown in FIGS. 14 and 15, production of overall retinoids was improved according to an increase in the volume of dodecane addition. In 72 hours culture using 5 mL of dodecane, the highest retinoid productivity of 136 mg/L was obtained, which is about 2 times higher value than that (65 mg/L) in case where 1 mL of dodecane is used. Meanwhile, in 72 hours-extended culture using 5 mL of dodecane, the retinoid productivity did not further increase but the highest level was maintained without degradation of the retinoid (data not shown). By adding 2 mL of dodecane to the culture solution at 0, 24 and 48 hours, a whole volume of dodecane addition was increased to 6 mL. In the culture using 6 mL of added dodecane, the total retinoid productivity did not increase, as compared to the culture using 5 mL of dodecane. Likewise, even in the culture using 6 mL of initially added dodecane, the retinoid productivity did not increase (data not shown). The cell growth in all of culture solutions including dodecane was slightly higher than that in case of not using dodecane (FIG. 14).

FIG. 15 illustrates a distribution of produced retinoids depending on the volume of dodecane addition. With regard to ratios of obtained retinal and retinol, there is a considerable difference in retinoid distributions between addition of dodecane and no addition of dodecane. A ratio of retinal in retinoid at 48 hours was about 51% (w/v) in the dodecane-added culture and 23% (w/v) in the culture without adding dodecane. Likewise, a ratio of retinol ranged from 30 to 39% in the dodecane-added culture and was 59% in the culture without adding dodecane. Accordingly, the addition of dodecane may increase a ratio of retinal while reducing a ratio of retinol. In consideration of the order of reactions for formation of retinol from retinal in a cell, retinal is deemed to be extracted from the cell before conversion of the same into retinol by dodecane. Further, a ratio of retinyl acetate at 48 hours was less than 20% in both of the cultures with and without addition of dodecane, which is relatively lower than the ratios of retinal and retinol. In the culture with addition of dodecane, the ratio of retinyl acetate is reduced as the culturing time is extended and this indicates that activity of cells for forming retinyl acetate is reduced during culturing. Consequently, adding dodecane has prevented a decrease of retinoid production during stagnation of the cell growth, while improving the retinoid production.

The in-situ extraction of retinoid according to the present invention does not need lysozyme used for degrading a cell wall. Retinoid (C20, isoprenoid molecule) may be efficiently released from the cell without loss of the cell wall. In 2-phase culture for production of retinoid, β-carotene must be continuously maintained in the cell since it is a direct precursor of the retinoid. If β-carotene is extracted from the dodecane phase, it can be cut by BCD(M)O placed in cytosol.

Figure 16:
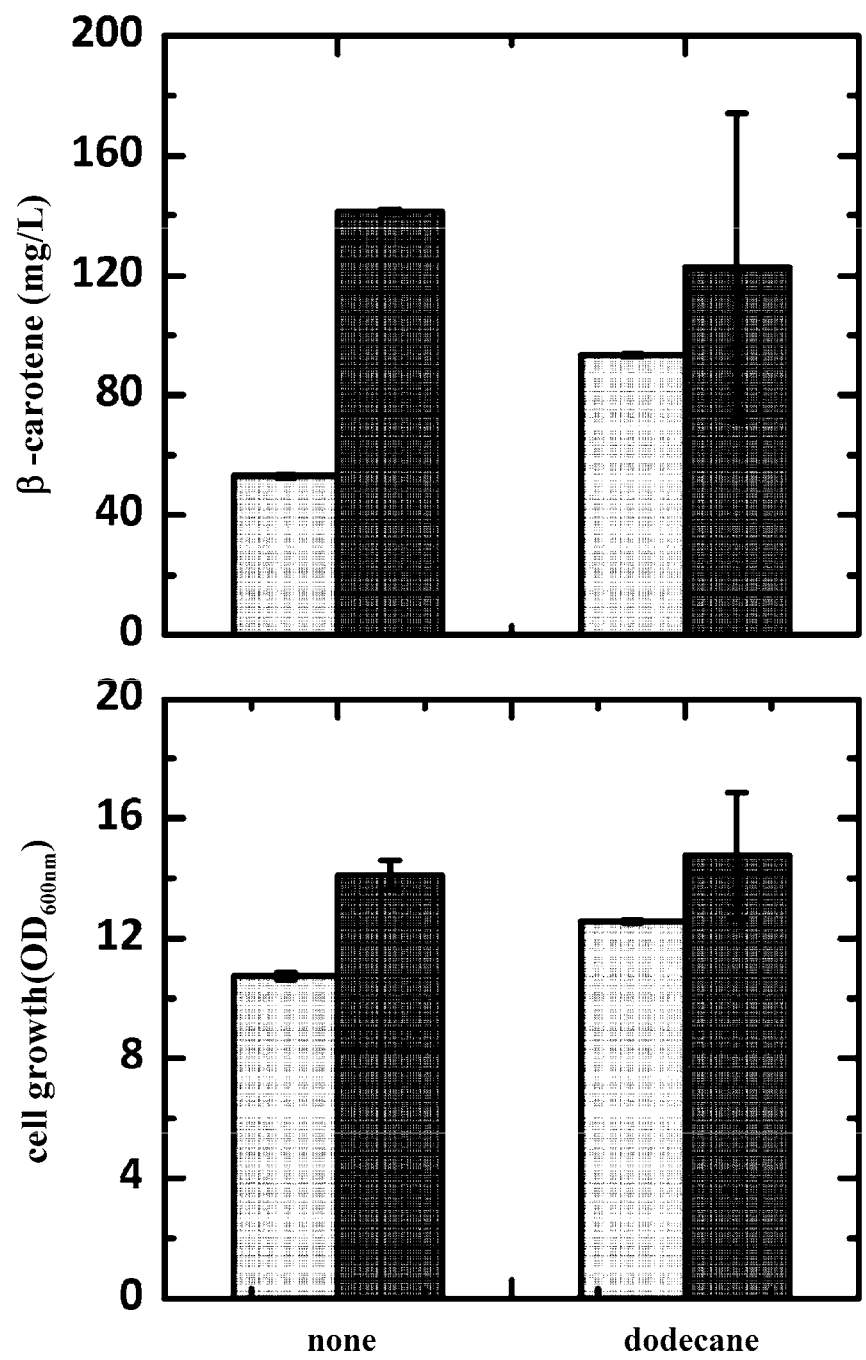
FIG. 16 illustrates effects of dodecane addition upon production of beta-carotene and cell growth of *Escherichia coli* including pT-DHB and pS-NA.

Due to a size of molecule, β-carotene can neither be released from the cell nor extracted by dodecane, therefore, can be continuously maintained in the cell during 2-phase culture of β-carotene (FIG. 16).

FIG. 16 illustrates effects of dodecane addition depending on β-carotene production and cell growth of $Escherichia$ $coli$ including pT-DHB and pS-NA. Culturing was conducted in 5 ml of 2YT medium including 0.5% (w/v) of glycerol and 0.2% (w/v) of arabinose at 29° C. for 48 hours while adding 1 mL of dodecane to the medium. Grey and black bars indicated 24 hours and 48 hours, respectively.

As shown in FIG. 16, an insignificant amount of β-carotene was detected in the dodecane phase and a whole β-carotene has been almost retained in the cell. There was not a noticeable difference in β-carotene production and cell growth between cultures with and without addition of dodecane.

In the culture with addition of 5 mL of dodecane, a total 122 mg/L of retinoid productivity was attained at 48 hours. However, in the culture without addition of dodecane, only half of the above productivity (60 mg/L) was obtained at the same time period. Accordingly, the dodecane-added 2-phase culture system may be appropriately applied to an alternative transformation system to produce small lipophilic molecules.

EXAMPLE 6

Production of Retinoid in Medium Including Lipophilic Substance

The present example was performed to identify as to whether a variety of lipophilic substances have effects of increasing retinoid production.

(1) Production of Retinoid in Medium Including Alkane

A strain DH5α including transformed pT-DHBSR/pSNA (DH5α(pT-DHBSR/pSNA)) was used, and after adding 5 mL of each of octane, decane, dodecane and tetradecane to 5 ml of medium, culturing was conducted according to such conditions as described in "Bacteria strain and culture conditions." The medium used herein was a 2YT medium including 0.2% (w/v) of arabinose and 2.0% (w/v) of glycerol added thereto.

Figure 17:
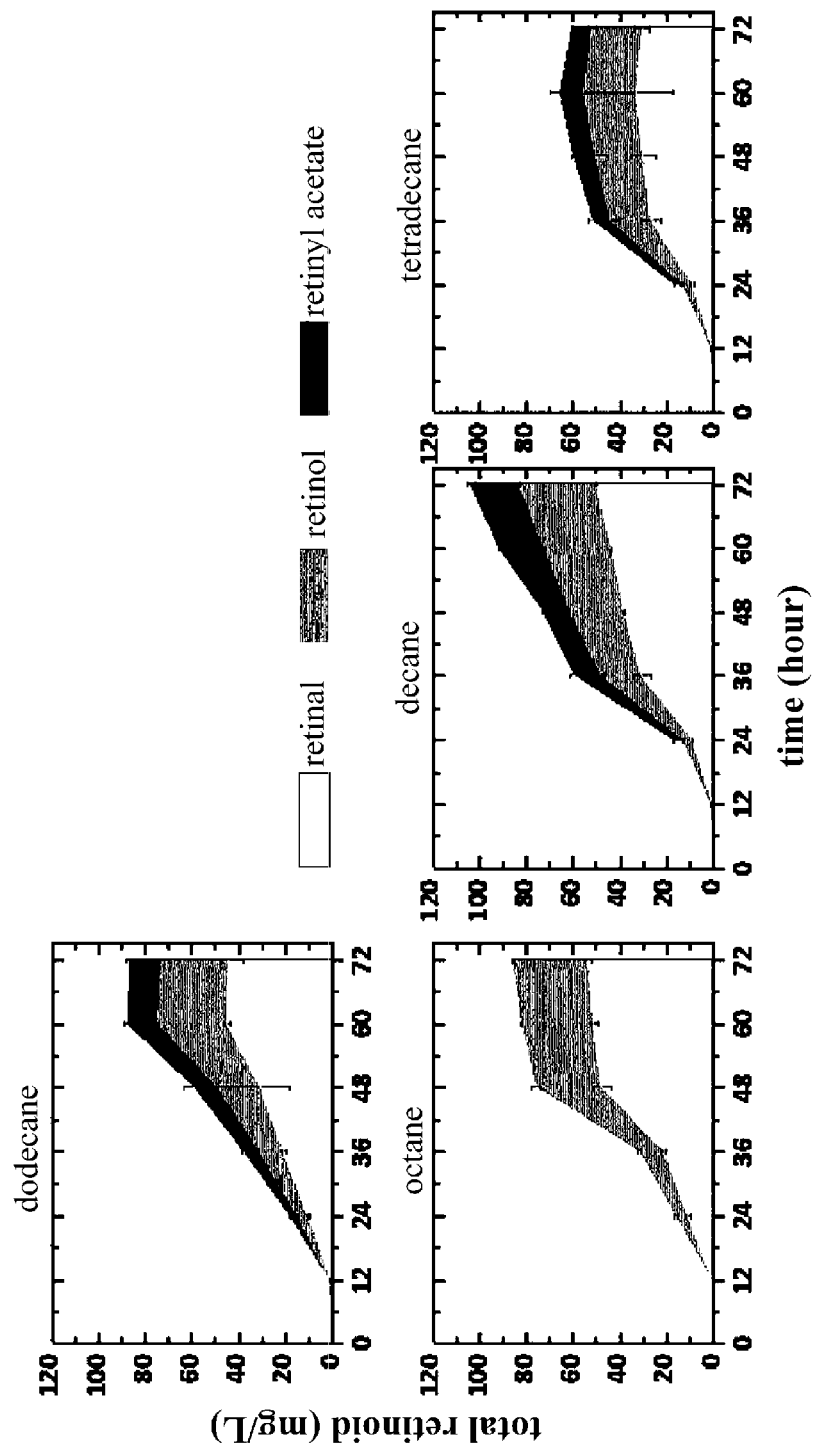
FIGS. 17 and 18 illustrate results of retinoid production and cell growth of *Escherichia coli* (pT-DHBSR/pS-NA) in the presence of different alkanes, respectively.
Figure 18:
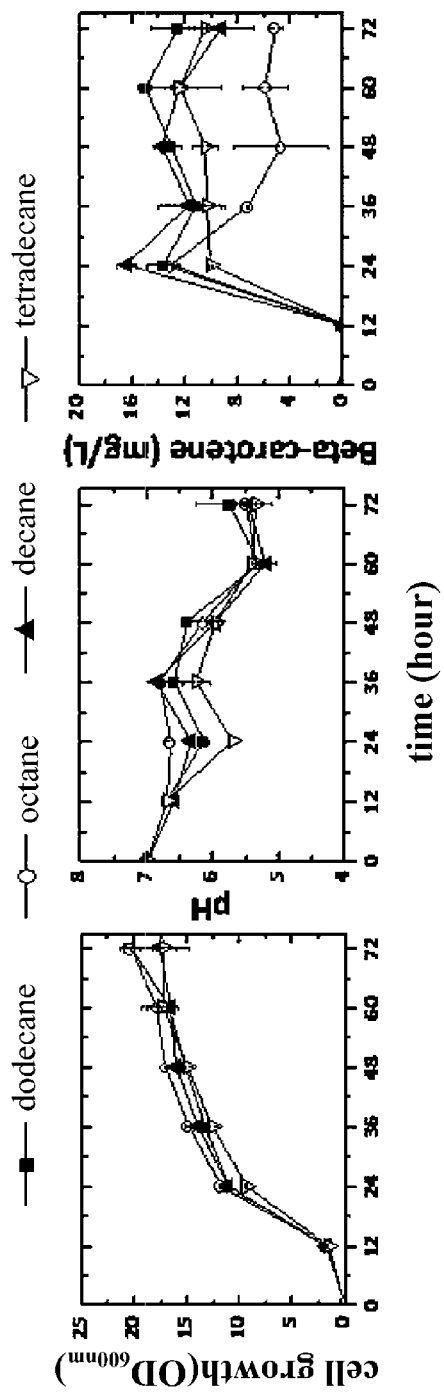

FIG. 17 illustrates results of retinoid production in the presence of alkane. FIG. 18 illustrates results of growth of the retinoid producing strain in the presence of alkane.

As shown in FIG. 17, a total 108 mg/L of retinoid was produced in case of using decane. Alternatively, bacterial cell proliferation, pH and an amount of β-carotene in the bacterial cell did not show a considerable difference depending upon the presence of alkanes. Therefore, it is considered that decane may be more advantageous in retinoid production, as compared to dodecane. When using octane, production of retinal and retinol was similar to other alkanes, whereas retinyl acetate was almost not produced. Tetradecane showed a lower productivity of whole retinoids, as compared to other alkanes.

(2) Production of Retinoid in Medium Including Mineral Oil (2.1) Lightweight Mineral Oil The lightweight mineral oil is cheap and has an economical advantage, as compared to alkanes. A strain DH5α including transformed pT-DHBSR/pSNA (DH5α(pT-DHBSR/pSNA)) was used, and after adding the lightweight mineral oil in different volumes to 5 ml of medium, respectively, culturing was conducted according to such conditions as described in "Bacteria strain and culture conditions." The medium used herein was a 2YT medium including 0.2% (w/v) of arabinose and 2.0% (w/v) of glycerol added thereto.

Figure 19:
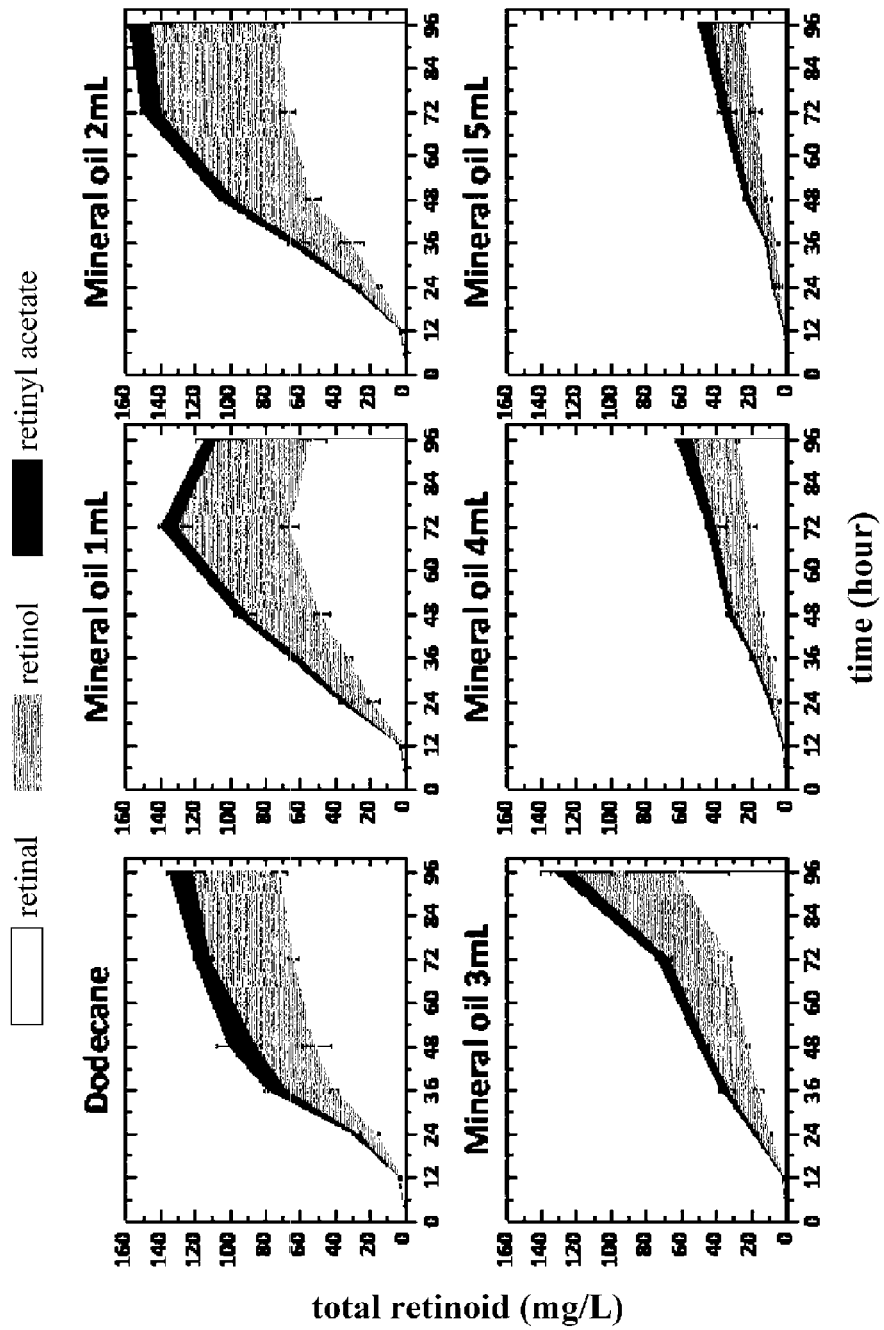
FIGS. 19, 20 and 21 illustrate results of retinoid production, cell growth, and cell specific retinoids productivity of *Escherichia coli* (pT-DHBSR/pS-NA) in the presence of different volumes of lightweight mineral oil, respectively.
Figure 20:
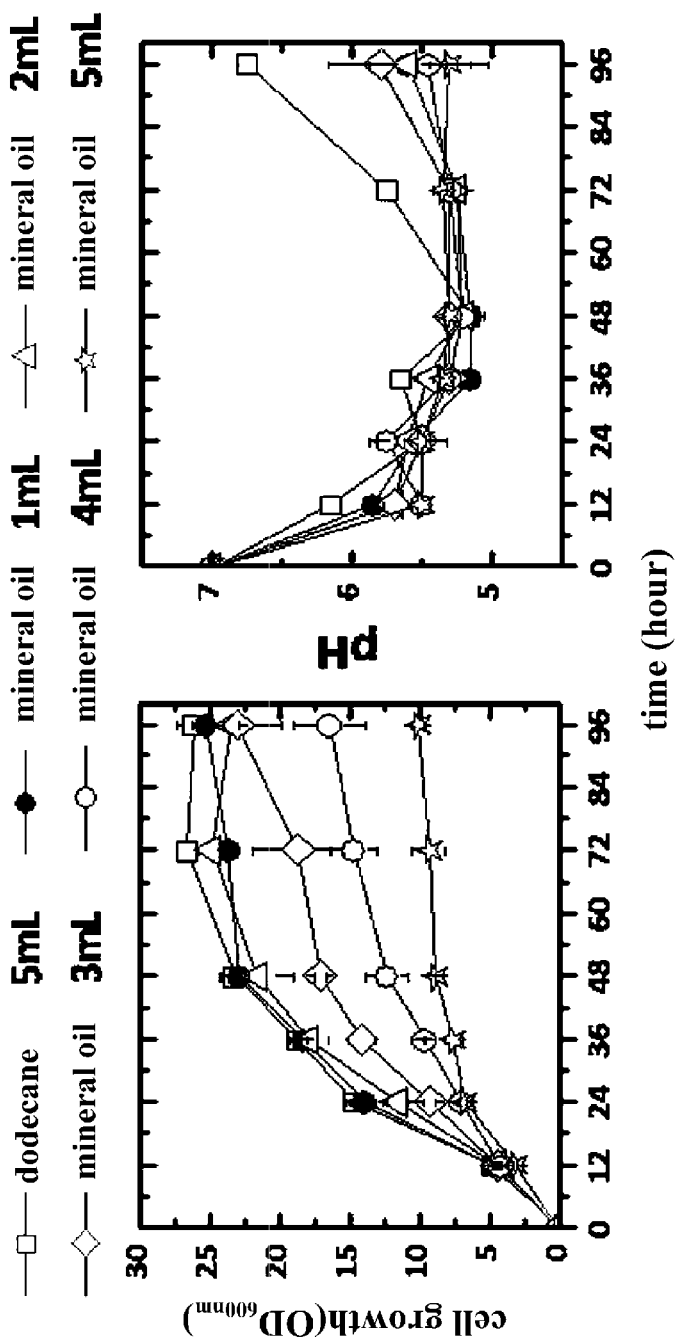

FIG. 19 illustrates results of retinoid production in the presence of lightweight mineral oil. FIG. 20 illustrates results of strain growth in the presence of lightweight mineral oil.

As shown in FIG. 19, 158 mg/L of retinoid was produced in the presence of the lightweight mineral oil in an amount of 2 ml, as compared to 136.1 mg/L of retinoid produced using 5 mL of dodecane. As shown in FIG. 20, pH was not considerably different other than the case of using dodecane. On the other hand, bacterial cell growth was reduced as an amount of the lightweight mineral oil increased. The reason of this condition was deemed because the medium and mineral oil were not sufficiently admixed due to a high viscosity and specific gravity of the lightweight mineral oil. Owing to a decrease in growth of the bacterial cell, the retinoid production was also reduced.

Figure 21:
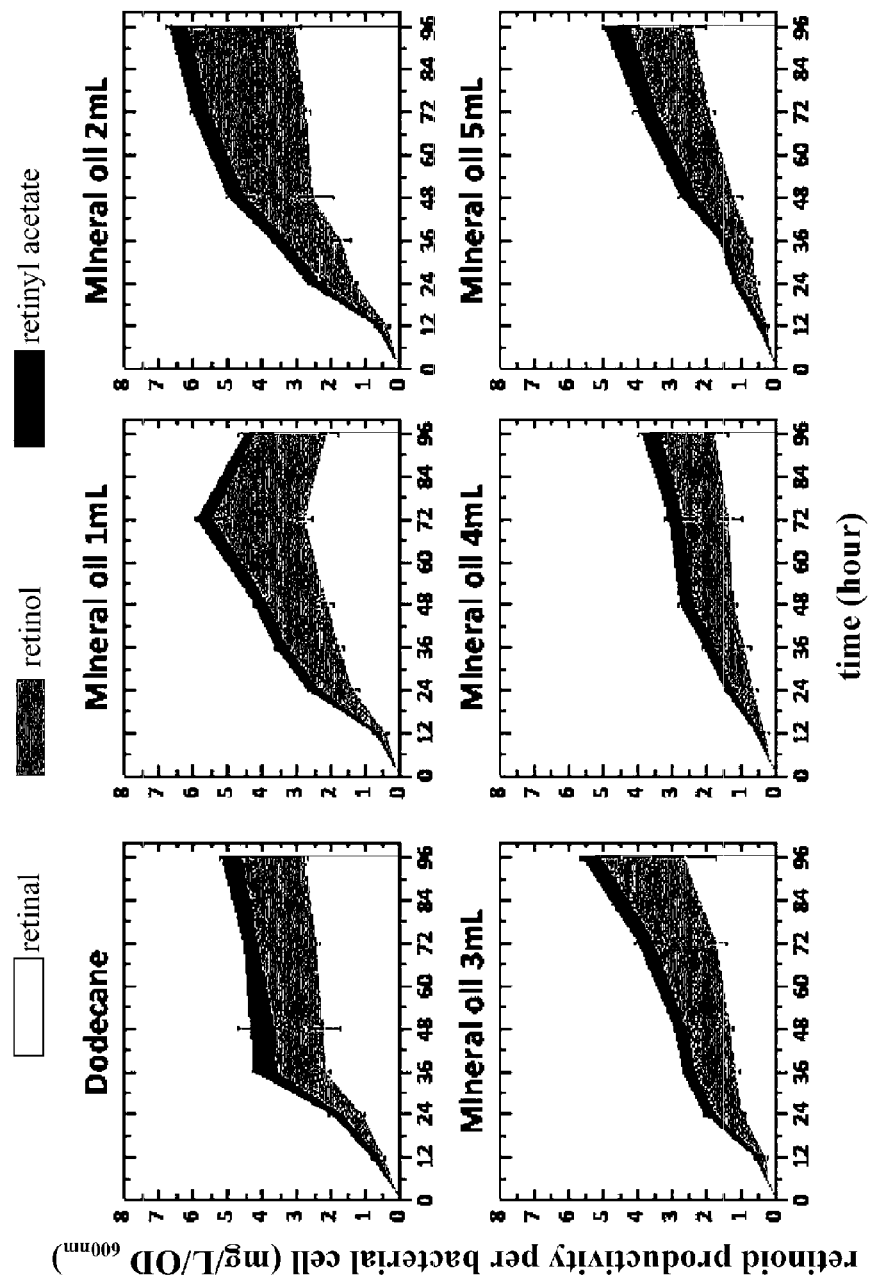

FIG. 21 illustrates cell specific retinoids productivity. As shown in FIG. 21, a specific productivity of about 5 mg/L/ $OD_{600}$ nm was observed regardless of an amount of mineral oil.

(2.2) Heavy Mineral Oil

The heavy mineral oil is cheaper than the lightweight mineral oil. A strain DH5α including transformed pT-DHBSR/pSNA (DH5α(pT-DHBSR/pSNA)) was used, and after adding 2 ml of heavy mineral oil to 5 ml of medium, culturing was conducted according to such conditions as described in "Bacteria strain and culture conditions." The medium used herein was a 2YT medium including 0.2% (w/v) of arabinose and 2.0% (w/v) of glycerol added thereto.

Figure 22:
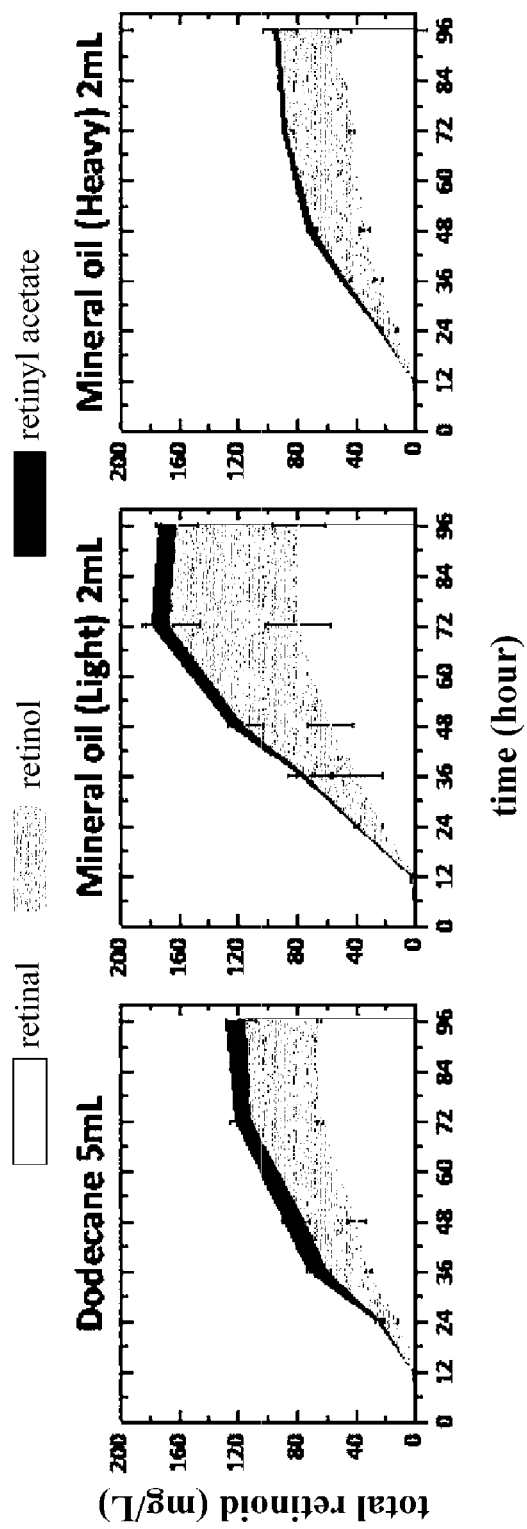
FIGS. 22 and 23 illustrate results of retinoid production and cell growth of *Escherichia coli* (pT-DHBSR/pS-NA) in the presence of heavy mineral oil, respectively.
Figure 23:
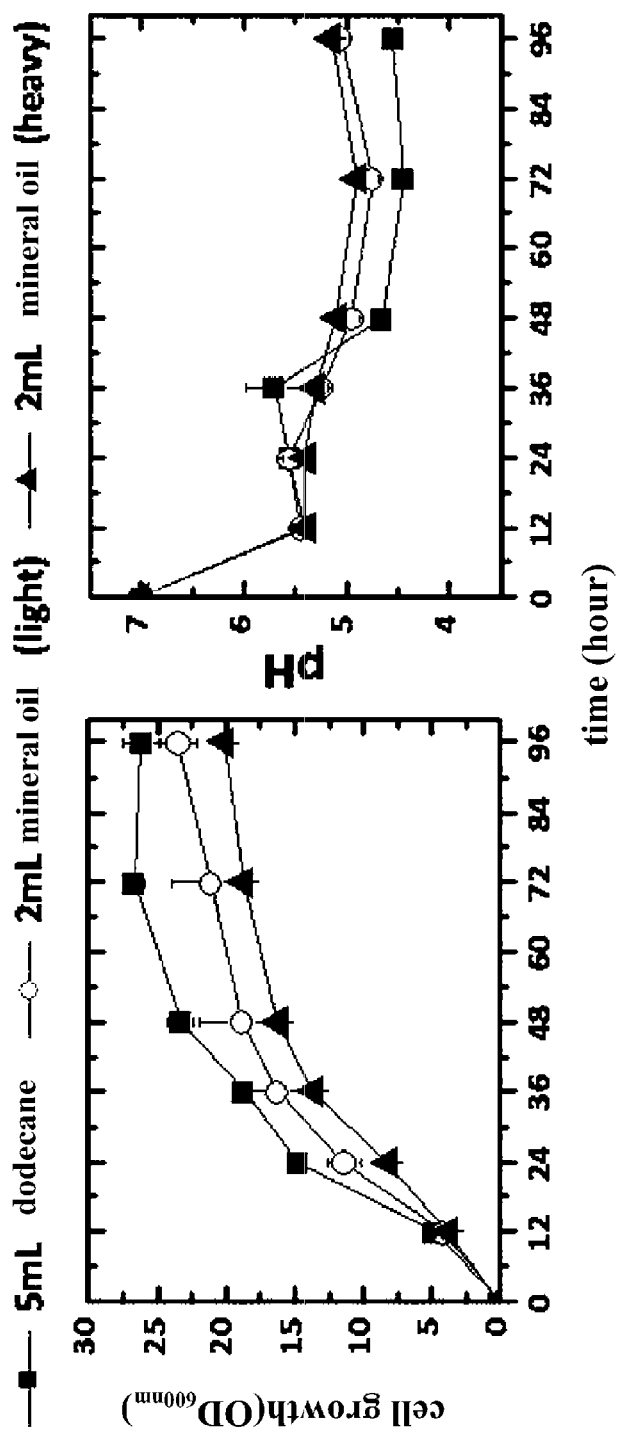

FIG. 22 illustrates results of retinoid production in the presence of heavy mineral oil. FIG. 23 illustrates results of strain growth in the presence of heavy mineral oil. As shown in FIGS. 22 and 23, the heavy mineral oil involved lower cell growth, as compared to the lightweight mineral oil and dodecane. Further, 104.6 mg/L of retinoid was produced. The reason of this condition was deemed because the medium and mineral oil were not sufficiently admixed due to a viscosity of the heavy mineral oil.

Except that a test tube was tilted and mounted on an incubator, cell culture was performed by the same procedures as described above. By tilting the test tube, effects of agitation were improved to thus allow the medium and mineral oil to be admixed more effectively.

Figure 24:
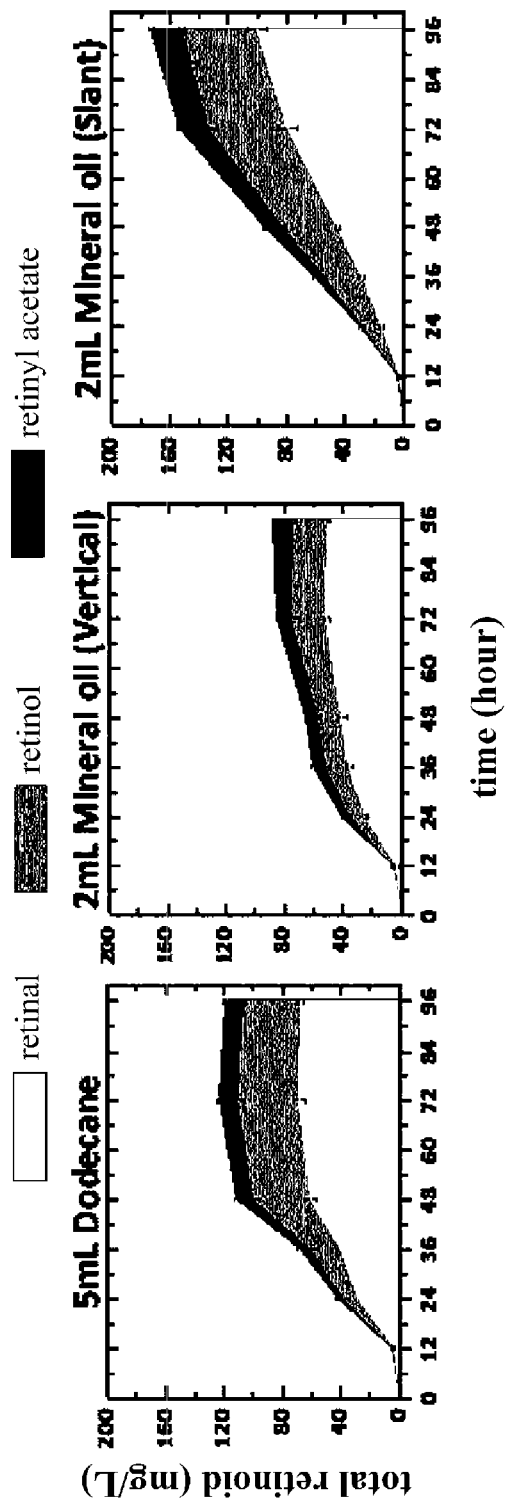
FIGS. 24 and 25 illustrate results of retinoid production and cell growth of *Escherichia coli* (pT-DHBSR/pS-NA) when culturing was conducted by tilting a test tube, respectively.
Figure 25:
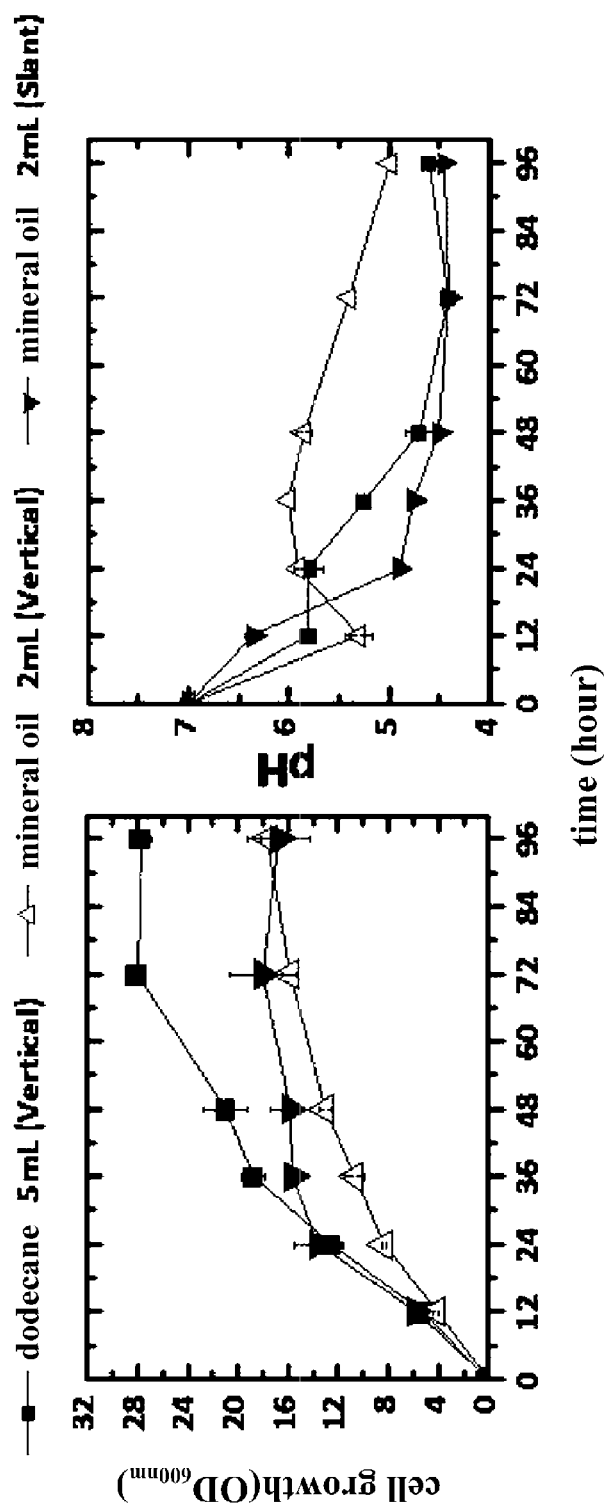

FIG. 24 illustrates results of retinoid production when the culturing was conducted in a tilted test tube. FIG. 25 illustrates results of strain growth when the culturing was conducted in the tilted test tube. As shown in FIGS. 24 and 25, the cell growth and retinoid production were increased when the culturing was conducted in the tilted test tube. More particularly, the retinoid was produced in an amount of 88.2 mg/L at 96 hours in a vertically-mounted test tube, while the retinoid productivity reached 173.9 mg/L in the tilted test tube.

The above results indicated that mixing the lightweight and/or heavy mineral oils with the medium is an important factor in retinoid production since the mineral oils have a high viscosity. Accordingly, the foregoing lightweight and/or heavy mineral oils may be used for retinoid by properly agitating the same during culturing.

(3) Production of Retinoid in Medium Including Skin-Friendly Lipophilic Substance Retinoid was produced in a medium including a skin-friendly lipophilic substance. As the skin-friendly lipophilic substance, isopropyl myristate (IPM), dioctanoyl-decanoyl glycerol (ODO), cetyl ethylhexanoate (CEH) and phytosqualane were used.

A strain DH5α including transformed pT-DHBSR/pSNA (DH5α(pT-DHBSR/pSNA)) was used, and after adding 2 ml of heavy mineral oil to 5 ml of medium, culturing was conducted according to such conditions as described in "Bacteria strain and culture conditions." The medium used herein was a 2YT medium including 0.2% (w/v) of arabinose and 2.0% (w/v) of glycerol added thereto. A control was prepared by adding 5 mL of dodecane to the medium.

Figure 26:
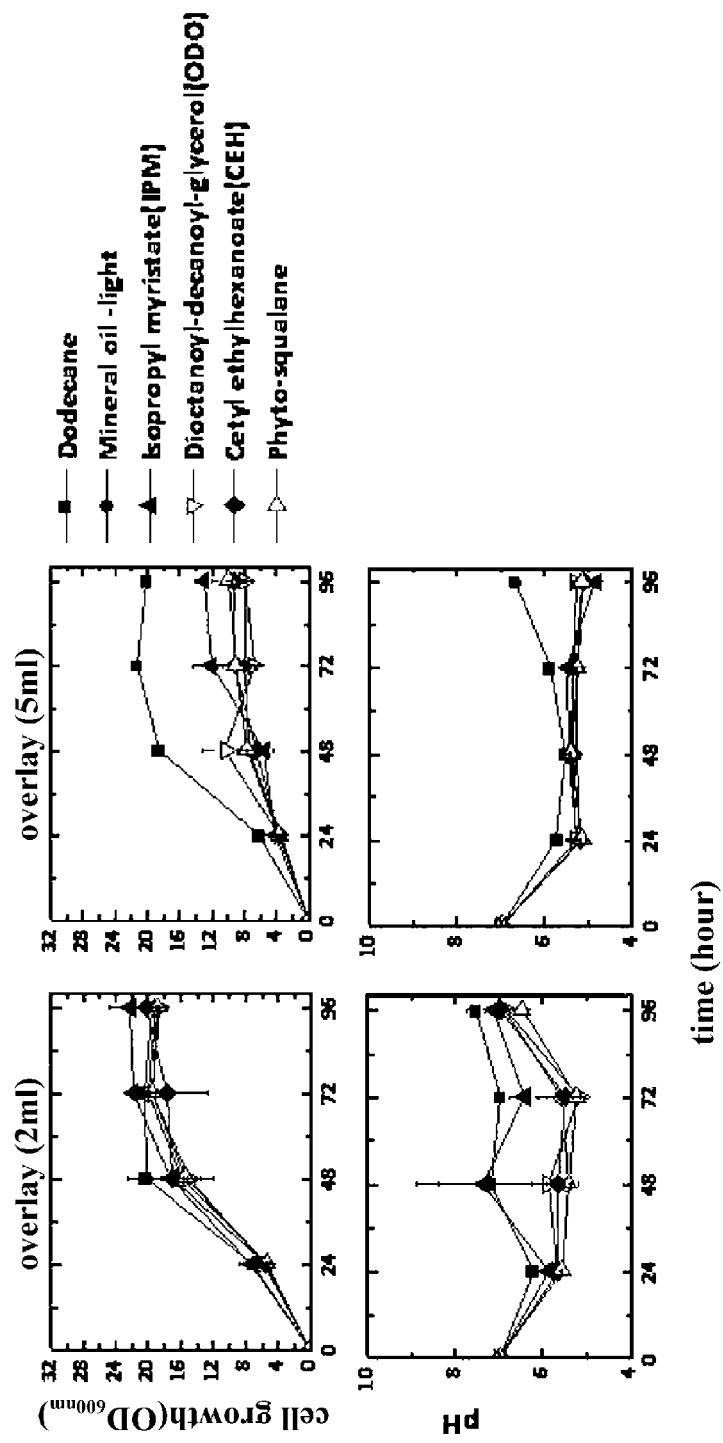
FIG. 26 illustrates cell growth and pH of *Escherichia coli* (pT-DHBSR/pS-NA) in the presence of skin-friendly lipophilic substance.
Figure 27:
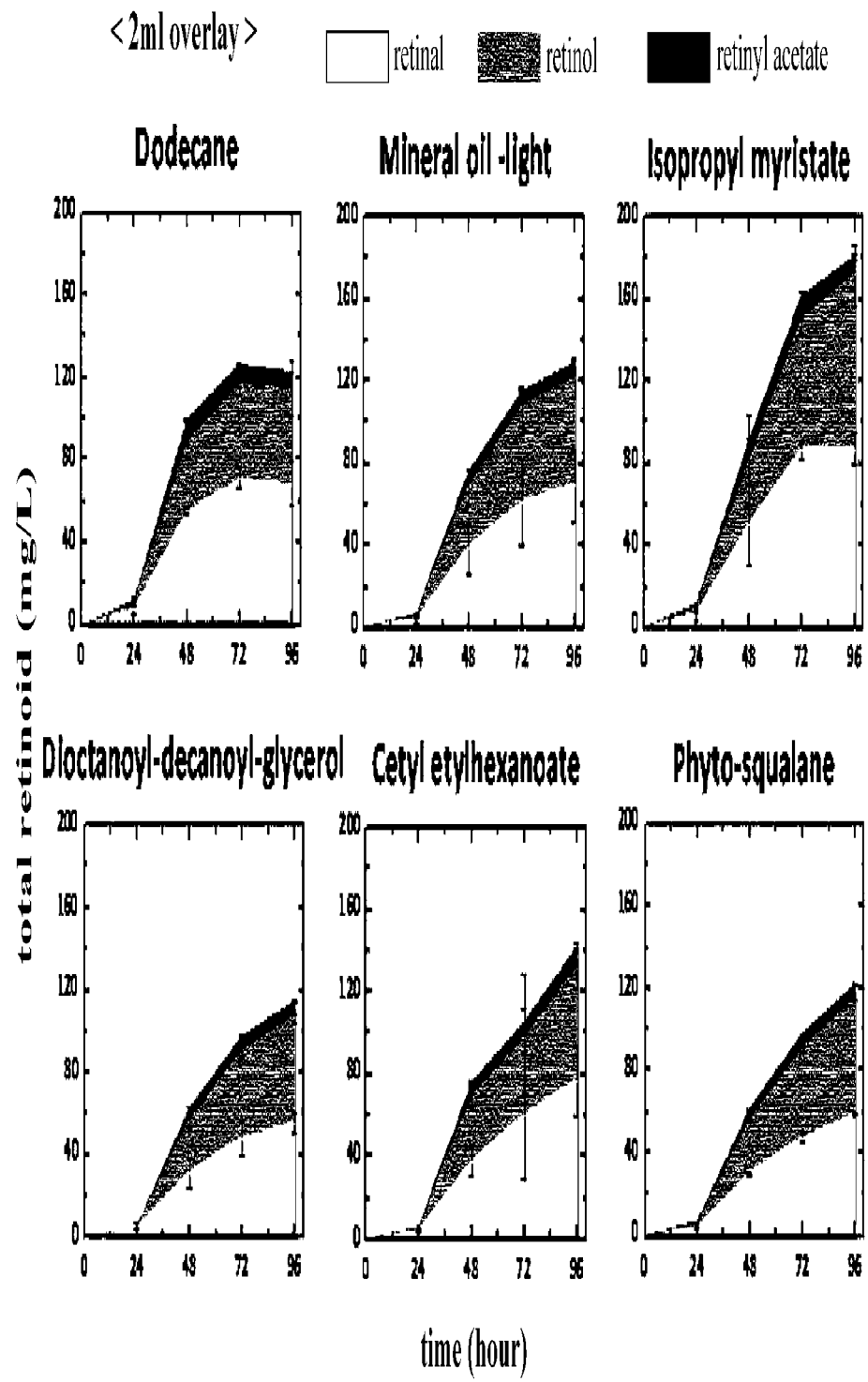
FIGS. 27 and 28 illustrate results of retinoid production of *Escherichia coli* depending on different kinds and amounts of skin-friendly lipophilic substance, respectively.
Figure 28:
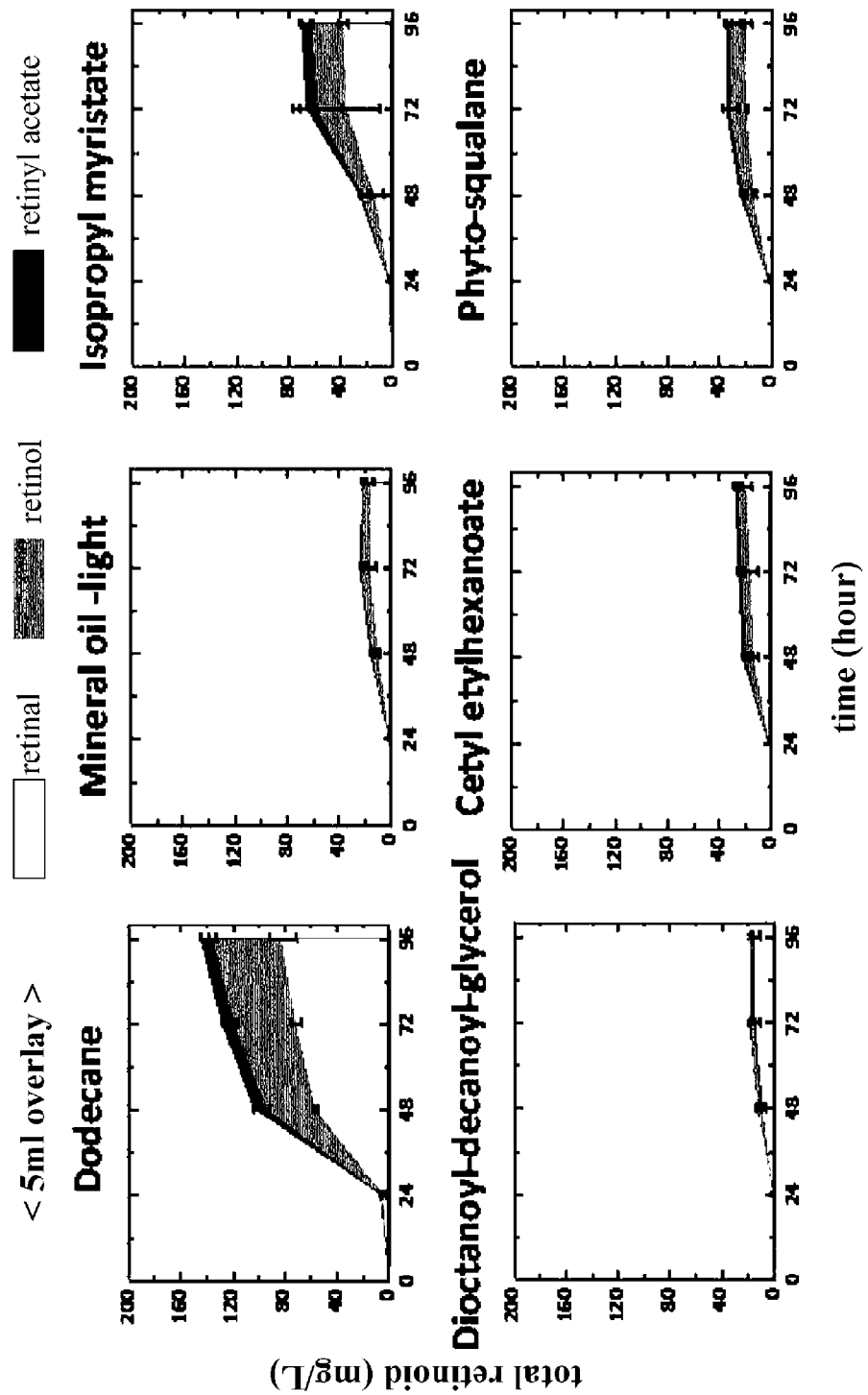

FIG. 26 illustrates cell growth and pH in the presence of skin-friendly lipophilic substance. FIGS. 27 and 28 illustrate results of retinoid production depending on an amount of skin-friendly lipophilic substance. As shown in FIGS. 27 and 28, in case of lipophilic substances other than dodecane, using 2 ml of lipophilic substance has achieved an increase in retinoid productivity, as compared to 5 ml of the same. In other words, when 2 ml of lipophilic substance was added to 5 ml of medium including the lightweight mineral oil, IPM, ODO, CEH and phytosqualane, large amount of retinoid was produced. Especially, when using IPM among IPM, ODO, CEH and phytosqualane, the largest amount of retinoid was produced. More specifically, when adding 2 ml of IPM, 180 mg/L of retinoid was produced. For IPM, in consideration of similar growth of bacterial cell, it is presumed to have a high specific productivity per bacterial cell.

---

The invention claimed is:

1. A method for production of retinoid from a microorganism, comprising:
   culturing a microorganism having retinoid producing efficacy in a medium containing a lipophilic substance; and
   isolating said retinoid from said lipophilic substance without degrading a cell wall of said microorganism;
   wherein said microorganism transformed with:
   a gene encoding acetyl-CoA acetyl transferase/hydroxymethylglutaryl(HMG)-CoA reductase comprising the amino acid sequence of SEQ ID NO: 1 from *Enterococcus faecalis*;
   a gene encoding HMG-CoA synthase comprising the amino acid sequence of SEQ ID NO: 2 from *Enterococcus faecalis*;
   a gene encoding mevalonate kinase comprising the amino acid sequence of SEQ ID NO: 3 from *Streptococcus pneumoniae*;
   a gene encoding phosphomevalonate kinase comprising the amino acid sequence of SEQ ID NO: 4 from *Streptococcus pneumoniae*;
   a gene encoding mevalonate diphosphate decarboxylase comprising the amino acid sequence of SEQ ID NO: 5 from *Streptococcus pneumoniae*;
   a gene encoding isopentinyl diphosphate (IPP) isomerase comprising the amino acid sequence of SEQ ID NO: 6 from *Escherichia coli*;
   a gene encoding geranylgeranyl pyrophosphate (GGPP) synthase comprising the amino acid sequence of SEQ ID NO: 7 from *Pantoea agglomerans*;
   a gene encoding phytoene synthase comprising the amino acid sequence of SEQ ID NO:8 from *Pantoea agglomerans*;
   a gene encoding phytoene dehydrogenase comprising the amino acid sequence of SEQ ID NO: 9 from *Pantoea agglomerans*; and
   a gene encoding lycopene β-cyclase comprising the amino acid sequence of SEQ ID NO: 10 from *Pantoea ananatis*.

2. The method of claim 1, wherein said microorganism is a bacteria, a fungi, or a combination thereof.

3. The method of claim 1, wherein said microorganism is of the genus *Escherichia*, the genus *Bacillus*, the genus *Corynebacterium*, the genus *Kluyveromyces* or a combination thereof.

4. The method of claim 1, wherein said lipophilic substance is an alkane compound having 8 to 50 carbon atoms, a compound represented by Formula 1 below, a compound represented by Formula 2 below, or a combination thereof:

$$R_1(CO)OR_2 \quad \text{[Formula 1]}$$

wherein $R_1$ and $R_2$ are each independently alkyl having 8 to 50 carbon atoms, and CO represents a carbonyl group; and

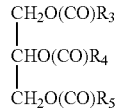

[Formula 2]

wherein $R_3$, $R_4$ and $R_5$ are each independently alkyl having 8 to 50 carbon atoms, and CO represents a carbonyl group.

5. The method of claim 1, wherein said lipophilic substance is octane, decane, dodecane, tetradecane, phytosqualane, mineral oil, isopropyl myristate, cetyl ethylhexanoate, dioctanoyl decanoyl glycerol, squalane, or a combination thereof.

6. The method of claim 1, wherein a ratio by volume of said medium to said lipophilic substance ranges from 1:0.2 to 3.0.

7. The method of claim 1, wherein said culturing is performed while agitating.

8. The method of claim 1, wherein said medium further comprises glycerol.

9. The method of claim 1, wherein said medium further comprises glucose.

10. The method of claim 1, wherein said isolating includes removing cells from a culture solution and then isolating said retinoid from dodecane.

11. The method of claim 1, wherein said retinoid is selected from the group consisting of retinal, retinol, retinyl ester and retinoic acid.

12. The method of claim 1, wherein said microorganism is *Escherichia coli*.

13. The method of claim 12, wherein said *Escherichia coli* is DH5α, MG1655, BL21 (DE), S17-1, XL1-Blue, BW25113 or a combination thereof.

14. The method of claim 1, wherein said microorganism is further transformed with a gene selected from the group consisting of:
   a gene encoding β-carotene monooxygenase comprising the amino acid sequence of SEQ ID NO: 13 from uncultured marine bacterium 66A03;
   a gene encoding β-carotene 15,15'-monooxygenase comprising the amino acid sequence of SEQ ID NO: 14 from *Mus musculus*;
   a gene encoding brp-like protein 2 (brp 2) comprising the amino acid sequence of SEQ ID NO: 15 from Natronomonas *pharaonis* ATCC35678; and
   a gene encoding β-carotene monooxygenase comprising the amino acid sequence of SEQ ID NO: 16 or 17 from *Halobacterium salinarum* ATCC700922.

15. The method of claim 1, wherein said microorganism is further transformed by a gene comprising the nucleotide sequence of SEQ ID NO: 32, wherein said gene is codon optimized for *Escherichia coli*.

16. The method of claim 1, wherein said microorganism is further transformed by a gene encoding 1-deoxyxylolose-5-phosphate (DXP) synthase comprising the amino acid sequence of SEQ ID NO: 11 from *Escherichia coli*.

17. The method of claim 1, wherein said microorganism is further transformed by a gene encoding IPP isomerase comprising the amino acid sequence of SEQ ID NO: 12 from *Haematococcus pluvialis*.

18. The method of claim 1, wherein said microorganism is *Escherichia coli* DH5α/pTDHB/pSNA deposited under Accession No. KCTC 11254BP or *Escherichia coli* DH5α/pTDHBSR/pSNA deposited under Accession No. KCTC 11255BP.

19. The method of claim 1, wherein said microorganism is of the genus *Escherichia*.

* * * * *